(12) United States Patent
Trees et al.

(10) Patent No.: US 10,856,934 B2
(45) Date of Patent: Dec. 8, 2020

(54) ELECTROSURGICAL INSTRUMENT WITH ELECTRICALLY CONDUCTIVE GAP SETTING AND TISSUE ENGAGING MEMBERS

(71) Applicant: Ethicon Endo-Surgery, LLC, Guaynabo, PR (US)

(72) Inventors: Gregory A. Trees, Loveland, OH (US); Megan A. Broderick, West Chester, OH (US); Frederick E. Shelton, IV, Hillsboro, OH (US); Chad P. Boudreaux, Cincinnati, OH (US); John M. Sarley, Mason, OH (US); David C. Yates, West Chester, OH (US)

(73) Assignee: ETHICON LLC, Guaynabo, PR (US)

( * ) Notice: Subject to any disclaimer, the term of this patent is extended or adjusted under 35 U.S.C. 154(b) by 778 days.

(21) Appl. No.: 15/142,609

(22) Filed: Apr. 29, 2016

(65) Prior Publication Data

US 2017/0312019 A1 Nov. 2, 2017

(51) Int. Cl.
*A61B 18/14* (2006.01)
*A61B 18/00* (2006.01)
*A61B 90/00* (2016.01)

(52) U.S. Cl.
CPC ...... *A61B 18/1447* (2013.01); *A61B 18/1442* (2013.01); *A61B 18/1445* (2013.01); *A61B 2018/00053* (2013.01); *A61B 2018/0063* (2013.01); *A61B 2018/00589* (2013.01); *A61B 2018/00595* (2013.01); *A61B 2018/1455* (2013.01); *A61B 2090/034* (2016.02)

(58) Field of Classification Search
CPC ........ A61B 18/1445; A61B 2017/2926; A61B 2017/2937
See application file for complete search history.

(56) References Cited

U.S. PATENT DOCUMENTS

| | | | |
|---|---|---|---|
| 2,366,274 | A | 1/1945 | Luth et al. |
| 2,458,152 | A | 1/1949 | Eakins |
| 2,510,693 | A | 6/1950 | Green |

(Continued)

FOREIGN PATENT DOCUMENTS

| | | |
|---|---|---|
| CN | 1634601 A | 7/2005 |
| CN | 1922563 A | 2/2007 |

(Continued)

OTHER PUBLICATIONS

U.S. Appl. No. 15/142,589, filed Apr. 29, 2016.

(Continued)

*Primary Examiner* — Jaymi E Della
*Assistant Examiner* — Sean W Collins

(57) ABSTRACT

An end effector includes a grasping portion that includes a first jaw member having a first electrode, a second jaw member having a second electrode, a first electrically conductive member located either on the first jaw member or the second jaw member, and a gap setting portion having a second electrically conductive member located at the distal end of either the first jaw member or the second jaw member. The electrically insulative member is sized and configured to engage tissue and the second electrically conductive member sized and configured to define a minimum distance between the first and second electrodes.

18 Claims, 18 Drawing Sheets

(56) References Cited

U.S. PATENT DOCUMENTS

| | | |
|---|---|---|
| 2,736,960 A | 3/1956 | Armstrong |
| 2,849,788 A | 9/1958 | Creek |
| 2,867,039 A | 1/1959 | Zach |
| 3,015,961 A | 1/1962 | Roney |
| 3,043,309 A | 7/1962 | McCarthy |
| 3,166,971 A | 1/1965 | Stoecker |
| 3,358,676 A | 12/1967 | Frei et al. |
| 3,525,912 A | 8/1970 | Wallin |
| 3,526,219 A | 9/1970 | Balamuth |
| 3,580,841 A | 5/1971 | Cadotte et al. |
| 3,614,484 A | 10/1971 | Shoh |
| 3,636,943 A | 1/1972 | Balamuth |
| 3,703,651 A | 11/1972 | Blowers |
| 3,710,399 A | 1/1973 | Hurst |
| 3,776,238 A | 12/1973 | Peyman et al. |
| 3,777,760 A | 12/1973 | Essner |
| 3,805,787 A | 4/1974 | Banko |
| 3,862,630 A | 1/1975 | Balamuth |
| 3,900,823 A | 8/1975 | Sokal et al. |
| 3,906,217 A | 9/1975 | Lackore |
| 3,918,442 A | 11/1975 | Nikolaev et al. |
| 3,946,738 A | 3/1976 | Newton et al. |
| 3,955,859 A | 5/1976 | Stella et al. |
| 3,956,826 A | 5/1976 | Perdreaux, Jr. |
| 3,988,535 A | 10/1976 | Hickman et al. |
| 4,005,714 A | 2/1977 | Hiltebrandt |
| 4,034,762 A | 7/1977 | Cosens et al. |
| 4,047,136 A | 9/1977 | Satto |
| 4,058,126 A | 11/1977 | Leveen |
| 4,063,561 A | 12/1977 | McKenna |
| 4,099,192 A | 7/1978 | Aizawa et al. |
| 4,156,187 A | 5/1979 | Murry et al. |
| 4,188,927 A | 2/1980 | Harris |
| 4,200,106 A | 4/1980 | Douvas et al. |
| 4,203,430 A | 5/1980 | Takahashi |
| 4,220,154 A | 9/1980 | Semm |
| 4,237,441 A | 12/1980 | van Konynenburg et al. |
| 4,278,077 A | 7/1981 | Mizumoto |
| 4,281,785 A | 8/1981 | Brooks |
| 4,304,987 A | 12/1981 | van Konynenburg |
| 4,314,559 A | 2/1982 | Allen |
| 4,384,584 A | 5/1983 | Chen |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,585,282 A | 4/1986 | Bosley |
| 4,597,390 A | 7/1986 | Mulhollan et al. |
| 4,617,927 A | 10/1986 | Manes |
| 4,633,874 A | 1/1987 | Chow et al. |
| 4,634,420 A | 1/1987 | Spinosa et al. |
| 4,640,279 A | 2/1987 | Beard |
| 4,655,746 A | 4/1987 | Daniels et al. |
| 4,671,287 A | 6/1987 | Fiddian-Green |
| 4,708,127 A | 11/1987 | Abdelghani |
| 4,735,603 A | 4/1988 | Goodson et al. |
| 4,761,871 A | 8/1988 | O'Connor et al. |
| 4,777,951 A | 10/1988 | Cribier et al. |
| 4,797,803 A | 1/1989 | Carroll |
| 4,798,588 A | 1/1989 | Aillon |
| 4,802,461 A | 2/1989 | Cho |
| 4,803,506 A | 2/1989 | Diehl et al. |
| 4,830,462 A | 5/1989 | Karny et al. |
| 4,832,683 A | 5/1989 | Idemoto et al. |
| 4,838,853 A | 6/1989 | Parisi |
| 4,849,133 A | 7/1989 | Yoshida et al. |
| 4,850,354 A | 7/1989 | McGurk-Burleson et al. |
| 4,860,745 A | 8/1989 | Farin et al. |
| 4,865,159 A | 9/1989 | Jamison |
| 4,878,493 A | 11/1989 | Pasternak et al. |
| 4,880,015 A | 11/1989 | Nierman |
| 4,896,009 A | 1/1990 | Pawlowski |
| 4,910,389 A | 3/1990 | Sherman et al. |
| 4,910,633 A | 3/1990 | Quinn |
| 4,911,148 A | 3/1990 | Sosnowski et al. |
| 4,919,129 A | 4/1990 | Weber, Jr. et al. |
| 4,920,978 A | 5/1990 | Colvin |
| 4,922,902 A | 5/1990 | Wuchinich et al. |
| 4,936,842 A | 6/1990 | D'Amelio et al. |
| 4,961,738 A | 10/1990 | Mackin |
| 4,967,670 A | 11/1990 | Morishita et al. |
| 4,981,756 A | 1/1991 | Rhandhawa |
| 5,007,919 A | 4/1991 | Silva et al. |
| 5,019,075 A | 5/1991 | Spears et al. |
| 5,020,514 A | 6/1991 | Heckele |
| 5,026,387 A | 6/1991 | Thomas |
| 5,061,269 A | 10/1991 | Muller |
| 5,093,754 A | 3/1992 | Kawashima |
| 5,099,216 A | 3/1992 | Pelrine |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,112,300 A | 5/1992 | Ureche |
| 5,123,903 A | 6/1992 | Quaid et al. |
| 5,150,102 A | 9/1992 | Takashima |
| 5,150,272 A | 9/1992 | Danley et al. |
| 5,156,633 A | 10/1992 | Smith |
| 5,160,334 A | 11/1992 | Billings et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |
| 5,184,605 A | 2/1993 | Grzeszykowski |
| 5,188,102 A | 2/1993 | Idemoto et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,217,460 A | 6/1993 | Knoepfler |
| 5,221,282 A | 6/1993 | Wuchinich |
| 5,226,910 A | 7/1993 | Kajiyama et al. |
| 5,234,428 A | 8/1993 | Kaufman |
| 5,241,236 A | 8/1993 | Sasaki et al. |
| 5,253,647 A | 10/1993 | Takahashi et al. |
| 5,254,130 A | 10/1993 | Poncet et al. |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,267,091 A | 11/1993 | Chen |
| 5,282,800 A | 2/1994 | Foshee et al. |
| 5,285,945 A | 2/1994 | Brinkerhoff et al. |
| 5,290,286 A | 3/1994 | Parins |
| 5,293,863 A | 3/1994 | Zhu et al. |
| 5,304,115 A | 4/1994 | Pflueger et al. |
| D347,474 S | 5/1994 | Olson |
| 5,309,927 A | 5/1994 | Welch |
| 5,312,023 A | 5/1994 | Green et al. |
| 5,313,306 A | 5/1994 | Kuban et al. |
| 5,318,563 A | 6/1994 | Malis et al. |
| 5,318,564 A | 6/1994 | Eggers |
| 5,318,565 A | 6/1994 | Kuriloff et al. |
| 5,318,570 A | 6/1994 | Hood et al. |
| 5,318,589 A | 6/1994 | Lichtman |
| 5,322,055 A | 6/1994 | Davison et al. |
| 5,324,260 A | 6/1994 | O'Neill et al. |
| 5,324,299 A | 6/1994 | Davison et al. |
| 5,326,013 A | 7/1994 | Green et al. |
| 5,330,471 A | 7/1994 | Eggers |
| 5,330,502 A | 7/1994 | Hassler et al. |
| 5,333,624 A | 8/1994 | Tovey |
| 5,339,723 A | 8/1994 | Huitema |
| 5,342,359 A | 8/1994 | Rydell |
| 5,344,420 A | 9/1994 | Hilal et al. |
| 5,346,502 A | 9/1994 | Estabrook et al. |
| 5,352,219 A | 10/1994 | Reddy |

(56) References Cited

U.S. PATENT DOCUMENTS

| | | |
|---|---|---|
| 5,359,992 A | 11/1994 | Hori et al. |
| 5,361,583 A | 11/1994 | Huitema |
| 5,366,466 A | 11/1994 | Christian et al. |
| 5,370,640 A | 12/1994 | Kolff |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,389,098 A | 2/1995 | Tsuruta et al. |
| 5,395,033 A | 3/1995 | Byrne et al. |
| 5,395,312 A | 3/1995 | Desai |
| 5,395,331 A | 3/1995 | O'Neill et al. |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,409,483 A | 4/1995 | Campbell et al. |
| D358,887 S | 5/1995 | Feinberg |
| 5,411,481 A | 5/1995 | Allen et al. |
| 5,413,575 A | 5/1995 | Haenggi |
| 5,417,709 A | 5/1995 | Slater |
| 5,419,761 A | 5/1995 | Narayanan et al. |
| 5,421,829 A | 6/1995 | Olichney et al. |
| 5,428,504 A | 6/1995 | Bhatla |
| 5,429,131 A | 7/1995 | Scheinman et al. |
| 5,431,640 A | 7/1995 | Gabriel |
| 5,443,463 A | 8/1995 | Stern et al. |
| 5,445,615 A | 8/1995 | Yoon |
| 5,445,638 A | 8/1995 | Rydell et al. |
| 5,449,370 A | 9/1995 | Vaitekunas |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,472,443 A | 12/1995 | Cordis et al. |
| 5,476,479 A | 12/1995 | Green et al. |
| 5,477,788 A | 12/1995 | Morishita |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,489,256 A | 2/1996 | Adair |
| 5,496,317 A | 3/1996 | Goble et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,648 A | 7/1996 | Yoon |
| 5,540,681 A | 7/1996 | Strul et al. |
| 5,542,916 A | 8/1996 | Hirsch et al. |
| 5,542,938 A | 8/1996 | Avellanet et al. |
| 5,558,671 A | 9/1996 | Yates |
| 5,562,609 A | 10/1996 | Brumbach |
| 5,562,610 A | 10/1996 | Brumbach |
| 5,562,657 A | 10/1996 | Griffin |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,601,601 A | 2/1997 | Tal et al. |
| 5,604,531 A | 2/1997 | Iddan et al. |
| 5,607,436 A | 3/1997 | Pratt et al. |
| 5,607,450 A | 3/1997 | Zvenyatsky et al. |
| 5,611,813 A | 3/1997 | Lichtman |
| 5,618,307 A | 4/1997 | Donlon et al. |
| 5,618,492 A | 4/1997 | Auten et al. |
| 5,624,452 A | 4/1997 | Yates |
| 5,626,578 A | 5/1997 | Tihon |
| 5,628,760 A | 5/1997 | Knoepfler |
| 5,630,420 A | 5/1997 | Vaitekunas |
| 5,632,432 A | 5/1997 | Schulze et al. |
| D381,077 S | 7/1997 | Hunt |
| 5,643,175 A | 7/1997 | Adair |
| 5,645,065 A | 7/1997 | Shapiro et al. |
| 5,647,871 A | 7/1997 | Levine et al. |
| 5,651,780 A | 7/1997 | Jackson et al. |
| 5,653,677 A | 8/1997 | Okada et al. |
| 5,653,713 A | 8/1997 | Michelson |
| 5,657,697 A | 8/1997 | Murai |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,681,260 A | 10/1997 | Ueda et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,700,243 A | 12/1997 | Narciso, Jr. |
| 5,700,261 A | 12/1997 | Brinkerhoff |
| 5,704,900 A | 1/1998 | Dobrovolny et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,722,326 A | 3/1998 | Post |
| 5,722,426 A | 3/1998 | Kolff |
| 5,732,636 A | 3/1998 | Wang et al. |
| 5,733,074 A | 3/1998 | Stock et al. |
| 5,735,848 A | 4/1998 | Yates et al. |
| 5,738,652 A | 4/1998 | Boyd et al. |
| 5,741,226 A | 4/1998 | Strukel et al. |
| 5,741,305 A | 4/1998 | Vincent et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,776,130 A | 7/1998 | Buysse et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,718 A | 9/1998 | Akiba et al. |
| 5,810,811 A | 9/1998 | Yates et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman et al. |
| 5,828,160 A | 10/1998 | Sugishita |
| 5,836,867 A | 11/1998 | Speier et al. |
| 5,836,909 A | 11/1998 | Cosmescu |
| 5,836,943 A | 11/1998 | Miller, III |
| 5,836,990 A | 11/1998 | Li |
| 5,843,109 A | 12/1998 | Mehta et al. |
| 5,853,412 A | 12/1998 | Mayenberger |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,454 A | 3/1999 | Hones et al. |

(56) References Cited

U.S. PATENT DOCUMENTS

| | | |
|---|---|---|
| 5,887,018 A | 3/1999 | Bayazitoglu et al. |
| 5,891,142 A | 4/1999 | Eggers et al. |
| 5,893,835 A | 4/1999 | Witt et al. |
| 5,897,569 A | 4/1999 | Kellogg et al. |
| 5,902,239 A | 5/1999 | Buurman |
| 5,904,147 A | 5/1999 | Conlan et al. |
| 5,906,579 A | 5/1999 | Vander Salm et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,298 A | 8/1999 | Koike |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,849 A | 9/1999 | Munro |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,984,938 A | 11/1999 | Yoon |
| 5,989,182 A | 11/1999 | Hori et al. |
| 5,989,274 A | 11/1999 | Davison et al. |
| 5,989,275 A | 11/1999 | Estabrook et al. |
| 5,993,972 A | 11/1999 | Reich et al. |
| 6,003,517 A | 12/1999 | Sheffield et al. |
| 6,007,484 A | 12/1999 | Thompson |
| 6,013,052 A | 1/2000 | Durman et al. |
| 6,014,580 A | 1/2000 | Blume et al. |
| 6,024,741 A | 2/2000 | Williamson, IV et al. |
| 6,024,744 A | 2/2000 | Kese et al. |
| 6,033,375 A | 3/2000 | Brumbach |
| 6,033,399 A | 3/2000 | Gines |
| 6,039,734 A | 3/2000 | Goble |
| 6,050,996 A | 4/2000 | Schmaltz et al. |
| 6,053,172 A | 4/2000 | Hovda et al. |
| 6,063,098 A | 5/2000 | Houser et al. |
| 6,066,132 A | 5/2000 | Chen et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,152 A | 6/2000 | Nardella et al. |
| 6,083,151 A | 7/2000 | Renner et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,099,483 A | 8/2000 | Palmer et al. |
| 6,099,550 A | 8/2000 | Yoon |
| 6,109,500 A | 8/2000 | Alli et al. |
| 6,113,594 A | 9/2000 | Savage |
| 6,113,598 A | 9/2000 | Baker |
| 6,123,466 A | 9/2000 | Persson et al. |
| H1904 H | 10/2000 | Yates et al. |
| 6,127,757 A | 10/2000 | Swinbanks |
| 6,132,368 A | 10/2000 | Cooper |
| 6,139,320 A | 10/2000 | Hahn |
| 6,144,402 A | 11/2000 | Norsworthy et al. |
| 6,152,902 A | 11/2000 | Christian et al. |
| 6,152,923 A | 11/2000 | Ryan |
| 6,154,198 A | 11/2000 | Rosenberg |
| 6,159,160 A | 12/2000 | Hsei et al. |
| 6,159,175 A | 12/2000 | Strukel et al. |
| 6,162,208 A | 12/2000 | Hipps |
| 6,173,199 B1 | 1/2001 | Gabriel |
| 6,173,715 B1 | 1/2001 | Sinanan et al. |
| 6,174,309 B1 | 1/2001 | Wrublewski et al. |
| 6,176,857 B1 | 1/2001 | Ashley |
| 6,190,386 B1 | 2/2001 | Rydell |
| 6,206,844 B1 | 3/2001 | Reichel et al. |
| 6,206,876 B1 | 3/2001 | Levine et al. |
| 6,206,877 B1 | 3/2001 | Kese et al. |
| 6,210,403 B1 | 4/2001 | Klicek |
| 6,214,023 B1 | 4/2001 | Whipple et al. |
| 6,219,572 B1 | 4/2001 | Young |
| 6,221,007 B1 | 4/2001 | Green |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,248,074 B1 | 6/2001 | Ohno et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,258,086 B1 | 7/2001 | Ashley et al. |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,273,887 B1 | 8/2001 | Yamauchi et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,283,981 B1 | 9/2001 | Beaupre |
| 6,292,700 B1 | 9/2001 | Morrison et al. |
| 6,309,400 B2 | 10/2001 | Beaupre |
| 6,315,789 B1 | 11/2001 | Cragg |
| 6,319,221 B1 | 11/2001 | Savage et al. |
| 6,325,799 B1 | 12/2001 | Goble |
| 6,325,811 B1 | 12/2001 | Messerly |
| 6,328,751 B1 | 12/2001 | Beaupre |
| 6,340,878 B1 | 1/2002 | Oglesbee |
| 6,352,532 B1 | 3/2002 | Kramer et al. |
| 6,364,888 B1 | 4/2002 | Niemeyer et al. |
| 6,371,952 B1 | 4/2002 | Madhani et al. |
| 6,379,320 B1 | 4/2002 | Lafon et al. |
| D457,958 S | 5/2002 | Dycus et al. |
| 6,383,194 B1 | 5/2002 | Pothula |
| 6,387,094 B1 | 5/2002 | Eitenmuller |
| 6,387,109 B1 | 5/2002 | Davison et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,443,968 B1 | 9/2002 | Holthaus et al. |
| 6,443,969 B1 | 9/2002 | Novak et al. |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,464,703 B2 | 10/2002 | Bartel |
| 6,471,172 B1 | 10/2002 | Lemke et al. |
| 6,475,211 B2 | 11/2002 | Chess et al. |
| 6,475,216 B2 | 11/2002 | Mulier et al. |
| 6,480,796 B2 | 11/2002 | Wiener |
| 6,485,490 B2 | 11/2002 | Wampler et al. |
| 6,491,690 B1 | 12/2002 | Goble et al. |
| 6,491,691 B1 | 12/2002 | Morley et al. |
| 6,491,701 B2 | 12/2002 | Tierney et al. |
| 6,491,708 B2 | 12/2002 | Madan et al. |
| 6,497,715 B2 | 12/2002 | Satou |

(56) References Cited

U.S. PATENT DOCUMENTS

| | | |
|---|---|---|
| 6,500,112 B1 | 12/2002 | Khouri |
| 6,500,176 B1 | 12/2002 | Truckai et al. |
| 6,500,188 B2 | 12/2002 | Harper et al. |
| 6,503,248 B1 | 1/2003 | Levine |
| 6,506,208 B2 | 1/2003 | Hunt et al. |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,520,960 B2 | 2/2003 | Blocher et al. |
| 6,522,909 B1 | 2/2003 | Garibaldi et al. |
| 6,524,316 B1 | 2/2003 | Nicholson et al. |
| 6,531,846 B1 | 3/2003 | Smith |
| 6,533,784 B2 | 3/2003 | Truckai et al. |
| 6,537,196 B1 | 3/2003 | Creighton, IV et al. |
| 6,537,272 B2 | 3/2003 | Christopherson et al. |
| 6,537,291 B2 | 3/2003 | Friedman et al. |
| 6,540,693 B2 | 4/2003 | Burbank et al. |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,037 B2 | 5/2003 | Paton et al. |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,589,239 B2 | 7/2003 | Khandkar et al. |
| 6,594,517 B1 | 7/2003 | Nevo |
| 6,599,321 B2 | 7/2003 | Hyde, Jr. |
| 6,602,252 B2 | 8/2003 | Mollenauer |
| 6,610,060 B2 | 8/2003 | Mulier et al. |
| 6,616,450 B2 | 9/2003 | Mossle et al. |
| 6,616,600 B2 | 9/2003 | Pauker |
| 6,619,529 B2 | 9/2003 | Green et al. |
| 6,620,129 B2 | 9/2003 | Stecker et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,817 B2 | 11/2003 | Schara et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,663,941 B2 | 12/2003 | Brown et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,695,840 B2 | 2/2004 | Schulze |
| 6,716,215 B1 | 4/2004 | David et al. |
| 6,719,684 B2 | 4/2004 | Kim et al. |
| 6,719,765 B2 | 4/2004 | Bonutti |
| 6,722,552 B2 | 4/2004 | Fenton, Jr. |
| 6,726,686 B2 | 4/2004 | Buysse et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,743,229 B2 | 6/2004 | Buysse et al. |
| 6,746,443 B1 | 6/2004 | Morley et al. |
| 6,752,815 B2 | 6/2004 | Beaupre |
| 6,762,535 B2 | 7/2004 | Take et al. |
| 6,766,202 B2 | 7/2004 | Underwood et al. |
| 6,767,349 B2 | 7/2004 | Ouchi |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,165 B2 | 8/2004 | Jin |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,216 B1 | 9/2004 | Ishikawa |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,806,317 B2 | 10/2004 | Morishita et al. |
| 6,808,491 B2 | 10/2004 | Kortenbach et al. |
| 6,811,842 B1 | 11/2004 | Ehrnsperger et al. |
| 6,814,731 B2 | 11/2004 | Swanson |
| 6,817,974 B2 | 11/2004 | Cooper et al. |
| 6,821,273 B2 | 11/2004 | Mollenauer |
| 6,828,712 B2 | 12/2004 | Battaglin et al. |
| 6,832,998 B2 | 12/2004 | Goble |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,869,439 B2 | 3/2005 | White et al. |
| 6,875,220 B2 | 4/2005 | Du et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,632 B2 | 8/2005 | Nita et al. |
| 6,929,644 B2 | 8/2005 | Truckai et al. |
| 6,936,003 B2 | 8/2005 | Iddan |
| D509,589 S | 9/2005 | Wells |
| 6,939,347 B2 | 9/2005 | Thompson |
| 6,945,981 B2 | 9/2005 | Donofrio et al. |
| 6,953,461 B2 | 10/2005 | McClurken et al. |
| D511,145 S | 11/2005 | Donofrio et al. |
| 6,959,852 B2 | 11/2005 | Shelton, IV et al. |
| 6,974,462 B2 | 12/2005 | Sater |
| 6,976,844 B2 | 12/2005 | Hickok et al. |
| 6,976,969 B2 | 12/2005 | Messerly |
| 6,977,495 B2 | 12/2005 | Donofrio |
| 6,984,220 B2 | 1/2006 | Wuchinich |
| 6,986,738 B2 | 1/2006 | Glukhovsky et al. |
| 6,986,780 B2 | 1/2006 | Rudnick et al. |
| 6,994,709 B2 | 2/2006 | Iida |
| 7,000,818 B2 | 2/2006 | Shelton, IV et al. |
| 7,004,951 B2 | 2/2006 | Gibbens, III |
| 7,011,657 B2 | 3/2006 | Truckai et al. |
| 7,029,435 B2 | 4/2006 | Nakao |
| 7,039,453 B2 | 5/2006 | Mullick et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,352 B2 | 5/2006 | Shelton, IV et al. |
| 7,044,937 B1 | 5/2006 | Kirwan et al. |
| 7,052,496 B2 | 5/2006 | Yamauchi |
| 7,055,731 B2 | 6/2006 | Shelton, IV et al. |
| 7,056,284 B2 | 6/2006 | Martone et al. |
| 7,063,699 B2 | 6/2006 | Hess et al. |
| 7,066,879 B2 | 6/2006 | Fowler et al. |
| 7,066,936 B2 | 6/2006 | Ryan |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,579 B2 | 8/2006 | Yokoi et al. |
| 7,083,617 B2 | 8/2006 | Kortenbach et al. |
| 7,083,618 B2 | 8/2006 | Couture et al. |

(56) References Cited

U.S. PATENT DOCUMENTS

| | | |
|---|---|---|
| 7,083,619 B2 | 8/2006 | Truckai et al. |
| 7,087,054 B2 | 8/2006 | Truckai et al. |
| 7,090,673 B2 | 8/2006 | Dycus et al. |
| 7,094,235 B2 | 8/2006 | Francischelli |
| 7,096,560 B2 | 8/2006 | Oddsen, Jr. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,118,570 B2 | 10/2006 | Tetzlaff et al. |
| 7,120,498 B2 | 10/2006 | Imran et al. |
| 7,124,932 B2 | 10/2006 | Isaacson et al. |
| 7,125,409 B2 | 10/2006 | Truckai et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,147,638 B2 | 12/2006 | Chapman et al. |
| 7,153,315 B2 | 12/2006 | Miller |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,298 B2 | 1/2007 | Lawes et al. |
| 7,163,548 B2 | 1/2007 | Stulen et al. |
| 7,169,104 B2 | 1/2007 | Ueda et al. |
| 7,169,146 B2 | 1/2007 | Truckai et al. |
| 7,169,156 B2 | 1/2007 | Hart |
| 7,170,823 B2 | 1/2007 | Fabricius et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,199,545 B2 | 4/2007 | Oleynikov et al. |
| 7,204,820 B2 | 4/2007 | Akahoshi |
| 7,207,471 B2 | 4/2007 | Heinrich et al. |
| 7,208,005 B2 | 4/2007 | Frecker et al. |
| 7,211,094 B2 | 5/2007 | Gannoe et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,064 B2 | 6/2007 | Hopper et al. |
| 7,235,073 B2 | 6/2007 | Levine et al. |
| 7,241,290 B2 | 7/2007 | Doyle et al. |
| 7,241,294 B2 | 7/2007 | Reschke |
| 7,241,296 B2 | 7/2007 | Buysse et al. |
| 7,246,734 B2 | 7/2007 | Shelton, IV |
| 7,251,531 B2 | 7/2007 | Mosher et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,267,685 B2 | 9/2007 | Butaric et al. |
| 7,270,664 B2 | 9/2007 | Johnson et al. |
| 7,273,483 B2 | 9/2007 | Wiener et al. |
| 7,276,065 B2 | 10/2007 | Morley et al. |
| 7,282,773 B2 | 10/2007 | Li et al. |
| 7,287,682 B1 | 10/2007 | Ezzat et al. |
| 7,297,145 B2 | 11/2007 | Woloszko et al. |
| 7,297,149 B2 | 11/2007 | Vitali et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,360,542 B2 | 4/2008 | Nelson et al. |
| 7,364,577 B2 | 4/2008 | Wham et al. |
| 7,367,973 B2 | 5/2008 | Manzo et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,416,101 B2 | 8/2008 | Shelton, IV et al. |
| D576,725 S | 9/2008 | Shumer et al. |
| 7,422,139 B2 | 9/2008 | Shelton, IV et al. |
| 7,422,586 B2 | 9/2008 | Morris et al. |
| 7,422,592 B2 | 9/2008 | Morley et al. |
| 7,429,259 B2 | 9/2008 | Cadeddu et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,435,249 B2 | 10/2008 | Buysse et al. |
| 7,435,582 B2 | 10/2008 | Zimmermann et al. |
| 7,439,732 B2 | 10/2008 | LaPlaca |
| 7,441,684 B2 | 10/2008 | Shelton, IV et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,448,993 B2 | 11/2008 | Yokoi et al. |
| 7,449,004 B2 | 11/2008 | Yamada et al. |
| 7,450,998 B2 | 11/2008 | Zilberman et al. |
| 7,451,904 B2 | 11/2008 | Shelton, IV |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,479,148 B2 | 1/2009 | Beaupre |
| 7,479,160 B2 | 1/2009 | Branch et al. |
| 7,487,899 B2 | 2/2009 | Shelton, IV et al. |
| 7,488,319 B2 | 2/2009 | Yates |
| 7,491,201 B2 | 2/2009 | Shields et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,503,893 B2 | 3/2009 | Kucklick |
| 7,505,812 B1 | 3/2009 | Eggers et al. |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,511,733 B2 | 3/2009 | Takizawa et al. |
| 7,513,025 B2 | 4/2009 | Fischer |
| 7,517,349 B2 | 4/2009 | Truckai et al. |
| 7,520,877 B2 | 4/2009 | Lee, Jr. et al. |
| 7,524,320 B2 | 4/2009 | Tierney et al. |
| 7,534,243 B1 | 5/2009 | Chin et al. |
| D594,983 S | 6/2009 | Price et al. |
| 7,540,872 B2 | 6/2009 | Schechter et al. |
| 7,543,730 B1 | 6/2009 | Marczyk |
| 7,544,200 B2 | 6/2009 | Houser |
| 7,550,216 B2 | 6/2009 | Ofer et al. |
| 7,553,309 B2 | 6/2009 | Buysse et al. |
| 7,559,452 B2 | 7/2009 | Wales et al. |
| 7,566,318 B2 | 7/2009 | Haefner |
| 7,567,012 B2 | 7/2009 | Namikawa |
| 7,582,086 B2 | 9/2009 | Privitera et al. |
| 7,582,087 B2 | 9/2009 | Tetzlaff et al. |
| 7,586,289 B2 | 9/2009 | Andruk et al. |
| 7,588,176 B2 | 9/2009 | Timm et al. |
| 7,588,177 B2 | 9/2009 | Racenet |

(56) References Cited

U.S. PATENT DOCUMENTS

| | | |
|---|---|---|
| 7,594,925 B2 | 9/2009 | Danek et al. |
| 7,597,693 B2 | 10/2009 | Garrison |
| 7,599,743 B2 | 10/2009 | Hassler, Jr. et al. |
| 7,601,119 B2 | 10/2009 | Shahinian |
| 7,604,150 B2 | 10/2009 | Boudreaux |
| 7,611,512 B2 | 11/2009 | Ein-Gal |
| 7,617,961 B2 | 11/2009 | Viola |
| 7,621,910 B2 | 11/2009 | Sugi |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,640,447 B2 | 12/2009 | Qiu |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,678,043 B2 | 3/2010 | Gilad |
| 7,678,105 B2 | 3/2010 | McGreevy et al. |
| 7,686,804 B2 | 3/2010 | Johnson et al. |
| 7,691,095 B2 | 4/2010 | Bednarek et al. |
| 7,691,098 B2 | 4/2010 | Wallace et al. |
| 7,691,103 B2 | 4/2010 | Fernandez et al. |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,717,312 B2 | 5/2010 | Beetel |
| 7,717,914 B2 | 5/2010 | Kimura |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,725,214 B2 | 5/2010 | Diolaiti |
| D618,797 S | 6/2010 | Price et al. |
| 7,726,537 B2 | 6/2010 | Olson et al. |
| 7,744,615 B2 | 6/2010 | Couture |
| 7,751,115 B2 | 7/2010 | Song |
| 7,753,904 B2 | 7/2010 | Shelton, IV et al. |
| 7,753,908 B2 | 7/2010 | Swanson |
| 7,753,909 B2 | 7/2010 | Chapman et al. |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,775,972 B2 | 8/2010 | Brock et al. |
| 7,776,036 B2 | 8/2010 | Schechter et al. |
| 7,776,037 B2 | 8/2010 | Odom |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,663 B2 | 8/2010 | Shelton, IV |
| 7,789,283 B2 | 9/2010 | Shah |
| 7,789,878 B2 | 9/2010 | Dumbauld et al. |
| 7,789,883 B2 | 9/2010 | Takashino et al. |
| 7,793,814 B2 | 9/2010 | Racenet et al. |
| 7,799,027 B2 | 9/2010 | Hafner |
| 7,803,156 B2 | 9/2010 | Eder et al. |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| D627,066 S | 11/2010 | Romero |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,837,699 B2 | 11/2010 | Yamada et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,850,688 B2 | 12/2010 | Hafner |
| D631,155 S | 1/2011 | Peine et al. |
| 7,861,906 B2 | 1/2011 | Doll et al. |
| 7,862,560 B2 | 1/2011 | Marion |
| 7,867,228 B2 | 1/2011 | Nobis et al. |
| 7,871,392 B2 | 1/2011 | Sartor |
| 7,871,423 B2 | 1/2011 | Livneh |
| D631,965 S | 2/2011 | Price et al. |
| 7,877,852 B2 | 2/2011 | Unger et al. |
| 7,877,853 B2 | 2/2011 | Unger et al. |
| 7,879,035 B2 | 2/2011 | Garrison et al. |
| 7,879,070 B2 | 2/2011 | Ortiz et al. |
| 7,892,606 B2 | 2/2011 | Thies et al. |
| 7,896,875 B2 | 3/2011 | Heim et al. |
| 7,896,878 B2 | 3/2011 | Johnson et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,922,953 B2 | 4/2011 | Guerra |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,942,303 B2 | 5/2011 | Shah |
| 7,942,868 B2 | 5/2011 | Cooper |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,976,544 B2 | 7/2011 | McClurken et al. |
| 7,980,443 B2 | 7/2011 | Scheib et al. |
| 7,981,113 B2 | 7/2011 | Truckai et al. |
| 7,988,567 B2 | 8/2011 | Kim et al. |
| 7,997,278 B2 | 8/2011 | Utley et al. |
| 8,020,743 B2 | 9/2011 | Shelton, IV |
| 8,033,173 B2 | 10/2011 | Ehlert et al. |
| 8,038,612 B2 | 10/2011 | Paz |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,056,787 B2 | 11/2011 | Boudreaux et al. |
| 8,057,498 B2 | 11/2011 | Robertson |
| 8,058,771 B2 | 11/2011 | Giordano et al. |
| 8,061,014 B2 | 11/2011 | Smith et al. |
| 8,062,211 B2 | 11/2011 | Duval et al. |
| 8,066,167 B2 | 11/2011 | Measamer et al. |
| 8,070,036 B1 | 12/2011 | Knodel |
| 8,070,748 B2 | 12/2011 | Hixson et al. |
| 8,075,555 B2 | 12/2011 | Truckai et al. |
| 8,075,558 B2 | 12/2011 | Truckai et al. |
| 8,092,475 B2 | 1/2012 | Cotter et al. |
| 8,100,894 B2 | 1/2012 | Mucko et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,114,119 B2 | 2/2012 | Spivey et al. |
| 8,128,624 B2 | 3/2012 | Couture et al. |
| 8,128,657 B2 | 3/2012 | Shiono et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,461 B2 | 3/2012 | Houser et al. |
| 8,147,488 B2 | 4/2012 | Masuda |

(56) References Cited

U.S. PATENT DOCUMENTS

| | | |
|---|---|---|
| 8,147,508 B2 | 4/2012 | Madan et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,940 B2 | 4/2012 | Johnson et al. |
| 8,177,794 B2 | 5/2012 | Cabrera et al. |
| 8,182,502 B2 | 5/2012 | Stulen et al. |
| 8,186,560 B2 | 5/2012 | Hess et al. |
| 8,187,166 B2 | 5/2012 | Kuth et al. |
| 8,187,267 B2 | 5/2012 | Pappone et al. |
| 8,192,433 B2 | 6/2012 | Johnson et al. |
| 8,197,472 B2 | 6/2012 | Lau et al. |
| 8,197,479 B2 | 6/2012 | Olson et al. |
| 8,197,494 B2 | 6/2012 | Jaggi et al. |
| 8,197,502 B2 | 6/2012 | Smith et al. |
| 8,206,212 B2 | 6/2012 | Iddings et al. |
| 8,221,415 B2 | 7/2012 | Francischelli |
| 8,226,675 B2 | 7/2012 | Houser et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,283 B2 | 8/2012 | Guerra et al. |
| 8,241,312 B2 | 8/2012 | Messerly |
| 8,244,368 B2 | 8/2012 | Sherman |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,252,012 B2 | 8/2012 | Stulen |
| 8,257,352 B2 | 9/2012 | Lawes et al. |
| 8,257,377 B2 | 9/2012 | Wiener et al. |
| 8,262,563 B2 | 9/2012 | Bakos et al. |
| 8,267,300 B2 | 9/2012 | Boudreaux |
| 8,267,854 B2 | 9/2012 | Asada et al. |
| 8,267,935 B2 | 9/2012 | Couture et al. |
| 8,273,085 B2 | 9/2012 | Park et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,292,888 B2 | 10/2012 | Whitman |
| 8,298,228 B2 | 10/2012 | Buysse et al. |
| 8,298,232 B2 | 10/2012 | Unger |
| 8,303,583 B2 | 11/2012 | Hosier et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,322,455 B2 | 12/2012 | Shelton, IV et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,158 B2 | 1/2013 | McKenna et al. |
| 8,361,569 B2 | 1/2013 | Saito et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,053 B2 | 2/2013 | Orszulak |
| 8,377,059 B2 | 2/2013 | Deville et al. |
| 8,377,085 B2 | 2/2013 | Smith et al. |
| 8,382,754 B2 | 2/2013 | Odom et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,094 B2 | 3/2013 | Edwards et al. |
| 8,394,115 B2 | 3/2013 | Houser et al. |
| 8,397,971 B2 | 3/2013 | Yates et al. |
| 8,403,926 B2 | 3/2013 | Nobis et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,076 B2 | 4/2013 | Pang et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,956 B2 | 6/2013 | McKenna et al. |
| 8,469,981 B2 | 6/2013 | Robertson et al. |
| 8,475,361 B2 | 7/2013 | Barlow et al. |
| 8,475,453 B2 | 7/2013 | Marczyk et al. |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,625 B2 | 7/2013 | Horner |
| 8,496,682 B2 | 7/2013 | Guerra et al. |
| 8,512,336 B2 | 8/2013 | Couture |
| 8,512,364 B2 | 8/2013 | Kowalski et al. |
| 8,512,365 B2 | 8/2013 | Wiener et al. |
| 8,523,889 B2 | 9/2013 | Stulen et al. |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,542,501 B2 | 9/2013 | Kyono |
| 8,553,430 B2 | 10/2013 | Melanson et al. |
| 8,562,516 B2 | 10/2013 | Saadat et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,187 B2 | 11/2013 | Marion |
| 8,574,231 B2 | 11/2013 | Boudreaux et al. |
| 8,579,176 B2 | 11/2013 | Smith et al. |
| 8,579,928 B2 | 11/2013 | Robertson et al. |
| 8,579,937 B2 | 11/2013 | Gresham |
| 8,591,459 B2 | 11/2013 | Clymer et al. |
| 8,591,506 B2 | 11/2013 | Wham et al. |
| D695,407 S | 12/2013 | Price et al. |
| 8,596,513 B2 | 12/2013 | Olson et al. |
| 8,597,182 B2 | 12/2013 | Stein et al. |
| 8,597,297 B2 | 12/2013 | Couture et al. |
| 8,608,044 B2 | 12/2013 | Hueil et al. |
| 8,613,383 B2 | 12/2013 | Beckman et al. |
| 8,622,274 B2 | 1/2014 | Yates et al. |

(56) References Cited

U.S. PATENT DOCUMENTS

| | | |
|---|---|---|
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,632,539 B2 | 1/2014 | Twomey et al. |
| 8,636,648 B2 | 1/2014 | Gazdzinski |
| 8,636,736 B2 | 1/2014 | Yates et al. |
| 8,636,761 B2 | 1/2014 | Cunningham et al. |
| 8,638,428 B2 | 1/2014 | Brown |
| 8,640,788 B2 | 2/2014 | Dachs, II et al. |
| 8,641,712 B2 | 2/2014 | Couture |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,155 B2 | 2/2014 | Houser et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,668,691 B2 | 3/2014 | Heard |
| RE44,834 E | 4/2014 | Dumbauld et al. |
| 8,684,253 B2 | 4/2014 | Giordano et al. |
| 8,685,020 B2 | 4/2014 | Weizman et al. |
| 8,685,056 B2 | 4/2014 | Evans et al. |
| 8,696,662 B2 | 4/2014 | Eder et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,708,213 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,758,342 B2 | 6/2014 | Bales et al. |
| 8,764,747 B2 | 7/2014 | Cummings et al. |
| 8,770,459 B2 | 7/2014 | Racenet et al. |
| 8,784,418 B2 | 7/2014 | Romero |
| 8,789,740 B2 | 7/2014 | Baxter, III et al. |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,752 B2 | 8/2014 | Fortier et al. |
| 8,808,319 B2 | 8/2014 | Houser et al. |
| 8,814,856 B2 | 8/2014 | Elmouelhi et al. |
| 8,814,865 B2 | 8/2014 | Reschke |
| 8,814,870 B2 | 8/2014 | Paraschiv et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,488 B2 | 9/2014 | Farritor et al. |
| 8,834,518 B2 | 9/2014 | Faller et al. |
| 8,845,630 B2 | 9/2014 | Mehta et al. |
| 8,851,354 B2 | 10/2014 | Swensgard et al. |
| 8,852,184 B2 | 10/2014 | Kucklick |
| 8,864,757 B2 | 10/2014 | Klimovitch et al. |
| 8,864,761 B2 | 10/2014 | Johnson et al. |
| 8,870,867 B2 | 10/2014 | Walberg et al. |
| 8,876,858 B2 | 11/2014 | Braun |
| 8,882,766 B2 | 11/2014 | Couture et al. |
| 8,882,791 B2 | 11/2014 | Stulen |
| 8,887,373 B2 | 11/2014 | Brandt et al. |
| 8,888,776 B2 | 11/2014 | Dietz et al. |
| 8,888,783 B2 | 11/2014 | Young |
| 8,888,809 B2 | 11/2014 | Davison et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,926,607 B2 | 1/2015 | Norvell et al. |
| 8,926,608 B2 | 1/2015 | Bacher et al. |
| 8,929,888 B2 | 1/2015 | Rao et al. |
| 8,931,682 B2 | 1/2015 | Timm et al. |
| 8,939,287 B2 | 1/2015 | Markovitch |
| 8,939,974 B2 | 1/2015 | Boudreaux et al. |
| 8,939,975 B2 | 1/2015 | Twomey et al. |
| 8,944,997 B2 | 2/2015 | Fernandez et al. |
| 8,945,125 B2 | 2/2015 | Schechter et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,968,276 B2 | 3/2015 | Zemlok et al. |
| 8,968,308 B2 | 3/2015 | Horner et al. |
| 8,968,312 B2 | 3/2015 | Marczyk et al. |
| 8,968,332 B2 | 3/2015 | Farritor et al. |
| 8,978,845 B2 | 3/2015 | Kim |
| 8,979,838 B2 | 3/2015 | Woloszko et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,989,855 B2 | 3/2015 | Murphy et al. |
| 8,992,422 B2 | 3/2015 | Spivey et al. |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,017,326 B2 | 4/2015 | DiNardo et al. |
| 9,017,372 B2 | 4/2015 | Artale et al. |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,983 B2 | 5/2015 | Takashino et al. |
| 9,039,695 B2 | 5/2015 | Giordano et al. |
| 9,039,705 B2 | 5/2015 | Takashino |
| 9,039,731 B2 | 5/2015 | Joseph |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,055,961 B2 | 6/2015 | Manzo et al. |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,078,664 B2 | 7/2015 | Palmer et al. |
| 9,089,327 B2 | 7/2015 | Worrell et al. |
| 9,089,360 B2 | 7/2015 | Messerly et al. |
| 9,094,006 B2 | 7/2015 | Gravati et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,672 B2 | 8/2015 | Tetzlaff et al. |
| 9,113,889 B2 | 8/2015 | Reschke |
| 9,113,900 B2 | 8/2015 | Buysse et al. |
| 9,119,630 B2 | 9/2015 | Townsend et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,138,289 B2 | 9/2015 | Conley et al. |
| 9,149,324 B2 | 10/2015 | Huang et al. |
| 9,149,325 B2 | 10/2015 | Worrell et al. |
| 9,155,585 B2 | 10/2015 | Bales, Jr. et al. |
| 9,161,803 B2 | 10/2015 | Yates et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,179,912 B2 | 11/2015 | Yates et al. |

(56) References Cited

U.S. PATENT DOCUMENTS

| | | |
|---|---|---|
| 9,186,204 B2 | 11/2015 | Nishimura et al. |
| 9,187,758 B2 | 11/2015 | Cai et al. |
| 9,192,380 B2 | 11/2015 | (Tarinelli) Racenet et al. |
| 9,192,421 B2 | 11/2015 | Garrison |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,716 B2 | 12/2015 | Masuda et al. |
| 9,204,879 B2 | 12/2015 | Shelton, IV |
| 9,204,919 B2 | 12/2015 | Brandt et al. |
| 9,216,050 B2 | 12/2015 | Condie et al. |
| 9,220,559 B2 | 12/2015 | Worrell et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,571 B2 | 2/2016 | Twomey et al. |
| 9,265,926 B2 | 2/2016 | Strobl et al. |
| 9,271,784 B2 | 3/2016 | Evans et al. |
| 9,274,988 B2 | 3/2016 | Hsu et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,308,014 B2 | 4/2016 | Fischer |
| 9,314,292 B2 | 4/2016 | Trees et al. |
| 9,326,788 B2 | 5/2016 | Batross et al. |
| 9,326,812 B2 | 5/2016 | Waaler et al. |
| 9,333,025 B2 | 5/2016 | Monson et al. |
| 9,339,323 B2 | 5/2016 | Eder et al. |
| 9,339,326 B2 | 5/2016 | McCullagh et al. |
| 9,344,042 B2 | 5/2016 | Mao |
| 9,345,481 B2 | 5/2016 | Hall et al. |
| 9,345,900 B2 | 5/2016 | Wu et al. |
| 9,351,754 B2 | 5/2016 | Vakharia et al. |
| 9,358,065 B2 | 6/2016 | Ladtkow et al. |
| 9,364,230 B2 | 6/2016 | Shelton, IV et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,381,060 B2 | 7/2016 | Artale et al. |
| 9,386,983 B2 | 7/2016 | Swensgard et al. |
| 9,393,037 B2 | 7/2016 | Olson et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,456,876 B2 | 10/2016 | Hagn |
| 9,492,224 B2 | 11/2016 | Boudreaux et al. |
| 9,504,524 B2 | 11/2016 | Behnke, II |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,549,663 B2 | 1/2017 | Larkin |
| 9,554,845 B2 | 1/2017 | Arts |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,585,709 B2 | 3/2017 | Krapohl |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,810 B2 | 4/2017 | Hart et al. |
| 9,627,120 B2 | 4/2017 | Scott et al. |
| 9,629,629 B2 | 4/2017 | Leimbach et al. |
| 9,642,669 B2 | 5/2017 | Takashino et al. |
| 9,649,111 B2 | 5/2017 | Shelton, IV et al. |
| 9,649,144 B2 | 5/2017 | Aluru et al. |
| 9,649,151 B2 | 5/2017 | Goodman et al. |
| 9,662,131 B2 | 5/2017 | Omori et al. |
| 9,668,806 B2 | 6/2017 | Unger et al. |
| 9,700,339 B2 | 7/2017 | Nield |
| 9,707,005 B2 | 7/2017 | Strobl et al. |
| 9,707,027 B2 | 7/2017 | Ruddenklau et al. |
| 9,707,030 B2 | 7/2017 | Davison et al. |
| 9,724,118 B2 | 8/2017 | Schulte et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,757,128 B2 | 9/2017 | Baber et al. |
| 9,757,142 B2 | 9/2017 | Shimizu |
| 9,757,186 B2 | 9/2017 | Boudreaux et al. |
| 9,782,214 B2 | 10/2017 | Houser et al. |
| 9,782,220 B2 | 10/2017 | Mark et al. |
| 9,795,436 B2 | 10/2017 | Yates et al. |
| 9,802,033 B2 | 10/2017 | Hibner et al. |
| 9,808,244 B2 | 11/2017 | Leimbach et al. |
| 9,808,308 B2 | 11/2017 | Faller et al. |
| 9,814,460 B2 | 11/2017 | Kimsey et al. |
| 9,820,768 B2 | 11/2017 | Gee et al. |
| 9,820,771 B2 | 11/2017 | Norton et al. |
| 9,833,239 B2 | 12/2017 | Yates et al. |
| 9,848,937 B2 | 12/2017 | Trees et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,888,958 B2 | 2/2018 | Evans et al. |
| 9,907,563 B2 | 3/2018 | Germain et al. |
| 9,913,680 B2 | 3/2018 | Voegele et al. |
| 9,918,730 B2 | 3/2018 | Trees et al. |
| 9,949,620 B2 | 4/2018 | Duval et al. |
| 9,949,785 B2 | 4/2018 | Price et al. |
| 9,949,788 B2 | 4/2018 | Boudreaux |
| 9,974,539 B2 | 5/2018 | Yates et al. |
| 9,993,289 B2 | 6/2018 | Sobajima et al. |
| 10,010,339 B2 | 7/2018 | Witt et al. |
| 10,016,207 B2 | 7/2018 | Suzuki et al. |
| 10,022,142 B2 | 7/2018 | Aranyi et al. |
| 10,041,822 B2 | 8/2018 | Zemlok |
| 10,052,044 B2 | 8/2018 | Shelton, IV et al. |
| 10,070,916 B2 | 9/2018 | Artale |
| 10,092,310 B2 | 10/2018 | Boudreaux et al. |
| 10,092,348 B2 | 10/2018 | Boudreaux |
| 10,092,350 B2 | 10/2018 | Rothweiler et al. |
| 10,105,174 B2 | 10/2018 | Krapohl |
| 10,111,699 B2 | 10/2018 | Boudreaux |
| 10,117,702 B2 | 11/2018 | Danziger et al. |
| 10,130,410 B2 | 11/2018 | Strobl et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,194,911 B2 | 2/2019 | Miller et al. |
| 10,194,972 B2 | 2/2019 | Yates et al. |
| 10,194,976 B2 | 2/2019 | Boudreaux |
| 10,194,977 B2 | 2/2019 | Yang |
| 10,211,586 B2 | 2/2019 | Adams et al. |
| 10,245,095 B2 | 4/2019 | Boudreaux |
| 10,265,118 B2 | 4/2019 | Gerhardt |
| 10,278,721 B2 | 5/2019 | Dietz et al. |
| 10,314,638 B2 | 6/2019 | Gee et al. |
| 10,321,950 B2 | 6/2019 | Yates et al. |
| 10,342,602 B2 | 7/2019 | Strobl et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0049551 A1 | 4/2002 | Friedman et al. |
| 2002/0077550 A1 | 6/2002 | Rabiner et al. |
| 2002/0095175 A1 | 7/2002 | Brock et al. |
| 2002/0107517 A1 | 8/2002 | Witt et al. |

(56) References Cited

U.S. PATENT DOCUMENTS

| | | |
|---|---|---|
| 2002/0156493 A1 | 10/2002 | Houser et al. |
| 2003/0014053 A1 | 1/2003 | Nguyen et al. |
| 2003/0055443 A1 | 3/2003 | Spotnitz |
| 2003/0066938 A1 | 4/2003 | Zimmerman |
| 2003/0109875 A1 | 6/2003 | Tetzlaff et al. |
| 2003/0114731 A1 | 6/2003 | Cadeddu et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0204199 A1 | 10/2003 | Novak et al. |
| 2003/0212332 A1 | 11/2003 | Fenton et al. |
| 2003/0229344 A1 | 12/2003 | Dycus et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0092921 A1 | 5/2004 | Kadziauskas et al. |
| 2004/0092992 A1 | 5/2004 | Adams et al. |
| 2004/0093039 A1 | 5/2004 | Schumert |
| 2004/0097919 A1 | 5/2004 | Wellman et al. |
| 2004/0097996 A1 | 5/2004 | Rabiner et al. |
| 2004/0102804 A1 | 5/2004 | Chin |
| 2004/0133089 A1 | 7/2004 | Kilcoyne et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0199193 A1 | 10/2004 | Hayashi et al. |
| 2004/0249367 A1 | 12/2004 | Saadat et al. |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2005/0015125 A1 | 1/2005 | Mioduski et al. |
| 2005/0033278 A1 | 2/2005 | McClurken et al. |
| 2005/0033337 A1 | 2/2005 | Muir et al. |
| 2005/0090817 A1 | 4/2005 | Phan |
| 2005/0096502 A1 | 5/2005 | Khalili |
| 2005/0119640 A1 | 6/2005 | Sverduk et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0192610 A1 | 9/2005 | Houser et al. |
| 2005/0215858 A1 | 9/2005 | Vail |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0272972 A1 | 12/2005 | Iddan |
| 2005/0273139 A1 | 12/2005 | Krauss et al. |
| 2005/0288555 A1 | 12/2005 | Binmoeller |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0159731 A1 | 7/2006 | Shoshan |
| 2006/0190034 A1 | 8/2006 | Nishizawa et al. |
| 2006/0211943 A1 | 9/2006 | Beaupre |
| 2006/0253050 A1 | 11/2006 | Yoshimine et al. |
| 2006/0270916 A1 | 11/2006 | Skwarek et al. |
| 2006/0293656 A1 | 12/2006 | Shadduck et al. |
| 2007/0008744 A1 | 1/2007 | Heo et al. |
| 2007/0010709 A1 | 1/2007 | Reinschke |
| 2007/0016235 A1 | 1/2007 | Tanaka et al. |
| 2007/0016236 A1 | 1/2007 | Beaupre |
| 2007/0020065 A1 | 1/2007 | Kirby |
| 2007/0032701 A1 | 2/2007 | Fowler et al. |
| 2007/0032704 A1 | 2/2007 | Gandini et al. |
| 2007/0051766 A1 | 3/2007 | Spencer |
| 2007/0055228 A1 | 3/2007 | Berg et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0106317 A1 | 5/2007 | Shelton et al. |
| 2007/0118115 A1 | 5/2007 | Artale et al. |
| 2007/0123748 A1 | 5/2007 | Meglan |
| 2007/0130771 A1 | 6/2007 | Ehlert et al. |
| 2007/0135686 A1 | 6/2007 | Pruitt et al. |
| 2007/0149881 A1 | 6/2007 | Rabin |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0182842 A1 | 8/2007 | Sonnenschein et al. |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0270651 A1 | 11/2007 | Gilad et al. |
| 2007/0275348 A1 | 11/2007 | Lemon |
| 2007/0276424 A1 | 11/2007 | Mikkaichi et al. |
| 2007/0287933 A1 | 12/2007 | Phan et al. |
| 2008/0015413 A1 | 1/2008 | Barlow et al. |
| 2008/0015575 A1 | 1/2008 | Odom et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0082039 A1 | 4/2008 | Babaev |
| 2008/0082098 A1 | 4/2008 | Tanaka et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0281200 A1 | 11/2008 | Voic et al. |
| 2008/0281315 A1 | 11/2008 | Gines |
| 2008/0287948 A1 | 11/2008 | Newton et al. |
| 2008/0300588 A1 | 12/2008 | Groth et al. |
| 2008/0312502 A1 | 12/2008 | Swain et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0143678 A1 | 6/2009 | Keast et al. |
| 2009/0171350 A1* | 7/2009 | Dycus ............... A61B 18/1482 606/48 |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0248021 A1 | 10/2009 | McKenna |
| 2009/0254080 A1 | 10/2009 | Honda |
| 2009/0270771 A1 | 10/2009 | Takahashi |
| 2009/0270853 A1 | 10/2009 | Yachi et al. |
| 2009/0287205 A1 | 11/2009 | Ingle |
| 2010/0036370 A1 | 2/2010 | Mirel et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0158307 A1 | 6/2010 | Kubota et al. |
| 2010/0187283 A1 | 7/2010 | Crainich et al. |
| 2010/0204802 A1 | 8/2010 | Wilson et al. |
| 2010/0222752 A1 | 9/2010 | Collins, Jr. et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2011/0009857 A1 | 1/2011 | Subramaniam et al. |
| 2011/0028964 A1 | 2/2011 | Edwards |

(56) References Cited

U.S. PATENT DOCUMENTS

| | | |
|---|---|---|
| 2011/0087224 A1 | 4/2011 | Cadeddu et al. |
| 2011/0257680 A1 | 10/2011 | Reschke et al. |
| 2011/0270245 A1 | 11/2011 | Horner et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0041358 A1 | 2/2012 | Mann et al. |
| 2012/0078139 A1 | 3/2012 | Aldridge et al. |
| 2012/0078244 A1 | 3/2012 | Worrell et al. |
| 2012/0085358 A1 | 4/2012 | Cadeddu et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0296843 A1 | 11/2013 | Boudreaux et al. |
| 2013/0299555 A1* | 11/2013 | Sniffin ............... A61B 17/068 227/176.1 |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0194864 A1 | 7/2014 | Martin et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0228844 A1 | 8/2014 | Horlle et al. |
| 2014/0230243 A1* | 8/2014 | Roy ............... A61B 18/1445 29/874 |
| 2014/0263541 A1 | 9/2014 | Leimbach et al. |
| 2014/0263552 A1 | 9/2014 | Hall et al. |
| 2014/0276731 A1 | 9/2014 | Voegele et al. |
| 2015/0032150 A1 | 1/2015 | Ishida et al. |
| 2015/0080876 A1 | 3/2015 | Worrell et al. |
| 2015/0080889 A1 | 3/2015 | Cunningham et al. |
| 2015/0080891 A1 | 3/2015 | Shelton, IV et al. |
| 2015/0100056 A1 | 4/2015 | Nakamura |
| 2015/0137422 A1 | 5/2015 | Horner et al. |
| 2015/0209103 A1 | 7/2015 | Artale et al. |
| 2015/0223869 A1 | 8/2015 | Mayer et al. |
| 2015/0230861 A1 | 8/2015 | Woloszko et al. |
| 2015/0250531 A1 | 9/2015 | Dycus et al. |
| 2015/0272659 A1 | 10/2015 | Boudreaux et al. |
| 2015/0272660 A1 | 10/2015 | Boudreaux et al. |
| 2015/0297288 A1 | 10/2015 | Joseph |
| 2015/0305796 A1 | 10/2015 | Wang |
| 2015/0327918 A1 | 11/2015 | Sobajima et al. |
| 2015/0351830 A1 | 12/2015 | Allen, IV et al. |
| 2015/0374430 A1 | 12/2015 | Weiler et al. |
| 2016/0008023 A1 | 1/2016 | Yates et al. |
| 2016/0038225 A1 | 2/2016 | Couture et al. |
| 2016/0045248 A1 | 2/2016 | Unger et al. |
| 2016/0045770 A1 | 2/2016 | Yamada |
| 2016/0051316 A1 | 2/2016 | Boudreaux |
| 2016/0066980 A1 | 3/2016 | Schall et al. |
| 2016/0074095 A1 | 3/2016 | Strobl et al. |
| 2016/0074099 A1 | 3/2016 | Kappus et al. |
| 2016/0074108 A1 | 3/2016 | Woodruff et al. |
| 2016/0128762 A1 | 5/2016 | Harris et al. |
| 2016/0143687 A1 | 5/2016 | Hart et al. |
| 2016/0157923 A1 | 6/2016 | Ding |
| 2016/0157927 A1 | 6/2016 | Corbett et al. |
| 2016/0175029 A1 | 6/2016 | Witt et al. |
| 2016/0199123 A1 | 7/2016 | Thomas et al. |
| 2016/0199124 A1 | 7/2016 | Thomas et al. |
| 2016/0199125 A1 | 7/2016 | Jones |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296270 A1 | 10/2016 | Strobl et al. |
| 2017/0056097 A1 | 3/2017 | Monson et al. |
| 2017/0105787 A1 | 4/2017 | Witt et al. |
| 2017/0105789 A1 | 4/2017 | Boudreaux et al. |
| 2017/0135751 A1 | 5/2017 | Rothweiler et al. |
| 2017/0164972 A1 | 6/2017 | Johnson et al. |
| 2017/0189102 A1 | 7/2017 | Hibner et al. |
| 2017/0312014 A1 | 11/2017 | Strobl et al. |
| 2017/0312015 A1 | 11/2017 | Worrell et al. |
| 2017/0312016 A1 | 11/2017 | Strobl et al. |
| 2017/0312017 A1 | 11/2017 | Trees et al. |
| 2017/0312018 A1 | 11/2017 | Trees et al. |
| 2017/0325878 A1 | 11/2017 | Messerly et al. |
| 2017/0367751 A1 | 12/2017 | Ruddenklau et al. |
| 2018/0085156 A1 | 3/2018 | Witt et al. |
| 2018/0125571 A1 | 5/2018 | Witt et al. |
| 2018/0228530 A1 | 8/2018 | Yates et al. |
| 2018/0263683 A1 | 9/2018 | Renner et al. |
| 2018/0280075 A1 | 10/2018 | Nott et al. |
| 2018/0368906 A1 | 12/2018 | Yates et al. |
| 2019/0000468 A1 | 1/2019 | Adams et al. |
| 2019/0000470 A1 | 1/2019 | Yates et al. |
| 2019/0000528 A1 | 1/2019 | Yates et al. |
| 2019/0000530 A1 | 1/2019 | Yates et al. |
| 2019/0000555 A1 | 1/2019 | Schings et al. |
| 2019/0099209 A1 | 4/2019 | Witt et al. |
| 2019/0099212 A1 | 4/2019 | Davison et al. |
| 2019/0099213 A1 | 4/2019 | Witt et al. |
| 2019/0099217 A1 | 4/2019 | Witt et al. |

FOREIGN PATENT DOCUMENTS

| | | |
|---|---|---|
| CN | 2868227 Y | 2/2007 |
| DE | 4300307 A1 | 7/1994 |
| DE | 29623113 U1 | 10/1997 |
| DE | 20004812 U1 | 9/2000 |
| DE | 10201569 A1 | 7/2003 |
| DE | 102005032371 A1 | 1/2007 |
| EP | 0171967 A2 | 2/1986 |
| EP | 0705571 A1 | 4/1996 |
| EP | 0875209 B1 | 5/2006 |
| EP | 1254637 B1 | 8/2007 |
| EP | 1862133 A1 | 12/2007 |
| EP | 2060238 A1 | 5/2009 |
| EP | 1747761 B1 | 10/2009 |
| EP | 1767164 B1 | 1/2013 |
| EP | 2578172 A2 | 4/2013 |
| ES | 2419159 A2 | 8/2013 |
| GB | 2032221 A | 4/1980 |
| JP | S537994 A | 1/1978 |
| JP | H08229050 A | 9/1996 |
| JP | 2002186627 A | 7/2002 |
| JP | 2009213878 A | 9/2009 |
| JP | 2010057926 A | 3/2010 |
| WO | WO-8103272 A1 | 11/1981 |
| WO | WO-9314708 A1 | 8/1993 |
| WO | WO-9800069 A1 | 1/1998 |
| WO | WO-9923960 A1 | 5/1999 |
| WO | WO-0024330 A1 | 5/2000 |
| WO | WO-0128444 A1 | 4/2001 |
| WO | WO-02080794 A1 | 10/2002 |
| WO | WO-2004078051 A2 | 9/2004 |
| WO | WO-2008130793 A1 | 10/2008 |
| WO | 2009067649 A2 | 5/2009 |
| WO | WO-2010104755 A1 | 9/2010 |
| WO | WO-2011008672 A2 | 1/2011 |
| WO | WO-2011044343 A2 | 4/2011 |
| WO | WO-2011144911 A1 | 11/2011 |
| WO | WO-2012044606 A2 | 4/2012 |

(56) References Cited

FOREIGN PATENT DOCUMENTS

| WO | WO-2012061638 A1 | 5/2012 |
|---|---|---|
| WO | 2013102602 A2 | 7/2013 |
| WO | 2013131823 A1 | 9/2013 |
| WO | 2015017989 A1 | 2/2015 |
| WO | 2015017995 A1 | 2/2015 |

OTHER PUBLICATIONS

U.S. Appl. No. 15/142,403, filed Apr. 29, 2016.
U.S. Appl. No. 15/142,425, filed Apr. 29, 2016.
U.S. Appl. No. 15/142,446, filed Apr. 29, 2016.
U.S. Appl. No. 15/142,598, filed Apr. 29, 2016.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalet.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Glaser and Subak-Sharpe,Integrated Circuit Engineering, Addison-Wesley Publishing, Reading, MA (1979). (book—not attached).
Chen et al., "Heat-induced changes in the mechanics of a collagenous tissue: pseudoelastic behavior at 37° C.," Journal of Biomechanics, 31, pp. 211-216 (1998).
Kurt Gieck & Reiner Gieck, Engineering Formulas § Z.7 (7th ed. 1997).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Abbott, et al. Proceedings of the 2007 IEEEIRDJ International Conference on Intelligent Robots and Systems. 410-416, 2007.
Cadeddu et al., "Magnetic positioning system for trocarless laparoscopic instruments," American College of Surgeons Poster, 2004.
Cadeddu et al., "Novel magnetically guided intra-abdominal camera to facilitate laparoendoscopic single site surgery: initial human experience," Surgical Endoscopy, SAGES Oral Manuscript, 2009.
Cadeddu et al., "Transabdominal magnetic anchoring system for trocar-less laparoscopic surgery," American Urological Association Poster, 2002.
Cadeddu et al., "Transabdominal magnetic anchoring system for trocar-less laparoscopic surgery," Journal of Urology Abstract, 2002.
Castellvi et al., "Completely transvaginal NOTES cholecystectomy in a porcine model using novel endoscopic instrumentation," Accepted for Poster Presentation, SAGES Annual Meeting, 2009.
Castellvi et al., "Hybrid transgastric NOTES cholecystectomy in a porcine model using a magnetically anchored cautery and novel instrumentation," Submitted for Presentation, ASGE, 2009.
Castellvi et al., "Hybrid transvaginal NOTES sleeve gastrectomy in a porcine model using a magnetically anchored camera and novel instrumentation," Accepted for Poster Presentation, SAGES Annual Meeting, 2009.
Duchene et al., "Magnetic positioning system for trocarless laparoscopic instruments," Engineering and Urology Society Poster, 2004.
Fernandez et al., "Development of a transabdominal anchoring system for trocar-less laparoscopic surgery," ASME Proceedings of/MECE, 2003.
Gedeon et al., "Maximizing coupling strength of magnetically anchored notes instruments: How thick can we go?" Submittedfor Presentation, Poster, SAGES Annual Meeting, 2008.
Gedeon et al., "Maximizing coupling strength of magnetically anchored notes instruments: How thick can we go?" SAGES Annual Meeting Poster, 2008.
Park et al., "Trocar-less Instrumentation for Laparoscopy: Magnetic Positioning of Intra-Abdominal Camera and Retractor", Annals of Surgery, vol. 245, No. 3, pp. 379-384, Mar. 2007.
Peirs et al., "A miniature manipulator for integration in self-propelling endoscope," Sensors and Actuators, 92:343-9, 2001.
Raman et al., "Complete transvaginal NOTES nephrectomy using magnetically anchored instrumentation," Journal of Endourology, 23(3):, 2009.367-371,2009.
Rapaccini et al., "Gastric Wall Thickness in Normal and Neoplastic Subjects: A Prospective Study Performed by Abdominal Ultrasound", Gastrointestinal Radiology, vol. 13, pp. 197-199. 1988.
Scott et al., "A randomized comparison of laparoscopic, flexible endoscopic, and wired and wireless magnetic NOTES cameras on ex-vivo and in-vivo surgical performance," Digestive Disease Week (DDW), American Society for Gastrointestinal Endoscopy (ASGE) Annual Meeting Abstract, 2008.
Scott et al., "Completely transvaginal NOTES cholecystectomy using magnetically anchored instruments," Surg. Endosc., 21:2308-2316, 2007.
Scott et al., "Evaluation of a novel air seal access port for transvaginal notes cholecystectomy," Submitted for Presentation, SAGES Annual Meeting, 2008.
Scott et al., "Magnetically anchored instruments for transgastric endoscopic surgery," Oral Presentation for SAGES Annual Meeting, Emerging Technology Oral Abstract ET005, 2006.
Scott et al., "Optimizing magnetically anchored camera, light source, graspers, and cautery dissector for transvaginal notes cholecystectomy," Submitted for Presentation, SAGES Annual Meeting, 2008.
Scott et al., "Short-term survival outcomes following transvaginal NOTES cholecystectomy using magnetically anchored instruments," Oral Presentation, ASGE Annual Meeting/DDW, 2007.
Scott et al., "Trans gastric, transcolonic, and transvaginal cholecystectomy using magnetically anchored instruments," SAGES Annual Meeting Poster, 2007.

(56) References Cited

OTHER PUBLICATIONS

Scott et al., "Transvaginal NOTES cholecystectomy using magnetically anchored instruments," Abstract for Video Submission, ASGE IIIh Annual Video Forum, 2007.
Scott et al., "Transvaginal single access 'pure' NOTES sleeve gastrectomy using a deployable magnetically anchored video camera," Digestive Disease Week (DDW), American Society for Gastrointestinal Endoscopy (ASGE) Annual Meeting Poster, 2008.
Swain et al., "Linear stapler formation of ileo-rectal, entero-enteral and gastrojejunal anastomoses during dual and single access 'pure' NOTES procedures: Methods, magnets and stapler modifications," Digestive Disease Week (DDW), American Society for Gastrointestinal Endoscopy (ASGE) Annual Meeting Abstract, 2008.
Swain et al., "Wireless endosurgery for NOTES," Digestive Disease Week (DDW), American Society for Gastrointestinal Endoscopy (ASGE) Annual Meeting Abstract, 2008.
Tang et al., "Live video manipulator for endoscopy and natural orifice transluminal endoscopic surgery (with videos)," Gastrointestinal Endoscopy, 68:559-564, 2008.
Zeltser et al., "Single trocar laparoscopic nephrectomy using magnetic anchoring and guidance system in the porcine model," The Journal of Urology, 178:288-291, 2007.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number Strands in a Litz-Wire Transformer Winding," IEEE Transactions on Power Electronics, vol. 14, No. 2, Mar. 1999, pp. 283-291.
Wright, et al., "Time-Temperature Equivalence of Heat-Induced Changes in Cells and Proteins," Feb. 1998. ASME Journal of Biomechanical Engineering, vol. 120, pp. 22-26.
Douglas, S.C. Introduction to Adaptive Filter. Digital Signal Processing Handbook. Ed. Vijay K. Madisetti and Douglas B. Williams. Boca Raton: CRC Press LLC, 1999.
Jang, J. et al. "Neuro-fuzzy and Soft Computing." Prentice Hall, 1997, pp. 13-89, 199-293, 335-393, 453-496, 535-549.
Erbe Electrosurgery VIO® 200 S, (2012), p. 7, 12 pages, accessed Mar. 31, 2014 at http://www.erbe-med.com/erbe/media/Marketing materialien/85140170 ERBE EN VIO 200 S D027541.
Leonard I. Malis, M.D., "The Value of Irrigation During Bipolar Coagulation," 1989.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
F. A. Duck, "Optical Properties of Tissue Including Ultraviolet and Infrared Radiation," pp. 43-71 in Physical Properties of Tissue (1990).
Orr et al., "Overview of Bioheat Transfer," pp. 367-384 in Optical-Thermal Response of Laser-Irradiated Tissue, A. J. Welch and M. J. C. van Gernert, eds., Plenum, New York (1995).
Campbell et al, "Thermal Imaging in Surgery," p. 19-3, in Medical Infrared Imaging, N. A. Diakides and J. D. Bronzino, Eds. (2008).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Technology Overview, printed from www.harmonicscalpel.com, Internet site, website accessed on Jun. 13, 2007, (3 pages).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Hörmann et al., "Reversible and irreversible denaturation of collagen fibers." Biochemistry, 10, pp. 932-937 (1971).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.

\* cited by examiner

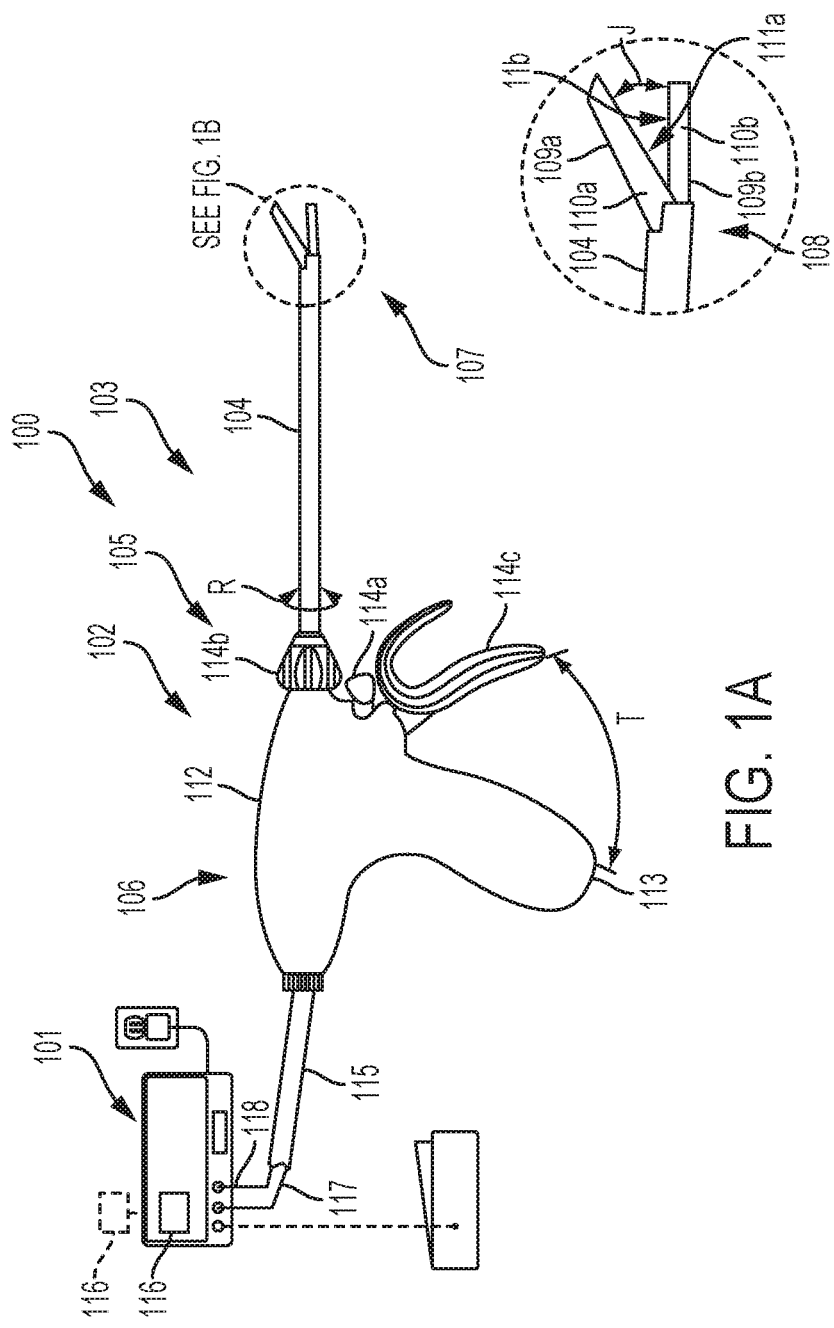

ELECTROSURGICAL INSTRUMENT WITH ELECTRICALLY CONDUCTIVE GAP SETTING AND TISSUE ENGAGING MEMBERS

RELATED APPLICATIONS

This application is related to the following commonly owned patent applications referenced under:

U.S. patent application Ser. No. 15/142,589, entitled ELECTROSURGICAL INSTRUMENT WITH ELECTRICALLY CONDUCTIVE GAP SETTING MEMBER AND ELECTRICALLY INSULATIVE TISSUE ENGAGING MEMBERS;

U.S. patent application Ser. No. 15/142,598, entitled ELECTROSURGICAL INSTRUMENT WITH CONDUCTIVE GAP SETTING MEMBER AND INSULATIVE TISSUE ENGAGING MEMBER HAVING VARIABLE DIMENSIONS AND STIFFNESS;

U.S. patent application Ser. No. 15/142,403, entitled JAW STRUCTURE WITH DISTAL POST FOR ELECTROSURGICAL INSTRUMENTS;

U.S. patent application Ser. No. 15/142,425, entitled NON-LINEAR JAW GAP FOR ELECTROSURGICAL INSTRUMENTS; and U.S. patent application Ser. No. 15/142,446, entitled JAW STRUCTURE WITH DISTAL CLOSURE FOR ELECTROSURGICAL INSTRUMENTS; each of which is incorporated herein by reference in its entirety.

TECHNICAL FIELD

The present disclosure is related generally to medical devices having various mechanisms for grasping and sealing tissue. In particular, the present disclosure is related to medical devices having an electrically conductive gap setting member configured to define a gap between electrodes of an electrosurgical instrument.

BACKGROUND

Electrosurgical devices may be used in many surgical operations. Electrosurgical devices may apply electrical energy to tissue in order to treat tissue. An electrosurgical device may comprise an instrument having a distally mounted end effector comprising one or more electrodes. The end effector can be positioned against tissue such that electrical current may be introduced into the tissue. Electrosurgical devices can be configured for monopolar or bipolar operation. During monopolar operation, current may be introduced into the tissue by an active (or source) electrode on the end effector and returned through a return electrode. The return electrode may be a grounding pad and separately located on a patient's body. During bipolar operation, current may be introduced into and returned from the tissue by the active and return electrodes, respectively, of the end effector.

The end effector may include two or more jaw members. At least one of the jaw members may have at least one electrode. At least one jaw may be moveable from a position spaced apart from the opposing jaw for receiving tissues to a position in which the space between the jaw members is less than that of the first position. This movement of the moveable jaw may compress the tissue held between. Heat generated by the current flow through the tissue in combination with the compression achieved by the jaw's movement may form hemostatic seals within the tissue and/or between tissues and, thus, may be particularly useful for sealing blood vessels, for example. The end effector may comprise a cutting member. The cutting member may be movable relative to the tissue and the electrodes to transect the tissue.

Electrosurgical devices also may include mechanisms to clamp tissue together, such as a stapling device, and/or mechanisms to sever tissue, such as a tissue knife. An electrosurgical device may include a shaft for placing the end effector proximate to tissue undergoing treatment. The shaft may be straight or curved, bendable or non-bendable. In an electrosurgical device including a straight and bendable shaft, the shaft may have one or more articulation joints to permit controlled bending of the shaft. Such joints may permit a user of the electrosurgical device to place the end effector in contact with tissue at an angle to the shaft when the tissue being treated is not readily accessible using an electrosurgical device having a straight, non-bending shaft.

SUMMARY

In one aspect, an end effector comprises a grasping portion and a gap setting portion. The grasping portion comprises a first jaw member comprising a first electrode; a second jaw member comprising a second electrode, wherein at least one of the first and second jaw members is movable relative to the other between an open position and a closed position; a first electrically conductive member located either on the first jaw member or the second jaw member, the electrically insulative member sized and configured to engage tissue, wherein the first electrically conductive member is electrically isolated from one of the first or second electrode. The gap setting portion comprises a second electrically conductive member located at the distal end of either the first jaw member or the second jaw member, the second electrically conductive member sized and configured to define a minimum distance between the first and second electrodes, wherein the second electrically conductive member is electrically isolated from one of the first or second electrodes.

In one aspect, an electrosurgical device comprises a handle assembly, an end effector, and a connecting member. The end effector, comprises a grasping portion and a gap setting portion. The grasping portion comprises a first jaw member comprising a first electrode; a second jaw member comprising a second electrode, wherein at least one of the first and second jaw members is movable relative to the other between an open position and a closed position; a first electrically conductive member located either on the first jaw member or the second jaw member, the electrically insulative member sized and configured to engage tissue, wherein the first electrically conductive member is electrically isolated from one of the first or second electrode. The gap setting portion comprises a second electrically conductive member located at the distal end of either the first jaw member or the second jaw member, the second electrically conductive member sized and configured to define a minimum distance between the first and second electrodes, wherein the second electrically conductive member is electrically isolated from one of the first or second electrodes. The connecting member is configured to connect the handle assembly and the end effector.

In one aspect, an electrosurgical system comprises an electrosurgical energy generator and an electrosurgical device. The electrosurgical device comprises a handle assembly, an end effector, and a connecting member. The end effector, comprises a grasping portion and a gap setting portion. The grasping portion comprises a first jaw member comprising a first electrode; a second jaw member comprising a second electrode, wherein at least one of the first and second jaw members is movable relative to the other between an open position and a closed position; a first electrically conductive member located either on the first jaw member or the second jaw member, the electrically insulative member sized and configured to engage tissue, wherein the first electrically conductive member is electrically isolated from one of the first or second electrode. The gap setting portion comprises a second electrically conductive member located at the distal end of either the first jaw member or the second jaw member, the second electrically conductive member sized and configured to define a minimum distance between the first and second electrodes, wherein the second electrically conductive member is electrically isolated from one of the first or second electrodes. The connecting member is configured to connect the handle assembly and the end effector.

BRIEF DESCRIPTION OF THE DRAWINGS

The features of the various aspects are set forth with particularity in the appended claims. The various aspects, both as to organization and methods of operation, together with advantages thereof, may, however best be understood by reference to the following description, taken in conjunction with the accompanying drawings as follows:

FIG. 1A shows a surgical instrument in electrical communication with an energy source, according to one aspect of the present disclosure.

FIG. 1B is a detailed view of the end effector of the surgical instrument shown in FIG. 1A, according to one aspect of the present disclosure.

DETAILED DESCRIPTION

Figure 2B:
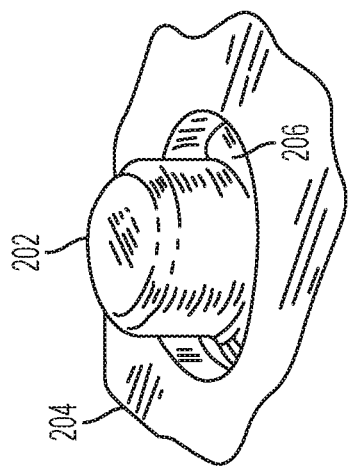
FIG. 2A and FIG. 2B show two types of electrically insulative elements, according to one aspect of the present disclosure.

The following description of certain examples of the technology should not be used to limit its scope. Other examples, features, aspects, aspects, and advantages of the technology will become apparent to those skilled in the art from the following description, which is, by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, aspects, examples, etc. described herein may be combined with any one or more of the other teachings, expressions, aspects, examples, etc. that are described herein. The following described teachings, expressions, aspects, examples, etc. should, therefore, not be viewed in isolation relative to each other. Various suitable ways in which the teachings herein may be combined will be readily apparent to those of ordinary skill in the art in view of the teachings herein. Such modifications and variations are intended to be included within the scope of the claims.

Also, in the following description, it is to be understood that terms such as front, back, inside, outside, upper, lower, top, bottom and the like are words of convenience and are not to be construed as limiting terms. Terminology used herein is not meant to be limiting insofar as devices described herein, or portions thereof, may be attached or utilized in other orientations. The various aspects will be described in more detail with reference to the drawings. Throughout this disclosure, the term "proximal" is used to describe the side of a component, e.g., a shaft, a handle assembly, etc., closer to a user operating the surgical instrument, e.g., a surgeon, and the term "distal" is used to describe the side of the component farther from the user operating the surgical instrument.

Aspects of the present disclosure are presented for a single electrosurgical device configured for grasping tissue and performing sealing procedures using electrical and/or other energy. An end effector of the electrosurgical device may include multiple members arranged in various configurations to collectively perform the aforementioned functions. As used herein, an end effector may be referred to as a jaw assembly or clamp jaw assembly comprising an upper jaw member and a lower jaw member where at least one of the upper jaw member and the lower jaw member may be movable relative to the other. Each of the jaw members may be adapted to connect to an electrosurgical energy source. Each jaw member may incorporate an electrode. The electrode may be a positive or negative electrode. In a bipolar electrosurgical device, the electrodes may be adapted for connection to the opposite terminals of the electrosurgical energy source, such as a bipolar radio frequency (RF) generator, so as to generate a current flow therebetween. An electrosurgical energy may be selectively communicated through tissue held between the jaw members to effect a tissue seal and/or treatment. Tissue may be coagulated from the current flowing between the opposite polarity electrodes on each jaw member.

At least one jaw member may include a knife channel defined therein configured to reciprocate a knife therealong for severing tissue held between the jaw members. The knife channel may be an extended slot in the jaw member. The knife may be provided within a recess associated with the at least one jaw member. The electrosurgical device may have both coagulation and cutting functions. This may eliminate or reduce instrument interchange during a surgery. Cutting may be achieved using mechanical force alone or a combination of mechanical force and the electrosurgical energy. The electrosurgical energy may be selectively used for coagulation and/or cutting. The knife may be made from an electrically conductive material adapted to connect to the electrosurgical source, and selectively activatable to separate tissue disposed between the jaw members. The knife may be spring biased such that once tissue is severed, the knife may automatically return to an unengaged position within the knife channel or a retracted position in the recess.

In some aspects, the jaw members may be movable relative to each other. During operation of the electrosurgical device, at least one of the jaw members may move from a first, open position where the jaw members can be disposed around a mass of tissue, to a second, closed position where the jaw members grasp the tissue. The jaw members therefore may move through a graspers-like range of motion, similar to that of conventional pliers. In the second position, current flows between the jaw members to achieve hemostasis of the tissue captured therebetween. The jaw members may be configured to have a relatively thick proximal portion to resist bending. At least one of the jaw members may have a three-dimensional configuration with a D-shaped cross-sectional. The three-dimensional configuration with the D-shaped cross-sectional may resist bending. A lock mechanism may be included to lock the jaw members in the closed position. The lock mechanism may set the clamp pressure between the jaw members. At least one electrically conductive gap setting member may be provided between the jaw members to establish a desired gap between electrodes in bipolar electrosurgical devices.

The electrosurgical device may incorporate components to set a gap between the jaws of the end effector, grasp tissue via the end effector, deliver energy to the tissue via one or more electrodes, and cut the tissue via a dissecting device such as a tissue knife. The structural capabilities of any aspect of an electrosurgical device may be designed for use in one or more of a variety of surgical procedures. In some surgical procedures, the treated tissue may be readily accessible to an end effector affixed to a relatively straight and unbendable shaft. In some alternative surgical procedures, the tissue may not be readily accessible to the end effector on such a shaft. In such procedures, the electrosurgical device may incorporate a shaft designed to bend so that the end effector may contact the tissue requiring treatment. In such a device, the shaft may include one or more articulated joints that may permit the shaft to bend under control by the user. A sliding knife may include a feature to provide actuating force to the sliding knife. A knife actuator may be operably coupled to the shaft for selectively reciprocating the knife through the knife channel.

A front portion assembly may be designed for a specific surgical procedure, while a reusable handle assembly, configured to releasably attach to a front portion assembly, may be designed to provide control of surgical functions common to each front portion assembly, such as tissue grasping, cauterizing, and cutting. Consequently, the number and types of devices required for surgeries can be reduced. The reusable handle assembly may be designed to automate common functions of the electrosurgical device. Device intelligence may be provided by a controller located in the reusable handle assembly that is configured to receive information from a front portion assembly. Such information may include data regarding the type and use of the front portion assembly. Alternatively, information may include data indicative of the position and/or activation of control components (such as buttons or slides that can be manipulated) that may indicate what system functions should be activated and in what manner.

In some non-limiting examples, the controller may supply the RF current when the energy activation control is placed in an activating position by the user. In some alternative non-limiting examples, the controller may supply the RF current for a predetermined period of time once the energy activation control is placed in an activing position. In yet another non-limiting example, the controller may receive data related to the position of the jaws and prevent the RF current from being supplied to the to the one or more tissue cauterization power contacts if the jaws are not in a closed position.

In some aspects, any of the mentioned examples also may be configured to articulate along at least one axis through various means, including, for example, a series of joints, one or more hinges or flexure bearings, and one or more cam or pulley systems. Other features may include cameras or lights coupled to one or more of the members of the end effector, and various energy options for the surgical device.

The electrosurgical device can be configured to source energy in various forms including, without limitation, electrical energy, monopolar and/or bipolar RF energy, microwave energy, reversible and/or irreversible electroporation energy, and/or ultrasonic energy, heat energy, or any combination thereof, to the tissue of a patient either independently or simultaneously. The energy can be transmitted to the electrosurgical device by a power source in electrical communication with the electrosurgical device. The power source may be a generator. The power source may be connected to the electrosurgical device via a suitable transmission medium such as a cable. The power source may be separate from the electrosurgical device or may be made integrally with the electrosurgical device to form a unitary electrosurgical system. In one non-limiting example, the power source may include one or more batteries located within a portion of the electrosurgical device. It may be understood that the power source may source energy for use on the tissue of the patient as well as for any other electrical use by other devices, including, without limitation, lights, sensors, communication systems, indicators, and displays, which operate in relation to and/or with the electrosurgical device to form an electrosurgical system.

The electrosurgical device may be configured to source electrical energy in the form of RF energy. The electrosurgical device can transmit the RF energy through tissue compressed between two or more jaws. Such RF energy may cause ionic agitation in the tissue, in effect producing resistive heating, and thereby increasing the temperature of the tissue. Increased temperature of the tissue may lead to tissue cauterization. In some surgical procedures, RF energy may be useful for removing, shrinking, or sculpting soft tissue while simultaneously sealing blood vessels. RF energy may work particularly well on connective tissue, which is primarily composed of collagen and shrinks when contacted by heat. Because a sharp boundary may be created between the affected tissue and the surrounding tissue, surgeons can operate with a high level of precision and control, without sacrificing untargeted adjacent tissue.

The RF energy may be in a frequency range described in EN 60601-2-2:2009+A11:2011, Definition 201.3.218—HIGH FREQUENCY. For example, the frequency in monopolar RF applications may be typically restricted to less than 5 MHz. However, in bipolar RF applications, the frequency can be almost anything. Frequencies above 200 kHz can be typically used for monopolar applications in order to avoid the unwanted stimulation of nerves and muscles that would result from the use of low frequency current. Lower frequencies may be used for bipolar applications if the risk analysis shows the possibility of neuromuscular stimulation has been mitigated to an acceptable level. Normally, frequencies above 5 MHz are not used in order to minimize the problems associated with high frequency leakage currents. Higher frequencies may, however, be used in the case of bipolar applications. It is generally recognized that 10 mA is the lower threshold of thermal effects on tissue.

As discussed above, the electrosurgical device may be used in conjunction with a generator. The generator may be an electrosurgical generator characterized by a fixed internal impedance and fixed operating frequency that deliver maximum power to an external load (e.g., tissue) having an electrical impedance in the range of about 50 ohms to 150 ohms. In this type of bipolar electrosurgical generator, the applied voltage may increase monotonically as the load impedance increases toward the maximum "open circuit" voltage as the load impedance increases to levels of tens of thousands of ohms or more. In addition, the electrosurgical device may be used with a bipolar electrosurgical generator having a fixed operating frequency and an output voltage that may be substantially constant over a range of load impedances of tens of ohms to tens of thousands of ohms including "open circuit" conditions. The electrosurgical device may be advantageously used with a bipolar electrosurgical generator of either a variable voltage design or substantially constant voltage design in which the applied voltage may be interrupted when the delivered current decreases below a predetermined level. Such bipolar generators may be referred to as automatic generators in that they may sense the completion of the coagulation process and terminate the application of voltage, often accompanied by an audible indication in the form of a cessation of a "voltage application" tone or the annunciation of a unique "coagulation complete" tone. Further, the electrosurgical device may be used with an electrosurgical generator whose operating frequency may vary with the load impedance as a means to modulate the applied voltage with changes in load impedance.

Various aspects of electrosurgical devices use therapeutic and/or sub-therapeutic electrical energy to treat tissue. Some aspects may be utilized in robotic applications. Some aspects may be adapted for use in a hand operated manner. In one non-limiting example, an electrosurgical device may include a proximal handle, a distal working end or end effector, and an introducer or elongated shaft disposed in-between.

In some non-limiting medical procedures, the electrosurgical device may be used to weld or seal vessels prior to tissue resection. Such vessels also may be removed as part of procedures to resect other tissue such as cysts, tumors, or infected materials. Blood vessel sealing may reduce bleeding, thereby decreasing potential harmful effects during a resection procedure. In such procedures, vessels may be cut at the cauterization location. It may be understood that complete sealing may be required at the site of the cut to prevent bleeding. It is therefore useful to have an electrosurgical device that may be prevented from cutting a vessel until complete sealing is assured.

To properly seal vessels, two mechanical parameters that affect thickness of the sealed vessel may be accurately controlled: the pressure applied to the vessel and the gap between the electrodes. Proper sealing may require that sufficient pressure is placed on the vessel to assure that the vessel walls are proximate to each other and no intervening gap remains therebetween. The vessel may be compressed to a pressure within a predetermined range. A typical range of appropriate pressures may be between 30 and 250 pounds per square inch (psi). In addition, proper sealing may require that sufficient power is provided to assure that the vessel walls receive sufficient heat to weld the walls together. Thus, both tissue compression and tissue cauterization may be required to form a proper seal. These can be achieved by the jaw members of the end effector. As mentioned above, the jaw members may grasp, compress, and deliver the energy to the tissue.

To effectively carry out hemostasis, the jaw members should efficiently conduct a proper current flow through the grasped tissue. When that current is insufficient, coagulation of the tissue or vessel may be compromised. When the current is excessive, correspondingly excessive heating may occur with a potential for the generation of damaging electrical arcing. Excessive heating may result in the phenomenon of tissue and blood coagulum sticking to the surface of the jaw members. This may result in increased electrical impedance between the electrodes of the device and the tissue that may subsequently be grasped for the purpose of treatment. Such sticking tissue may evoke a disruption of the coagulated surface, which in itself may compromise the intended hemostatic effect. The end effector may incorporate highly polished electrode surfaces for the purpose of reducing the extent of tissue sticking as well as to facilitate their cleaning when sticking does occur. When grasping tissue, the jaw members may come into mutual contact, causing a short circuit. For example, when a small tissue component is grasped between the jaw members and/or when the jaw members are compressed hard, the electrodes may be in contact with each other in the vicinity of the grasped tissue, causing short-circuiting. The jaw members may include insulative coatings that may be in contact in some geometry, but the insulative coatings may not prevent the short-circuiting.

Arcing may be a possibility as the jaw members closely approach each other. Arcing may happen when monopolar electrosurgical devices are used where the current flows completely through the patient. These high voltage electrical currents may arc from the small electrode to nearby, non-targeted vital structures or may follow erratic paths as they flow through the patient's body, thereby causing damage to tissues both near and at some distance from the electrode. Aberrant current arcs may cause deep tissue necrosis and inadvertent damage to adjacent tissue masses.

Arcing also may happen in a procedure performed by a bipolar electrosurgical device, for example, a "coagulative painting" procedure, where the side surfaces of the electrically active jaw members are drawn over the surface of membranous tissue such as the mesentery. Done properly, this action congeals the microvessels within such thin tissues. However, higher voltage settings on the generator applied across a thin layer of tissue to the other jaw member can cause arcing of the device. For some bipolar electrosurgical devices, microarcs between the electrodes may be normal during operation. However, these microarcs can attack the electrodes. If the electrodes, for example, contain some polymer material, these microarcs can draw out carbon from the polymer material, thus creating carbon tracks, sometimes referred to as "carbon arc tracking," which then may lead to short-circuiting of the electrodes. Also, in general, in case of excessive voltage or sharp edges, a significant arc or a big arc may happen, and the generator may perceive the arc as short-circuiting. Short-circuiting due to either a big arc or carbon arc tracking can be very problematic. This calls for adjustment of the voltage or maintenance of the spacing between the two jaw members to avoid arcing the system. It may be desirable to adjust the spacing rather than changing the applied voltage because lowering the voltage may result in less than desirable tissue effects. Of course, it is also necessary for the surgeon to maintain space between the electrodes of the device to achieve the requisite performance.

In general, for bipolar electrosurgical devices, electrodes of opposite polarity should not contact each other during the application of energy. Shorting of the electrodes effectively shunts energy away from the tissue. Some shunting happens with arcing. It is known that Paschen's Law gives the breakdown voltage, which is the voltage necessary to start a discharge or electric arc between two electrodes in a gas as a function of pressure and gap length. The breakdown voltage of various gases between parallel metal plates as the gas pressure and gap distance were varied has been studied. It has been found that the voltage necessary to arc across the gap decreases as the pressure is reduced and then increased gradually, exceeding its original value. It has also been found that at normal pressure, the voltage needed to cause an arc reduces as the gap size is reduced but only to a point. As the gap is reduced further, the voltage required to cause an arc begins to rise and again exceeds its original value. For a given gas, the voltage is a function only of the product of the pressure and gap length. According to Paschen's Law, at higher pressures and gap lengths, the breakdown voltage is approximately proportional to the product of pressure and gap length. If a bipolar device allows shorting or arcing between the tissue treating electrodes, the effectiveness of the device may be diminished. In one aspect, present disclosure provides an electrically conductive gap setting member to prevent one electrode from contacting the opposed electrode of a bipolar electrosurgical device. In various aspects, the electrically conductive gap setting member may define a uniform or non-uniform gap along the length and/or the width of the jaw member(s) or tissue contacting area thereof.

According to various aspects, an end effector may include an electrically conductive gap setting member to ensure that the electrodes of the jaw members do not electrically contact each other within a range of the closing or opening motion of the jaw members. The electrically conductive gap setting member defines a gap between the upper and lower electrodes of the jaw members when the jaw members are at the closed position. The gap may be uniform or non-uniform along the length and/or width of the tissue contacting area of the jaw. The electrically conductive gap setting member may be dimensioned so that when the jaw members are in the closed position, the gap may be sufficient to prevent electrical shorting between the electrodes. The electrically conductive gap setting member may control the gap distance between opposing electrodes of the jaw members. The heights of the electrically conductive gap setting members are selected as the value to achieve a minimum spacing between the electrode surfaces driving a current path through the grasped tissue, which may be of a distance that does not exceed a value necessary to achieve effective coagulation while avoiding arcing and/or short-circuiting. Although the electrically conductive gap setting member is made of an electrically conductive material, the electrically conductive gap setting member is electrically isolated from the electrode connected to the positive terminal or pole of the energy source and may contact the electrode connected to the negative or ground terminal or pole of the energy source.

In various aspects, the end effector may comprise tissue engaging members. The tissue engaging members may be made of an electrically conductive material. The electrically conductive tissue engaging members are electrically isolated from the energy circuit. In one aspect, the electrically conductive tissue grasping members are embedded in an electrically insulative material to prevent contacting the positive terminal or pole of the energy source. In another aspect, the electrically conductive tissue grasping members comprise an electrically insulative layer or coating. The insulative layer may have a thickness in the range of about 0.002" to about 0.050", more preferably about 0.003" to about 0.007". At thicknesses of about 0.001" or less, the thickness of the insulative layer may be insufficient to prevent shorting of the electrodes. Insulative layer thicknesses above about 0.002" and below about 0.050" may cause adequate hemostasis. It has been observed, however, that the greater the minimum distance between the proximate current conducting portions of the opposing electrodes in the region of current flow through the tissue, the longer the current path through the tissue and the more difficult it may become to obtain the desired localized and intense heating to achieve adequate hemostasis. Insulative layer thicknesses above about 0.050" may be too large for most practical applications using the ceramic insulative materials described.

In various aspects, an electrically conductive gap setting member may be provided between the jaw members. The electrically conductive gap setting member may be affixed on and/or integral to one jaw member and extend to the other jaw member. The electrically conductive gap setting member may protrude through the jaw member. The electrically conductive gap setting member may define a gap between the jaw members. The electrically conductive gap setting member may be electrically conductive. The electrically conductive gap setting member may be a pin. The pin may be metal. The gap setting member may be made of a material that is electrically conductive and also is stiff to resist deformation in response to an applied force. The material is stiff with a high tensile strength and is incompressible. The electrically conductive gap setting member may be made of an electrically conductive metal or metal alloy and preferably may be made of steel, such as medical grade stainless steel, for example. The electrically conductive gap setting member may not contact the electrically conductive surface or portion of any electrode, including the electrode which the electrically conductive gap setting member may be affixed on or protrude through and the opposite electrode. The electrically conductive gap setting member may be sized and configured to avoid short-circuiting between the opposing electrodes and/or ensure that the electrodes would not close enough to arc without the presence of tissue between the electrodes.

In various aspects, the gap between the jaw members or the electrodes may be about 0.002" to about 0.02", preferably about 0.003" to about 0.012", more preferably about 0.004" to about 0.01", even more preferably about 0.004" to about 0.008". The gap between the electrode and the upper of the tissue engaging member on the opposite electrode may be about 0 to about 0.005", preferably about 0.001" to about 0.005", more preferably about 0.001" to about 0.002", more preferably about 0.001". These gaps may be configured to provide desired sealing of vessels. As smaller distances between the electrodes are employed, for example, at values of about 0.001" or about 0.002", arcing may occur. For example, it has been found that as the height diminishes below about 0.005", for example, to about 0.001" or about 0.002", isotonic saline fluid is encountered in the surgical field and the spacing between grasping surfaces, and an arc may form and evoke intense heating in its ionized pathway with resultant damage.

According to various aspects, an end effector may include an electrically insulative member between the jaw members. The electrically insulative member may be provided on at least one of the jaw members. Each jaw member may have a surface. The surface may be a tissue grasping surface. The surface may comprise an electrode. The surface of the upper jaw member may face the surface of the lower jaw member. The electrically insulative member may comprise at least one electrically conductive or tissue engaging member. The at least one tissue engaging member is a protuberance in the form of a short cylindrical solid or hollow object, bump, hump, lump, ridge, bulge, knob, swelling peg, or button made integral with or inserted into a jaw member and protruding through openings defined by an electrode of the jaw member. The tissue engaging members are configured to facilitate gripping or grasping tissue located between the jaw members and enhance manipulation of tissue during the operation of the electrosurgical device, such as the sealing process.

In some aspects where there may be more than one tissue engaging member, the more than one tissue engaging member may be provided on the same surface or on difference surfaces of the jaw members. In some aspects where at least one tissue engaging member may be provided on one surface of a jaw member, effective grasping of very thin tissue and small blood vessels may be provided. Manufacturing costs may be reduced as the at least one tissue engaging member need only be applied to one of the two jaw members. Because it is not required to have the tissue engaging member on both jaw members, it may not be required to precisely control the widths of more than one insulative member and the spacing therebetween to assure required registration between an upper and lower disposed array of tissue engaging members. This may reduce manufacturing costs. This may enhance manufacturability inasmuch as the requirement for precisely registering the insulative members at two grasping surfaces of the jaw members may be eliminated during final assembly.

In various aspects, at least one electrode may be made on at least one surface of the at least one jaw member. The tissue engaging member may protrude from an opening in the electrode. In some non-limiting examples, the opening in the electrode may be line-line same size as the member protruding from the opening. Therefore, the tissue engaging member may be a tight fit through the opening. In some other non-limiting examples, the opening in the electrode may be larger than the tissue engaging member and thereby form a donut around the tissue engaging member. When the opening is larger than the tissue engaging member, it may be easier for manufacturing since it may be easier to align the tissue engaging members if needed. The opening may have a diameter twice as large as a diameter of the tissue engaging member. In some aspects, the opening may have a size such that the space around the tissue engaging member may allow the tissue engaging member to move and/or deform. In any case, the opening, the tissue engaging member, and the space therebetween should have appropriate sizes and/or dimensions such that the electrosurgical device and its electrodes achieve the requisite performance.

In various aspects, the at least one tissue engaging member may have various shapes. The at least one tissue engaging member may have the shape of a cube, rectangular prism, triangular prism, octagonal prism, tetrahedron, square pyramid, cylinder, cone, sphere, or any other suitable shape. An upper surface of the at least one tissue engaging member may be round, square, rectangle, oval, or any other suitable shape. In some aspects where there is more than one tissue engaging member, the tissue engaging members may each have the same shape or different shapes with any combination of various shapes. In certain aspects, the top surface can be smooth or patterned.

In various aspects, there may be more than one tissue engaging member. The tissue engaging members may have different shapes and/or sizes. All or some of the tissue engaging members may change shapes and/or sizes along the length of the electrodes. The tissue engaging members may have increasing or decreasing sizes along the length of the electrodes. The tissue engaging members may change shapes and/or sizes in a regular fashion or randomly.

In various aspects, the electrodes on the surfaces of the jaw members may be made of metal. The exposed portions of the surfaces of the jaw members may have smooth surfaces to minimize sticking to tissue or coagulum and to facilitate their cleaning when tissue debris or coagulum does accumulate. The surfaces of the jaw members may include thermally conductive components such as copper, silver, aluminum, tungsten, nickel, or any other thermally conductive materials that may occur to those skilled in the art. Laminar composites coated with a biocompatible metal coating may be applied to the surfaces. The jaw members may include laminar composites of thermally conductive copper and a mechanically stronger material, particularly, higher modulus stainless steel. Biocompatibility of the jaw members may be maintained through an electro-deposited biocompatible metal coating, such as chromium, that coats both the stainless steel and copper laminate while not affecting the tissue engaging members. In some non-limiting examples, for end effectors with small jaw members, for example, having a width of about 0.039" (1 mm) at their tip, laminar composites having a layer of 304 stainless steel of thickness of about 0.011" and a corresponding layer of copper having about 0.052" thickness may be provided. For larger jaw members, laminar composites having a layer of 304 stainless steel of thickness about 0.015" and a corresponding layer of copper having about 0.075" to about 0.085" thickness may be provided. The biocompatible coating may be provided, for example, as an electro-deposited chromium coating, for example, that identified as MED-COAT 2000 marketed by Electrolyzing Corporation of Ohio, Cleveland, Ohio 44112. This biocompatible coating is described as meeting or exceeding USP Class VI certification.

The at least one tissue engaging member may be made of material. The electrically insulative material may be alumina, ceramic, nylon, polyphthalamide (PPA), TEFLON, polyimide, parylene, any other suitable material, and/or any combinations thereof. In various aspects, smooth metal surfaces may be provided on the surfaces of the jaw members to reduce sticking of tissue or coagulum and these surfaces may be coated with an electrically conductive non-stick coating. Upper surfaces of the at least one tissue engaging member may be coated with non-stick coating material. Such non-stick coating material may be sufficiently thin and/or applied to a sufficiently rough surface to provide a multiplicity of regions on the contacting surfaces that are uncoated with insulative non-stick coating material. Such non-stick coatings may include metal-filled (containing metal particles) organic materials such as fluoropolymers or other compounds generally known under the tradename TEFLON (polytetrafluoroethylene polymers and copolymers) (PTFE) or thin fluoropolymers known under the tradename VYDAX, both of which are manufactured by E.I. DuPont de Nemours of Wilmington, Del. In addition, metallic coatings such as ME-92 (ME-92 Operations, Providence, R.I.) and MED-COAT 2000 (supra) may be applied to the stainless steel surfaces of the jaw members to reduce the sticking of tissue thereto.

In various aspects, the length of the jaw members may be set for the particular application in surgery. For example, the length of the jaw members of about 0.4" or 0.5" to about 0.75", such as about 0.47" (12 mm), may be used for smaller anatomical structures or fine work. For larger anatomical structures, the length of the members may be about 1" or greater, for example, about 1.57" (40 mm).

The at least one tissue engaging member may have an appropriate diameter such that the tissue engaging member is neither so small as to pierce tissue nor so large as to take away too much of the electrode surface. The minimum diameter of the member may be about 0.03125" (1/32") as a tissue engaging member of this diameter may not pierce tissue unless the pressure applied on the tissue from the tissue engaging member is very high. If too much of the electrode surface is taken away by the tissue engaging member or members, there may be too little of the electrode surface and therefore, too little of the electrically conductive area adjacent to the tissue engaging member/members, and the electrosurgical device and/or the electrodes may not achieve the requisite performance. In some aspects where there is more than one tissue engaging member, the tissue engaging members may have the same or different diameters of any combination.

The at least one tissue engaging member may have a height about 0.001" smaller than the gap between the electrodes or jaw members, for example, about 0.001" to about 0.019", preferably about 0.002" to about 0.011", more preferably about 0.003" to about 0.009", such as about 0.008", about 0.003" to about 0.007", or about 0.004" to about 0.007". In general, the height may be less than about 0.020" or less than or equal to about 0.010". The minimum value found practical for the height may be about 0.003". In some aspects where there is more than one member, the members may have the same or different heights of any combination.

These sizes may be selected to achieve the most efficient electrode contact geometry for achieving the most efficient hemostasis with respect to tissue or vessels grasped. The sizes and/or dimensions may be configured such that the electrosurgical device and the electrodes achieve the requisite performance.

In various aspects, the tissue engaging members may have the same height or different heights. The members may be provided on one jaw member and received in receiving pockets on the other jaw member. The depths of the receiving pockets may vary. The members and the receiving pockets may be configured to define a non-uniform arrangement along the length of the jaw members.

In various aspects, the tissue engaging members may be integrally made in the electrode. The tissue engaging members may be molded in the electrode(s). The tissue engaging members may be fabricated by an insert molding manufacturing process. This may reduce the cost of manufacturing. In some other aspects, the tissue engaging members may be inserted into openings defined by the electrode(s). In some other aspects, the electrode on the surface of one jaw member may be coined or bent to form tissue grasping members having the same function as the tissue engaging members that may contact a non-electrically conductive portion on the surface of the other jaw member. Portions on the surface of the other jaw member corresponding to the tissue engaging members may be cut out to expose the non-electrically conductive portion and receive the tissue engaging members. In some other aspects, the tissue engaging members may be made on a embossed insert that may be inserted in an insulated material in one jaw member. The embossed insert may be inserted and set in glue in the jaw member. A shim may be used to set the heights of the tissue engaging members.

In various aspects, the tissue engaging members may be made of ceramic, glass, or glass/ceramic applied by plasma deposition methods; physical vapor deposition; screen or pad printing followed by fusing of the insulative layer by exposure to high temperatures; a photolithography process; or attachment of individual ceramic members using brazing, soldering, or adhesive bonding methods. The tissue engaging members may be made from plastic and using coating methods such as, for example, dipping, plasma coating, encasement, or the like.

In some non-limiting examples, the tissue engaging members may be provided as discrete, spaced-apart elements disposed in arrays on one surface of a jaw member. The tissue engaging members may be cubes or any other suitable shapes. The insulative spacers defined within the arrays may be made by first depositing, for example, by plasma deposition or physical vapor deposition, an electrically insulative layer over a desired length of the surface. Next, thin grinding wheels can be used to grind away the electrically insulative layer to produce the pattern of tissue engaging members. In some non-limiting examples, the tissue engaging members or arrays may be made by thick film printing of insulative material followed by exposure to elevated temperatures to affect its bonding to the surface. In some non-limiting examples, the tissue engaging members may be made as layers utilizing a physical mask to deposit the electrically insulative material in required areas on the surface. Alternatively, the surface may be configured containing an array of openings of circular cross-sectional, peripheral shape, or any other suitable shape. The tissue engaging members may then be provided as electrically insulative glass, ceramic, or glass/ceramic pegs inserted within the openings.

In the following detailed description, reference is made to the accompanying drawings, which form a part hereof. In the drawings, similar symbols and reference characters typically identify similar components throughout the several views, unless context dictates otherwise.

FIG. 1A shows an electrosurgical instrument 100 in electrical communication with a generator 101, according to one aspect of the present disclosure. The electrosurgical instrument 100 may be configurable with a flexible circuit 102 according to various aspects. The electrosurgical instrument 100 may comprise an elongate member 103, such as a shaft 104, having a proximal portion 105 coupled to a handle assembly 106. A distal portion 107 of the elongate member 103 may comprise an end effector 108 (see FIG. 1B) coupled to a distal end of the shaft 104. In some aspects, the end effector 108 may comprise a first jaw member 109a and a second jaw member 109b, each having an outer portion or surface 110a, 110b. At least one of the first jaw member 109a and the second jaw member 109b may move relative to the shaft 104. There may be only one jaw movable relative to the shaft 104, and the other jaw may be fixed relative to the shaft 104. At least one of the first jaw member 109a and the second jaw member 109b may be rotatably movable relative to the other along a path shown by arrow J to transition the first and second jaw members 109a, 109b between open and closed positions. In operation, the first and second jaw members 109a, 109b may be transitioned from the open position to a closed position to capture tissue therebetween. Captured tissue may contact one or more working portions of the jaw set 111a, 111b configured to apply energy to treat target tissue located at or near the end effector 108. The type of energy may take various forms and includes, without limitation, monopolar and/or bipolar RF energy, microwave energy, reversible and/or irreversible electroporation energy, and/or ultrasonic energy, or any combination thereof.

The handle assembly 106 may comprise a housing 112 defining a grip 113. In various aspects, the handle includes one or more control interfaces 114a-c, e.g., a button or switch 114a, rotation knob 114b rotatable along arrow R, and a trigger 114c movable relative to the grip 113 along arrow T, configured to provide operation instructions to the end effector 108. Multiple buttons, knobs, or triggers described also may be included as part of the housing 112 in order to manipulate one or more of the functioning members at the end effector 108. In some aspects, the handle assembly 106 may be further configured to electrically couple to a generator 101 to supply the electrosurgical instrument 100 with energy.

The generator 101 may be connected to the electrosurgical instrument 100 via a suitable transmission medium such as a cable 115. In one example, the generator 101 may be coupled to a controller, such as a control unit 116, for example. In various aspects, the control unit 116 may be made integrally with the generator 101, or may be provided as a separate circuit module or device electrically coupled to the generator 101 (shown in phantom to illustrate this option). The control unit 116 may include automated or manually operated controls to control the amount of current delivered by the generator 101 to the electrosurgical instrument 100. Although, as presently disclosed, the generator 101 is shown separate from the electrosurgical instrument 100, in some aspects, the generator 101 (and/or the control unit 116) may be made integrally with the electrosurgical instrument 100 to form a unitary electrosurgical system where a battery located within the electrosurgical instrument 100 may be the energy source and a circuit coupled to the battery produces the suitable electrical energy, ultrasonic energy, or heat energy.

While the generator 101 is illustrated as generally coupled to the handle assembly 106, e.g., with a cord, it is to be understood that in some aspects the generator 101 may be positioned within the elongate member 103 and/or the handle assembly 106. For example, in one aspect, the generator 101 comprises one or more direct current batteries positioned in the handle assembly 106, shaft 104, or a portion thereof.

In one aspect, the generator 101 may comprise an input device located on a front panel of the generator 101. The input device may comprise any suitable device that generates signals suitable for programming the operation of the generator 101, such as a keyboard, or input port, for example. In one example, one or more electrodes in the first jaw member 109a and one or more electrodes in the second jaw member 109b may be coupled to the generator 101. The cable 115 may comprise multiple electrical conductors for the application of electrical energy to a first electrode (which may be designated as a + electrode) and to a second electrode (which may be designated as a − electrode) of the electrosurgical instrument 100. It may be recognized that + and − designations are made solely for convenience and do not indicate an electrical polarity. An end of each of the conductors may be placed in electrical communication with a terminal of the generator 101. The generator 101 may have multiple terminals, each configured to contact one or more of the conductors. The control unit 116 may be used to activate the generator 101, which may serve as an electrical source. In various aspects, the generator 101 may comprise an RF source, an ultrasonic source, a direct current source, and/or any other suitable type of electrical energy source, for example, one which may be activated independently or simultaneously.

In various aspects, the cable 115 may comprise at least one supply conductor 117 and at least one return conductor 118, wherein current can be supplied to the electrosurgical instrument 100 via the at least one supply conductor 117 and wherein the current can flow back to the generator 101 via the at least one return conductor 118. In various aspects, the at least one supply conductor 117 and the at least one return conductor 118 may comprise insulated wires and/or any other suitable type of conductor. As described below, the at least one supply conductor 117 and the at least one return conductor 118 may be contained within and/or may comprise the cable 115 extending between, or at least partially between, the generator 101 and the end effector 108 of the electrosurgical instrument 100. The generator 101 can be configured to apply a sufficient voltage differential between the supply conductor 117 and the return conductor 118 such that sufficient current can be supplied to the end effector 108 to perform the intended electrosurgical operation.

In one example, the generator 101 may be implemented as an electrosurgery unit (ESU) capable of supplying power sufficient to perform bipolar electrosurgery using RF energy. In one example, the ESU can be a Force Triad™ Energy Platform sold by Medtronic of Boulder Colo. In some aspects, such as for bipolar electrosurgery applications, an electrosurgical instrument 100 having an active electrode and a return electrode can be utilized, wherein the active electrode and the return electrode can be positioned against, adjacent to, and/or in electrical communication with the tissue to be treated such that current can flow from the active electrode through the PTC bodies and to the return electrode through the tissue. Thus, in various aspects, the electrosurgical system may comprise a supply path and a return path, wherein the captured tissue being treated completes, or closes, the circuit. In other aspects, the generator 101 may provide sub-therapeutic RF energy levels for purposes of evaluating tissue conditions and providing feedback in the electrosurgical system. Such feedback may be employed to control the therapeutic RF energy output of the electrosurgical instrument 100. Sub-therapeutic RF energy levels may be used for bipolar surgical procedures if a risk analysis shows the possibility of neuromuscular stimulation has been mitigated to an acceptable level. Under some conditions, frequencies above 5 MHz may not be used in order to minimize problems associated with high frequency leakage currents. However, higher frequencies may be used in the case of bipolar techniques. It is generally recognized that 10 mA is the lower threshold of thermal effects on tissue.

During operation of electrosurgical instrument 100, the user generally grasps tissue, supplies energy to the grasped tissue to form a weld or a seal (e.g., by an actuating button and/or pedal), and then drives a tissue-cutting member at the distal end of the electrosurgical instrument through the grasped tissue. According to various aspects, a jaw-closing member may be provided, and the translation of the axial movement of the jaw-closing member may be paced, or otherwise controlled, to aid in driving the jaw-closing member at a suitable rate of travel. By controlling the rate of travel, the likelihood that the captured tissue has been properly and functionally sealed prior to transection with the cutting member may be increased.

Figure 2A:
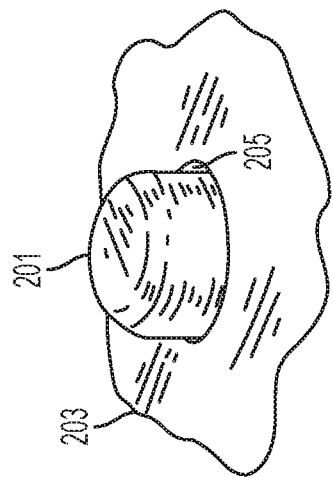

FIG. 2A and FIG. 2B show two types of tissue engaging members with respect to the electrode from which the members protrude, according to one aspect of the present disclosure. In FIG. 2A, a tissue engaging member 201 protrudes from an opening 205 defined by an electrode 203. The inner periphery of the opening 205 may be substantially the same as the outer periphery of the tissue engaging member 201. The opening 205 tightly fits around the tissue engaging member 201. The tissue engaging member 201 and the opening 205 may both have round peripheries as shown in the figure. However, it is understood that the tissue engaging member 201 and the opening 205 can have peripheries of any suitable shape or size. In FIG. 2B, a tissue engaging member 202 may protrude from an opening 206 defined by an electrode 204. The opening 206 may be larger than the tissue engaging member 202. The inner periphery of the opening 206 may not tightly fit the outer periphery of the tissue engaging member 202. The inner periphery of the opening 206 may be away from the outer periphery of the tissue engaging member 202 at a distance. The distance between the inner periphery of the opening 206 and the outer periphery of the tissue engaging member 202 may be uniform or non-uniform around the whole outer periphery of the tissue engaging member 202. The tissue engaging member 202 may or may not be at the center of the opening 206. The tissue engaging member 202 may have a round outer periphery. The opening 206 also may be round. The opening 206 may define a space in the form of a donut around the tissue engaging member 202.

Figure 3:
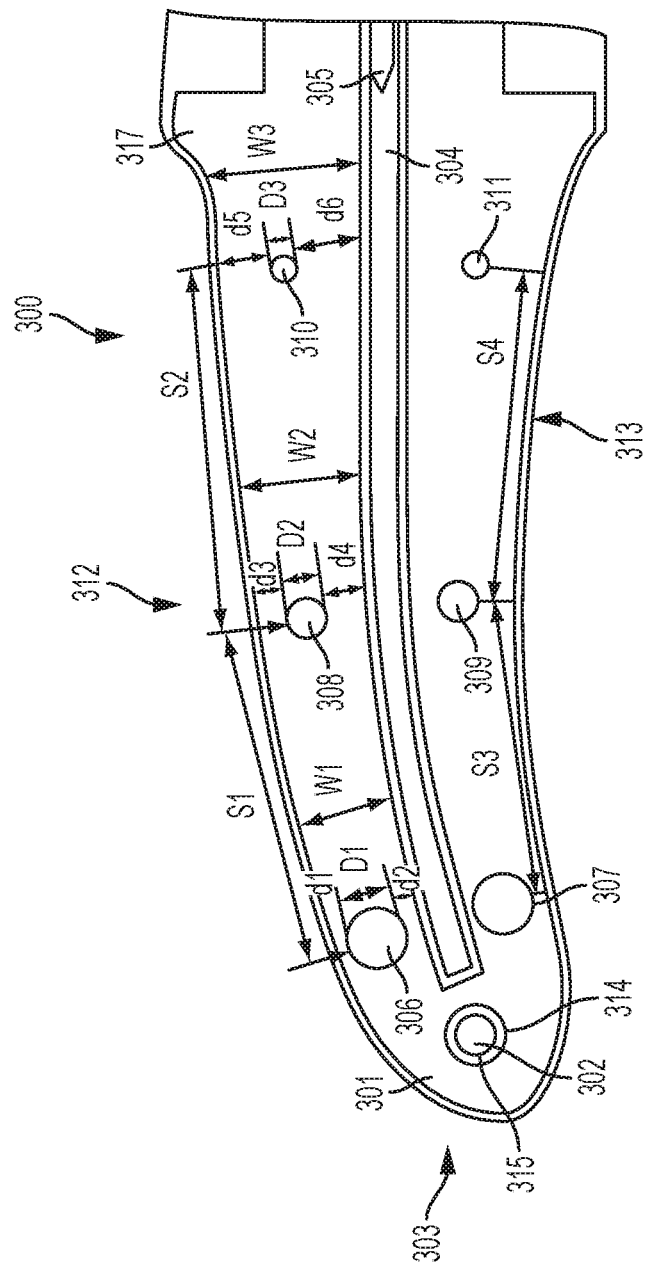
FIG. 3 shows a plan view of one aspect of a jaw member comprising a distal electrically conductive gap setting member and tissue engaging members having variable sizes along the jaw member, according to one aspect of the present disclosure.

FIG. 3 shows a plan view of a jaw comprising a distal electrically conductive gap setting member 302 and tissue engaging members 306-311, according to one aspect of the present disclosure. An electrode 301 may be provided on one surface of the jaw member 300. An electrically conductive gap setting member 302 is located at the distal end 303 of the jaw member 300. In one aspect, the gap setting member 302 is a metal pin suitable to set a gap between the upper electrode (not shown) and the lower electrode 301. The gap setting member 302 is electrically conductive, but is electrically isolated from the surrounding electrode 301. In one aspect, the gap setting member 302 may be made of an electrically conductive metal or metal alloy and preferably may be made of steel, such as medical grade stainless steel, for example. The gap setting member 302 protrudes through an opening 314 defined by the lower electrode 301. A space 315 is provided between the inner periphery of the opening 314 and the outer periphery of the gap setting member 302 such that the gap setting member 302 does not contact any electrically conductive portion of the lower electrode 301. Although the opening 314 may have a substantially round shape, the opening 314 can have any shape as long as the inner periphery of the opening 314 may not contact any part of the outer periphery of the gap setting member 302. The gap setting member 302 may be located on the lower face of the upper jaw or on the upper face of the lower jaw member 300. The gap setting member 302 may be integrally made with or affixed on the lower electrode 301 or the upper electrode (not shown).

In one aspect, the electrically conductive gap setting member 302 may be made of an electrically conductive stiff material that resists deformation in response to an applied force. The material may be a high tensile strength incompressible material. The electrically conductive gap setting member 302 is located at the distal end 303 of the jaw member 300. In one aspect, the gap setting member 302 is an electrically conductive metal pin made of a stiff incompressible material having a high tensile strength, such as steel, and suitable for setting a gap between the upper electrode (not shown here) and the lower electrode 301. In one aspect, the gap setting member 302 may be made of an electrically conductive metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art.

A knife channel 304 may be provided in the interior, such as the middle, of the jaw member 300. A cutting member 305, such as a knife, may be provided in the channel 304 for cutting tissue after the tissue has been sealed using electrosurgical energy. The cutting member 305 may be slidable along the knife channel 304. The cutting member 305 may be adapted to cut tissue by moving distally in the knife channel 304 when the jaw member 300 and the opposing jaw are in the closed position to grip tissue. Although generally speaking the knife channel 304 may be located along the lateral center of the electrode 301, this is not necessarily always the case. Thus, in other aspects, the knife channel 304 may be offset from the center to either side of the electrode 301.

At least one tissue engaging member may be located on the lower electrode 301 of the jaw member 300, for example, to provide grasping surfaces to grasp tissue. The at least one tissue engaging member 306-311 provided on at least one of two sides 312, 313 of the electrode 301 along the knife channel 304. The tissue engaging members may change shape along the length of the electrode 301. The tissue engaging members 306-311 may change shape down the length of the electrode 301 from the distal end 303 to the proximal end 317 of the jaw member 300. For example, the tissue engaging members 306-311 may be cylinders, and therefore, the upper surfaces of the tissue engaging members 306-311 may be round. The top of the tissue engaging members 306-311 also may provide grasping surfaces to grasp tissue.

The tissue engaging members 306-311 may be located on an insulative element of the jaw member 300 that supports the lower electrode 301. In this configuration, the tissue engaging members 306-311 protrude through the lower electrode 301. In another aspect, the tissue engaging members 306-311 may be located on an insulative element of the upper jaw member that supports the upper electrode 503. In this configuration, the tissue engaging members 306-311 protrude through the upper electrode. Accordingly, either or both upper and/or lower electrodes may comprise tissue engaging members 306-311 configured to provide grasping surfaces to grasp tissue. The top of the tissue engaging members 306-311 also may be configured to provide grasping surfaces to grasp tissue.

The tissue engaging members 306-311 may be made of electrically insulative material such as a polymer and, more specifically, can be an electrically insulative material (e.g., polyimide, polyester, fluorocarbon, or any polymeric material, or any combinations thereof). The tissue engaging members 306-311 may be generally attached to the tissue contacting side of the jaw member 300.

In one aspect, the tissue engaging members 306-311 may comprise a nonstick coating or may be made of a nonstick material such as TEFLON. Any nonstick material or non-stick surface finish may be suitable to prevent tissue from sticking to the electrically conductive portion of the electrode 301. The electrically insulative material of the tissue engaging members 306-311 may be alumina, ceramic, nylon, polyphthalamide (PPA), TEFLON, polyimide, parylene, any other suitable material, and/or any combinations thereof. Top surfaces of the tissue engaging members 306-311 may be coated with electrically insulative non-stick coating material. Such non-stick coating material may be sufficiently thin and/or applied to a sufficiently rough surface to provide a multiplicity of regions on the contacting surfaces that are uncoated with insulative non-stick coating material. Such non-stick coatings may include metal-filled (containing metal particles) organic materials such as fluoropolymers or other compounds generally known under the tradename TEFLON (polytetrafluoroethylene polymers and copolymers) or thin fluoropolymers generally known under the tradename VYDAX, both of which are manufactured by E.I. DuPont de Nemours of Wilmington, Del. In addition, metallic coatings such as ME-92 (ME-92 Operations, Providence, R.I.) and MED-COAT 2000 (supra) may be applied to the stainless steel surfaces of the jaw member 300 to reduce the sticking of tissue thereto. In one aspect, the tissue engaging member 306-311 may be made of a dielectric material that can be printed on the electrodes. In one aspect, the tissue engaging members 306-311 comprises a nonstick coating or may be made of a nonstick material such as polytetrafluoroethylene (PTFE), which is a synthetic fluoropolymer of tetrafluoroethylene that has numerous applications. The best known trade name of PTFE-based formulas may be TEFLON by DuPont Co., for example.

In one aspect, the tissue engaging members 306-311 may be made of an electrically conductive material and isolated from the energy source. The electrically conductive tissue engaging members 306-311 may be embedded in an electrically insulative material or may be coated with an electrically insulative material to prevent energy flow through the electrically conductive tissue engaging members 306-311. In one aspect, the tissue engaging members 306-311 may be made of an electrically conductive metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art.

In one aspect, a tissue engaging layer may be made by bonding a dielectric cover film on the tissue contacting surface of the electrode 301. The tissue engaging members 306-311 may be made by etching the dielectric cover film bonded to the tissue contacting surface of the electrode 301. In one aspect, the tissue engaging members 306-311 may be made of electrically insulative material such as a polymer, more specifically a polyimide, polyester, fluorocarbon, or any polymeric material, or any combinations thereof. The tissue engaging members 306-311 may be generally attached to the tissue contacting surface of the upper jaw member or lower jaw member 300.

At each side 312, 313 of the lower electrode 301, the widths of the side of the electrode 301 increase down the length of the electrode from the distal end 303 to the proximal end 317 of the jaw member 300. For example, the widths W1-W3 of the side 312 of the electrode 301 increase down the length of the electrode 301 from the distal end 303 to the proximal end 317 of the jaw member 300. Distances from the members to the edges of the sides of the electrode also may change down the length of the electrode 301 from the distal end 303 to the proximal end 317 of the jaw member 300. For example, the distances d1-d6 from the members 306, 308, 310 to the edges of the side 312 of the electrode 301 may increase down the length of the electrode 301 from the distal end 303 to the proximal end 317 of the jaw member 300. For example, d1, d2<d3, d4<d5, d6. The distances d1 and d2 may be the same or different. The distances d3 and d4 may be the same or different. The distances d5 and d6 may be the same or different. The spacing S1-S4 between the members may be the same or different. The spacing S1-S4 may be selected to achieve the most efficient contact geometry for, in turn, achieving the most efficient hemostasis with respect to tissue or vessels grasped between the jaws.

Along each side 312, 313 of the lower electrode 301, sizes of the upper surfaces of the members may increase, decrease, or change randomly down the length of the electrode from the distal end 303 to the proximal end 317 of the jaw member 300. For example, as shown here, diameters D1-D3 of the members 306, 308, and 310 along the side 312 of the electrode may decrease down the length of the lower electrode 301 from the distal end 303 to the proximal end 317 of the jaw member 300.

Figure 4:
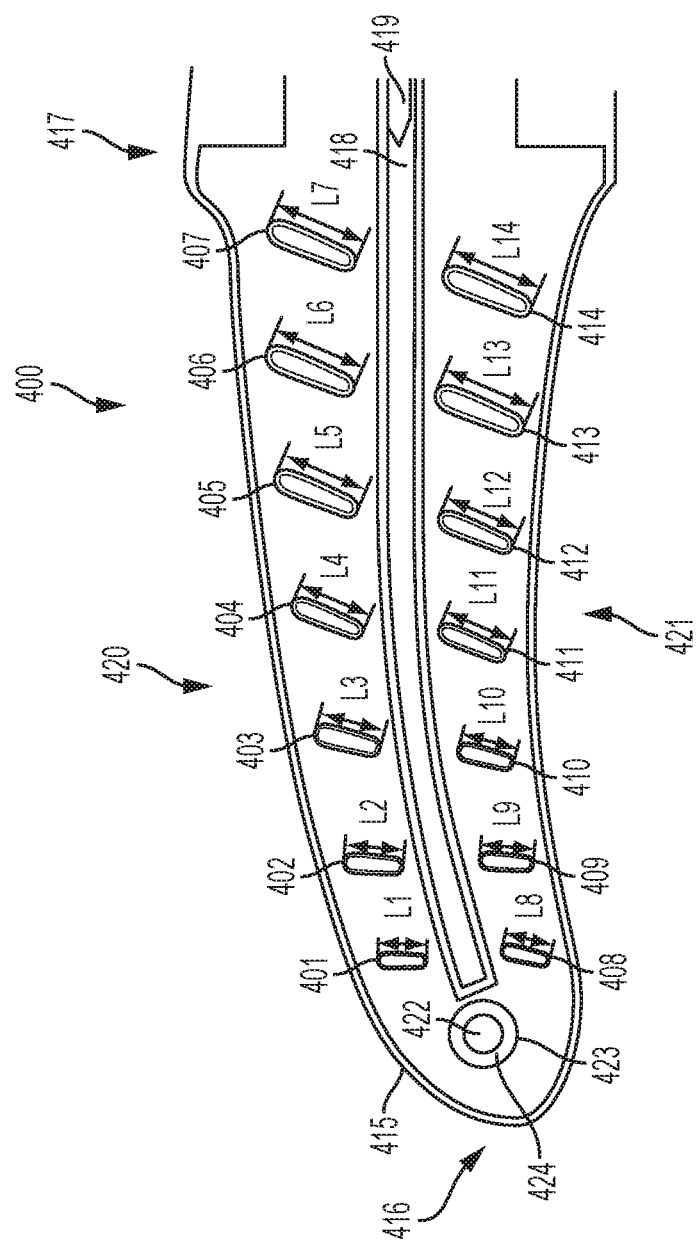
FIG. 4 shows a plan view of one aspect of a jaw member comprising a distal electrically conductive gap setting member and tissue engaging members having variable sizes and/or shapes along the jaw member, according to one aspect of the present disclosure.

FIG. 4 shows a plan view of a jaw member 400 comprising a distal electrically conductive gap setting member 422 and tissue engaging members 401-414, according to one aspect of the present disclosure. The jaw member 400 may include tissue engaging members 401-414 along the lower electrode 415 between the distal end 416 and the proximal end 417 of the jaw member 400. The jaw member 400 may include a channel 418 in the middle of the jaw. A cutting member 419, such as a knife, may be provided in the channel 418 for cutting tissue. The cutting member 419 may be slidable along the channel 418.

The tissue engaging members 401-407 may be provided on one side 420 of the lower electrode 415. The tissue engaging members 408-414 may be provided on the other side 421 of the lower electrode 415. The tissue engaging members 401-414 may be in the form of elongate members. The tissue engaging members 401-414 may be oriented in any direction. The tissue engaging members 401-414 may be provided parallel to each other. The tissue engaging members 401-414 may extend between the peripheries of the lower electrode 415. The tissue engaging members 401-414 may have a uniform or different thickness T. The tissue engaging members 401-414 may be evenly or non-evenly spaced along the length of the lower electrode 415. The distance S between the tissue engaging members 401-414 may be the same or different. The sizes and/or the shapes of the tissue engaging members 401-414 may change along the lower electrode 415 between the distal end 416 and the proximal end 417 of the jaw member 400. For example, the lengths L1-L7 along the side 420 of the electrode 415 may increase down the length of the electrode 415 from the distal end 416 to the proximal end 417 of the jaw member 400. The lengths L8-L14 along the side 412 of the lower electrode 415 also may increase down the length of the electrode 415 from the distal end 416 to the proximal end 417 of the jaw member 400. The lengths of the tissue engaging members 401-414 along one side of the electrode 415 also may decrease or change randomly down the length of the electrode 415 from the distal end 416 to the proximal end 417 of the jaw member 400, which is not shown here.

The tissue engaging members 401-414 may be located on an insulative element of the lower jaw member 400 that supports the lower electrode 415. In this configuration, the tissue engaging members 401-414 protrude through the lower electrode 415. In another aspect, the tissue engaging members 401-414 may be located on an insulative element of an upper jaw member that supports an upper electrode (not shown here). In this configuration, the tissue engaging members 401-414 protrude through the upper electrode. Accordingly, either or both upper electrode and/or lower electrodes 415 may comprise tissue engaging members 401-414 configured to provide grasping surfaces to grasp tissue located between the upper electrode and lower electrode 415. The top of the tissue engaging members 401-414 also may be configured to provide grasping surfaces to grasp tissue.

In one aspect, the tissue engaging members 401-414 are made of an electrically insulative material as described generally hereinabove and particularly in connection with FIGS. 3 and 5. For example, the tissue engaging members 401-414 may be made of electrically insulative material such as a polymer and, more specifically, can be an electrically insulative material (e.g., polyimide, polyester, fluorocarbon, or any polymeric material, or any combinations thereof). The tissue engaging members 401-414 may be generally attached to the tissue contacting side of the jaw member 400. In one aspect, the tissue engaging members 401-414 may comprise a nonstick coating or may be made of a nonstick material such as TEFLON. Any nonstick material or nonstick surface finish may be suitable to prevent tissue from sticking to the electrically conductive portion of the upper electrode (not shown).

In one aspect, the tissue engaging members 401-414 may be made of an electrically conductive material and isolated from the energy source. The electrically conductive tissue engaging members 401-414 may be embedded in an electrically insulative material or may be coated with an electrically insulative material to prevent energy flow through the electrically conductive tissue engaging members 401-414. In one aspect, the tissue engaging members 401-414 may be made of an electrically conductive metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art.

An electrically conductive gap setting member 422 is located at the distal end 416 of the jaw member 400. In one aspect, the gap setting member 422 is an electrically conductive metal pin made of a stiff incompressible material having a high tensile strength, such as steel, and suitable for setting a gap between the upper electrode (not shown) and the lower electrode 415. In one aspect, the gap setting member 422 may be made of an electrically conductive metal or metal alloy and preferably may be made of steel, such as medical grade stainless steel, for example. The gap setting member 422 may protrude through an opening 423 defined by the electrode 415. A space 424 is provided between the inner periphery of the opening 423 and the outer periphery of the gap setting member 422 such that the gap setting member 422 does not contact any electrically conductive portion of the electrode 415. Although the opening 423 is shown to have a substantially round shape, the opening 423 can have any shape as long as the inner periphery of the opening 423 may not contact any part of the outer periphery of the gap setting member 422.

The electrically conductive gap setting member 422 is located at the distal end 416 of the jaw member 400. The gap setting member 422 may protrude through an opening 423 defined in the electrode 415. A space 424 is provided between the inner periphery of the opening 423 and the outer periphery of the gap setting member 422 such that the gap setting member 422 does not contact any electrically conductive portion of the electrode 415. Although the opening 423 may have a substantially round shape, the opening 423 can have any shape as long as the inner periphery of the opening 423 may not contact any part of the outer periphery of the gap setting member 422.

In one aspect, the electrically conductive gap setting member 422 is an electrically conductive metal pin made of a stiff incompressible material having a high tensile strength and suitable for setting a gap between an upper electrode (not shown here) and a lower electrode 415. In one aspect, the gap setting member 422 is made of an electrically conductive stiff incompressible material having a high tensile strength as described generally hereinabove and particularly in connection with FIG. 3 and hereinbelow in connection with FIG. 5. For example, the gap setting member 422 may be made of metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art.

Figure 5:
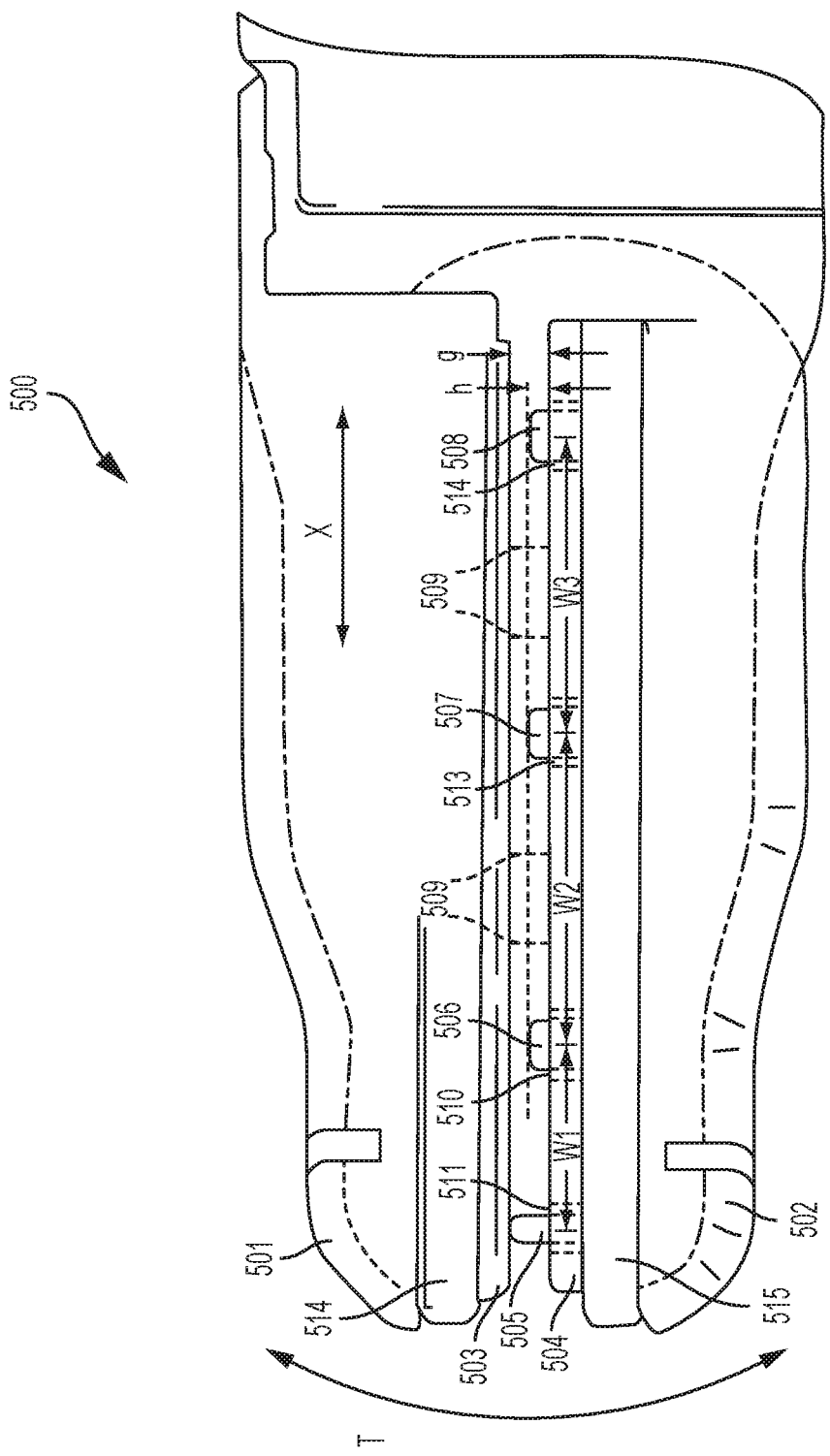
FIG. 5 shows a side elevational view of one aspect of an end effector comprising a distal electrically conductive gap setting member and tissue engaging members, according to one aspect of the present disclosure.

FIG. 5 shows a side elevational view of one aspect of an end effector 500 comprising a distal electrically conductive gap setting member 505 and tissue engaging members 506, 507, 508 located, according to one aspect of the present disclosure. The end effector 500 may have an upper jaw member 501 and a lower jaw member 502. At least one of the upper jaw member 501 and the lower jaw member 502 may move relative to the other. Both the upper jaw member 501 and the lower jaw member 502 may move relative to each other. At least one of the upper jaw member 501 and the lower jaw member 502 may move along the arrow T. The upper jaw member 501 and the lower jaw member 502 may have an open position and a closed position. In the open position, the upper jaw member 501 and the lower jaw member 502 may have the maximum distance from each other and may not move farther away from each other. In the closed position, the upper jaw member 501 and the lower jaw member 502 may have the minimum distance from each other and may not move closer to each other. The movement of at least one of the jaw members 501, 502 may bring the upper and lower jaw members 501, 502 to a position between the open position and the closed position.

At least one electrode is positioned on at least one jaw member. An upper electrode 503 is provided on a lower surface of the upper jaw member 501. A lower electrode 504 is positioned on an upper surface of the lower jaw member 502. The upper and lower electrodes 503, 504 may be provided facing each other. An electrically conductive gap setting member 505 is located at the distal end of the end effector 500. The gap setting member 505 is electrically conductive and in one aspect is a pin made of a stiff incompressible material having a high tensile strength. In one aspect, gap setting member 505 may be made of a metal or metal alloy and preferably may be made of steel, such as medical grade stainless steel, for example, suitable for setting a gap between the upper and lower electrodes 503, 504. The gap setting member 505 may be provided on the lower face of the upper jaw member 501 or on the upper face of the lower jaw member 502. The gap setting member 505 may be made with or affixed on the lower jaw member 502 or the upper jaw member 501. The gap setting member 505 protrudes through an opening 511 defined by the lower electrode 503 without contacting the lower electrode 503. A space is provided between the inner periphery of the opening 511 and the outer periphery of the gap setting member 505 such that the gap setting member 505 does not contact any electrically conductive portion of the lower electrode 504. Although the opening 511 may have a substantially round shape, the opening 511 can have any shape as long as the inner periphery of the opening 511 may not contact any part of the outer periphery of the gap setting member 505.

A gap "g" is defined as a minimum distance or space between the electrodes 503, 504 when the upper and lower jaw members 501, 502 are in the closed position. As shown here, the gap "g" may be substantially uniform along the length of the electrodes 503, 504 and/or along the length of the jaw members 501, 502. The gap "g" also may be non-uniform, which is not shown. The gap "g" is defined by the gap setting member 505. The gap setting member 505 prevents the undesired contact between the upper and lower electrode 504, 504 when the jaw members 501, 502 are in the closed position.

In one aspect, the gap setting member 505 is an electrically conductive metal pin made of a stiff incompressible material having a high tensile strength, such as steel, and suitable for setting a gap between the upper electrode 503 and the lower electrode 504. In one aspect, the gap setting member 505 may be made of an electrically conductive metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art.

At least one of the upper or lower jaw members 501, 502 comprises a tissue engaging layer or element to facilitate grasping or gripping tissue located between the upper and lower jaw members 501, 502. Tissue engaging members 506-508 may be provided on at least one of the upper or lower jaw members 501, 502. In one aspect, the tissue engaging members 506-508 protrude through corresponding openings 512-514 defined by the lower electrode 504 of the lower jaw member 502. Although the tissue engaging members 506-508 are provided on the upper surface of the lower jaw member 502, in other aspects, tissue engaging members may be provided on a lower surface of the upper jaw member 501 and preferably protrude through openings above the surfaces of the upper and lower electrodes 503, 504 to provide grasping surfaces to grasp tissue located between the jaw members 501, 502. The top of the tissue engaging members 506-508 provide grasping surfaces to grasp tissue.

The tissue engaging members 506-508 may be located on an insulative element 515 of the lower jaw member 502 that supports the lower electrode 504. In this configuration, the tissue engaging members 506-508 protrude through corresponding openings 512-514 defined by the lower electrode 504 of the lower jaw member 502. In another aspect, the tissue engaging members 506-508 may be located on an insulative element 514 of the upper jaw member 501 that supports the upper electrode 503. In this configuration, the tissue engaging members 506-508 protrude through corresponding openings (not shown) defined by the upper electrode 503. Accordingly, either or both upper and/or lower electrodes 503, 504 may comprise tissue engaging members 506-508 configured to provide grasping surfaces to grasp tissue. The top of the tissue engaging members 506-508 also may be configured to provide grasping surfaces to grasp tissue.

The at least one tissue engaging member 506-508 may be made of electrically insulative material. The electrically insulative material may be alumina, ceramic, nylon, polyphthalamide (PPA), TEFLON, polyimide, parylene, any other suitable material, and/or any combinations thereof. In various aspects, smooth metal surfaces may be provided on the surfaces of the jaw members to reduce sticking of tissue or coagulum and these surfaces may be coated with an electrically conductive non-stick coating. Upper surfaces of the at least one tissue engaging member may be coated with electrically insulative non-stick coating material. Such non-stick coating material may be sufficiently thin and/or applied to a sufficiently rough surface to provide a multiplicity of regions on the contacting surfaces that are uncoated with insulative non-stick coating material. Such non-stick coatings may include metal-filled (containing metal particles) organic materials such as fluoropolymers or other compounds generally known under the tradename TEFLON (polytetrafluoroethylene polymers and copolymers) (PTFE) or thin fluoropolymers known under the tradename VYDAX, both of which are manufactured by E.I. DuPont de Nemours of Wilmington, Del. In addition, metallic coatings such as ME-92 (ME-92 Operations, Providence, R.I.) and MED-COAT 2000 (supra) may be applied to the stainless steel surfaces of the jaw members to reduce the sticking of tissue thereto.

In one aspect, the tissue engaging members 506-508 may be made of a dielectric material that can be printed on either the upper or lower electrodes 503, 504. In yet another aspect, the electrically insulative layer may be configured as an electrically insulative cover that further defines the electrically conductive jaw electrode 503, 504 and can act as a tissue engaging member. In one aspect, the tissue engaging members 506-508 may comprise a nonstick coating or may be made of a nonstick material such as polytetrafluoroethylene (PTFE), which is a synthetic fluoropolymer of tetrafluoroethylene that has numerous applications. PTFE-based formulas are best known under the may be tradename TEFLON by DuPont Co., for example. In one aspect, the tissue engaging members 506, 507, and 508 may be made of a dielectric material.

In one aspect, a tissue engaging layer may be made by bonding a dielectric cover film on the tissue contacting surface of the upper and lower electrodes 503, 504. In one aspect, the tissue engaging members 506-508 may be made by etching the dielectric cover film bonded to the tissue contacting surface of the upper or lower electrode 503, 504. In one aspect, at least one of the tissue engaging members 506-508 may be configured to facilitate gripping, grasping, or otherwise manipulating tissue located between the upper and lower electrodes 503, 504.

In one aspect, the tissue engaging members 506-508 may be made of an electrically insulative material such as a polymer, more specifically a polyimide, polyester, fluorocarbon, or any polymeric material, or any combinations thereof. The tissue engaging members 506-508 may be attached to the tissue contacting surface of the upper or lower jaw members 501, 502.

In one aspect, the tissue engaging members 506-508 may be made of an electrically conductive material and isolated from the energy source. The electrically conductive tissue engaging members 506-508 may be embedded in an electrically insulative material or may be coated with an electrically insulative material to prevent energy flow through the electrically conductive tissue engaging members 506-508. In one aspect, the tissue engaging members 506-508 may be made of an electrically conductive metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art.

In one aspect, the upper and lower electrodes 503, 504 can be mass produced for a bipolar medical device, generally referred to as an electrosurgical device. A flexible electrically conductive sheet (e.g., Cu) may be bonded to an electrically insulative backing sheet (e.g., polyimide backing), and the tissue engaging members 506-508 may be printed at two or more locations on at least one of the upper and lower electrodes 503, 504. The tissue engaging members 506-508 may serve to assist or facilitate gripping, grasping, or manipulating tissue located between the upper and lower electrodes 503, 504 of the upper and lower jaw members 501, 502.

In one aspect, the upper and lower electrodes 503, 504 can be produced by laminating the metallic sheet to an electrically insulative film made of polyimide, polyester, fluorocarbon, or any polymeric material, or any combinations thereof. The electrically insulative layer, as well as the tissue engaging members 506-508, may be screen printed on the electrically conductive face of the upper and lower electrodes 503, 504. The shape of the upper and lower electrodes 503, 504 may be made by screen printing a protective barrier to the metallic film. This protective barrier may allow the shape of the upper and lower electrodes 503, 504 to be made by photoetching away the remaining material that does not make up the final shape of the upper and lower electrodes 503, 504. Finally, the individual electrode may be die-cut leaving an electrode subassembly that can be bonded to the upper and lower jaw members 501, 502.

The tissue engaging members 506-508 can have an adhesive or a brazable surface on the back side to attach the upper or lower electrode 503, 504 to the corresponding upper or lower jaw member 501, 502 of the end effector 500 depending on the jaw construction of the electrosurgical instrument 100 (FIG. 1).

Further, the upper and lower electrodes 503, 504 may be made of the following materials having the indicated thicknesses: copper, gold plated copper, silver, platinum, stainless steel, aluminum, or any suitable electrically conductive biocompatible material, among other electrically conductive metals and/or alloys. In one example, the upper and lower electrodes 503, 504 can include an electrically conductive metal layer (e.g., copper, gold plated copper, silver, platinum, stainless steel, aluminum, or any suitable electrically conductive biocompatible material, for example, among other electrically conductive metals and/or alloys), an electrically insulative film (e.g., polyimide, polyester, fluorocarbon, or any polymeric material, or any combinations thereof) bonded to the electrically conductive metal layer, and an adhesive used to bond the electrically conductive metal layer to the electrically insulative film.

In one example, the upper and lower electrode 503, 504 may comprise an acrylic-based copper clad laminate known under the tradename PYRALUX LF9250 supplied by DuPont, the copper clad laminate comprising a coverlay, a bondply, and a sheet adhesive. A coverlay may be a material laminated to the outside layers of the circuit to insulate the copper conductor. A bondply may be an adhesive system of unreinforced, thermoset based thin film available in various thicknesses intended for use in high performance, high reliability multi-layer flexible circuit constructions. In one aspect, the components of the upper and lower electrode 503, 504 may comprise a copper layer having a thickness of about 0.0028", a polyimide film layer having a thickness of about 0.005", and an adhesive layer having a thickness of about 0.001", for a total thickness of about 0.0088". In one aspect, the upper and lower electrode 503, 504 may comprise a copper layer having a thickness of about 0.0028", a polyimide film layer having a thickness of about 0.003", and an adhesive layer having a thickness of about 0.001" for a total thickness of about 0.0068". It will be appreciated that the thicknesses of the individual layers and the total thickness may vary based on the particular implementation details.

The various types of electrodes and tissue engaging members described in connection with the other figures herein can be manufactured in a manner similar to that described in the preceding paragraphs and for conciseness and clarity of disclosure will not be repeated in the description of such figures.

As used throughout this description, the electrically conductive gap setting member 505 may be a piece of material used to create or maintain a space between two things, such as upper and lower jaw members 501, 502 of the end effector 500. The gap setting member 505 may be made of a material that is electrically conductive and also is stiff to resist deformation in response to an applied force. The material is stiff with a high tensile strength and is incompressible. The gap setting member 505 is electrically conductive. In one aspect, the electrically conductive gap setting member may be made of an electrically conductive metal or metal alloy and preferably may be made of steel, such as medical grade stainless steel, for example. Alternatively, the gap setting member 505 may be made of exotic materials, including platinum, molybdenum disilicide, and silicon carbide provided that these materials have a suitable electrical conductivity. These are just a few examples, which are not meant to be limiting. In an electrically conductive configuration, the gap setting member 505 may be employed to set a uniform or non-uniform predetermined gap between tissue contacting surfaces of the electrodes 503, 504 of the upper and lower jaw members 501, 502.

The tissue engaging members 506-508 each may have the same height or different heights. The tissue engaging members 506-508 are provided for facilitating or assisting gripping, grasping, or otherwise manipulating tissue and thus do not contact the opposing electrode. In one aspect, the tissue engaging members 506-508 have a dimension or height that is less than the dimension or height of the electrically conductive gap setting member 505. The tissue engaging members 506-508 may have a height or heights different from the height of the gap setting member 505. The tissue engaging members 506-508 each may have the same height "h". The value of height "h" is smaller than the distance "g" set by the gap setting member 505, which may be the same as the size of the gap or the distance between the jaw members 501, 502 when the gap is uniform. Along the longitudinal axis "x", the distances W1, W2, W3 between the centers of the gap setting member 505 and the tissue engaging members 506-508 may be the same or different. The heights of the tissue engaging members 506-508 are selected such that the tissue or vessel media may be securely grasped and extruded into the recesses between the tissue engaging members 506-508 to assure electrical contact with the grasping surfaces. This develops a current flux flow path as represented, for example, at dashed lines 509, which extend directly across the surfaces of the upper and lower electrodes 503, 504, enhancing the most efficient hemostasis geometry for the instrument. Such extrusion of the tissue or vessel media into the recesses between the members may serve to achieve a secure grasping and sealing thereof during its surgical manipulation and throughout the coagulation process. The height of the gap setting member 505 may be selected to set a gap "g" that is greater than the height "h" and to facilitate or assist the application of a suitable pressure to the tissue when the upper and lower jaw members 501, 502 are in a closed position to promote an adequate tissue seal.

Figure 6:
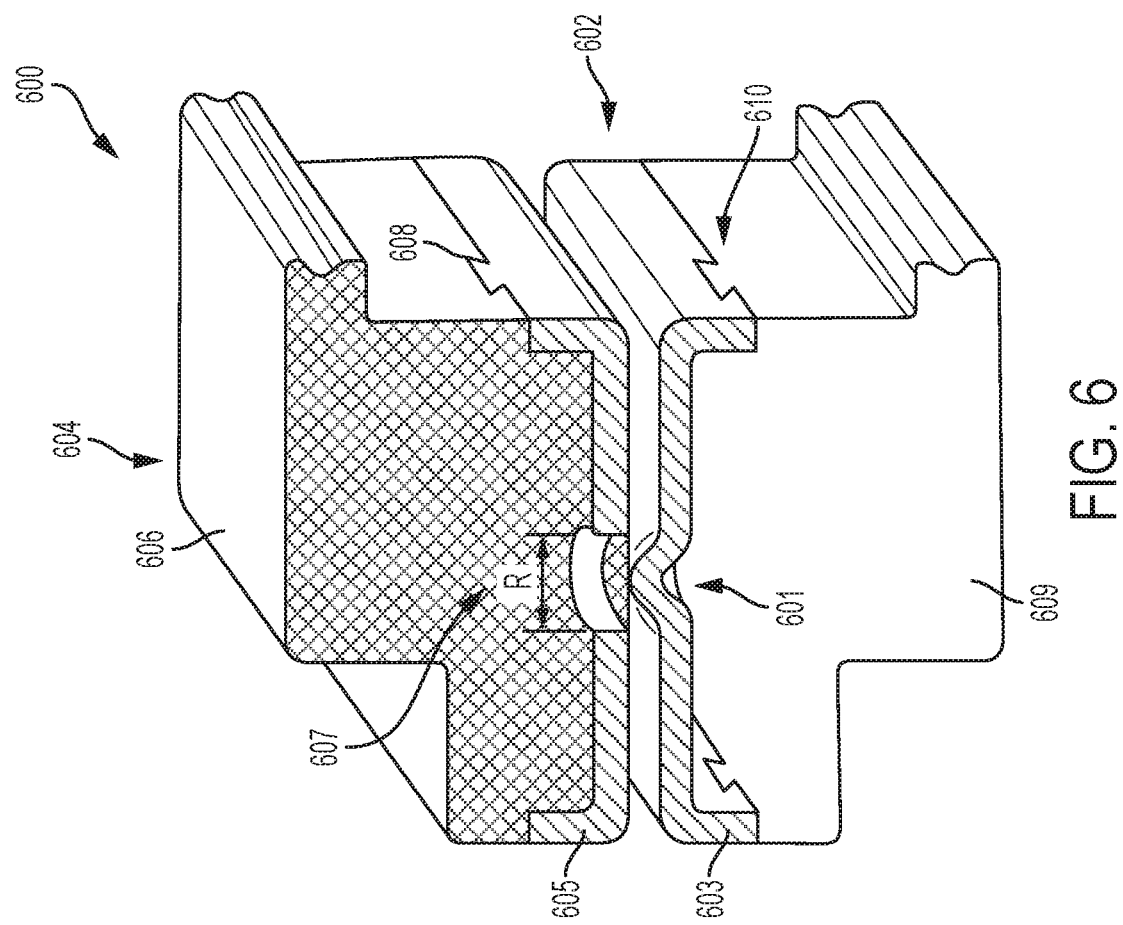
FIG. 6 shows one example embodiment of a portion of the jaw members comprising an electrically conductive tissue engaging member, according to one aspect of the present disclosure.

FIG. 6 shows one example embodiment of a portion 600 of the jaw members where one spacing member functioning as an electrically conductive tissue engaging member 601 may be made, according to one aspect of the present disclosure. The tissue engaging member 601 may be made integrally in the lower conductive layer 603 of the lower electrode 602. The lower electrode 602 may be coined or bent to form the spacing member 601. The lower electrode 602 includes a conductive layer 603 supported by an electrically insulative element 609. The upper electrode 604 includes a conductive layer 605 supported by an electrically insulative element 606. The conductive layer 603 of the lower electrode 602 faces the upper the conductive layer 605 of the upper electrode 604. The lower conductive layer 603 may be affixed to the lower insulative element 609 by a retention feature 610. The upper conductive layer 605 may be affixed to the upper insulative element 606 by another retention feature 608. The upper and lower conductive layers 605, 603 may be made of stainless steel or any other suitable material. The upper conductive layer 605 may be provided on the surface of the upper insulative element 606.

An opening 607 may be defined by the upper conductive layer 605 corresponding to the tissue engaging member 601. The opening 607 may be circular, oblong, or any other suitable shape cut out in the upper conductive layer 605 corresponding to the tissue engaging member 601 such that the tissue engaging member 601 may touch only the insulative element 606, but not the upper conductive layer 605 when the jaw members are in the closed position. The size of the opening 607 may depend on the configuration of the tissue engaging member 601. The opening 607 may have a diameter of 0.030". The opening 607 may be smaller than 0.030". The size of the opening 607 may depend on the manufacturing process. The opening 607 may not be so big as to affect the operation of the electrode. The opening 607 may be circular as shown here and may be rectangular or any other suitable shape, regular or irregular. There may be more than one spacing member and more than one corresponding opening, depending on the size, such as the length of the jaw members. There may be three such pairs of spacing members and corresponding openings. The size, dimension, shape, and number of the opening 607 may be configured and selected such that the electrosurgical device, the end effector, and the electrodes may achieve the requisite performance.

Figure 7:
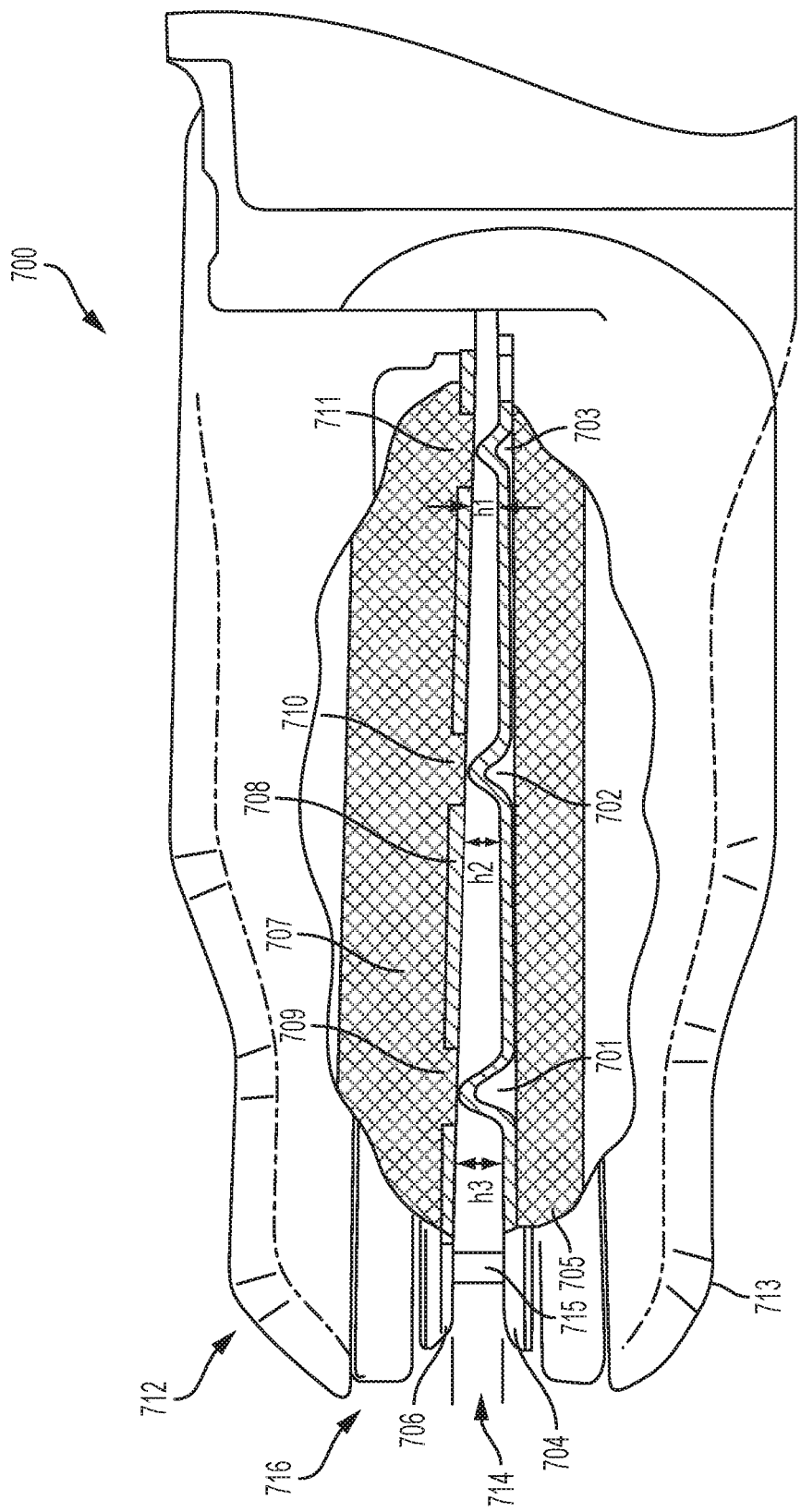
FIG. 7 shows a cross-sectional view of one example embodiment of an end effector comprising a distal electrically conductive gap setting member and the electrically conductive tissue engaging member shown in FIG. 6, according to one aspect of the present disclosure.

FIG. 7 shows a cross-sectional view of an end effector 700 comprising a distal electrically conductive gap setting member 715 and electrically conductive tissue engaging members 701-703, shown in FIG. 6, according to one aspect of the present disclosure. The tissue engaging members 701-703 may be made by bending or coining the conductive layer of the lower electrode 704. The lower electrode 704 is supported by an electrically insulative element 705. The upper electrode 706 comprises a conductive layer supported by an electrically insulative element 707. Openings 709-711 defined by the conductive 708 of the upper electrode 706 expose the insulative element 707 in the openings 709-711 to the corresponding tissue engaging members 701-703 such that the tissue engaging members 701-703 are not in electrical contact with the upper electrode 706. When the upper and lower jaw members 712, 713 of the end effector 700 are in the closed position, the tissue engaging members 701-703 may touch only the insulative element 707 exposed by the openings 709-711, but not the conductive layer 708 of the upper electrode 706. The heights h1-h3 of the tissue engaging members 701-703 may be the same or different. As shown in FIG. 7, the tissue engaging members 701-703 may have different heights is a non-uniform gap 714 between the upper and lower jaw members 712, 713 defined by the gap setting member 715.

The electrically conductive gap setting member 715 is located at the distal end 716 of the end effector 700. The gap setting member 715 may protrude through an opening 718 defined by the conductive layer of the lower electrode 704. There may be a space 720 between the inner periphery of the opening 718 and the outer periphery of the gap setting member 715 such that the gap setting member 715 may not contact any electrically conductive portion of the lower electrode 704. Although the opening 718 generally may have a substantially round shape, the opening 718 can have any shape as long as the inner periphery of the 718 may not contact the outer periphery of the gap setting member 715.

The gap setting member 715 may define a non-uniform gap 714 between the upper and lower jaw members 712, 713 by itself or together with the electrically conductive tissue engaging members 709-711 or other elements or techniques. The gap setting member 715 may be configured to form the non-uniform gap 714 between the upper and lower electrodes 706, 704 when the upper and lower jaw members 712, 713 in the closed position. Generally, a non-uniform gap may be defined by a minimum distance and a maximum distance between the upper and lower electrodes 706, 704 where the distance between the upper and lower electrodes 706, 704 varies linearly or non-linearly between the minimum and the maximum distance.

In one aspect, the gap setting member 715 is an electrically conductive metal pin made of a stiff incompressible material having a high tensile strength and suitable for setting a non-uniform gap 714 between the upper and lower electrodes 712, 713. In one aspect, the gap setting member 715 is made of an electrically conductive stiff incompressible material having a high tensile strength as described generally hereinabove and particularly in connection with FIGS. 3 and 5. For example, the gap setting member 715 may be made of metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art.

In one aspect, the tissue engaging members 701-703 may be made of an electrically conductive material and isolated from the energy source. The electrically conductive tissue engaging members 701-703 may be embedded in an electrically insulative material or may be coated with an electrically insulative material to prevent energy flow through the electrically conductive tissue engaging members 701-703. In one aspect, the tissue engaging members 701-703 may be made of an electrically conductive metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art.

Figure 8:
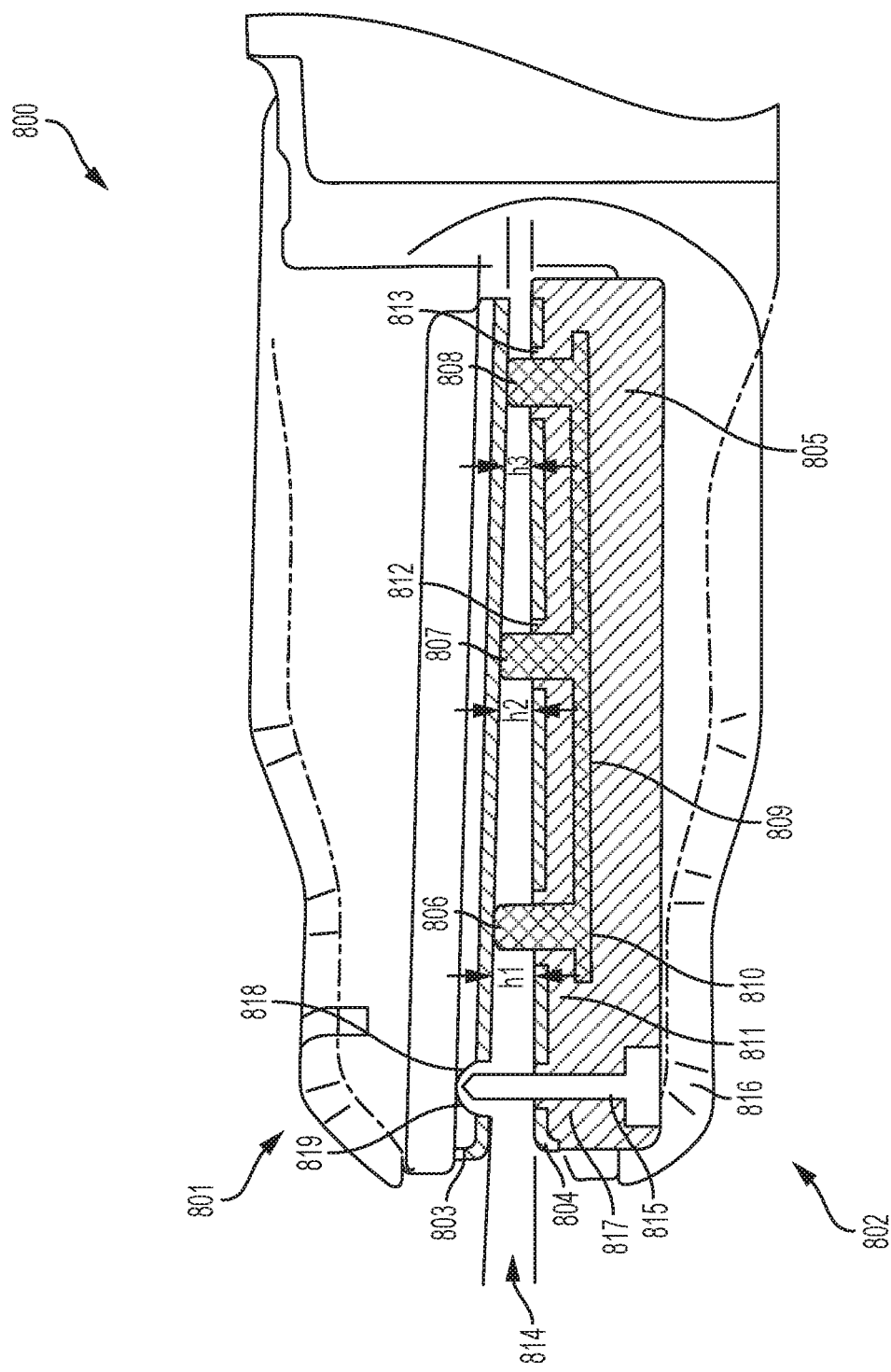
FIG. 8 shows a cross-sectional view of one aspect of an end effector comprising a distal electrically conductive gap setting member and tissue engaging members, according to one aspect of the present disclosure.

FIG. 8 shows a cross-sectional view of an end effector 800 comprising an electrically conductive gap setting member 815 and tissue engaging members 806, 807, 808, according to one aspect of the present disclosure. The end effector 800 may include an upper jaw member 801 and a lower jaw member 802. An upper electrode 803 may be provided on a lower surface of the upper jaw member 801. A lower electrode 804 may be provided on an upper surface of the lower jaw member 802. The lower jaw member 802 may comprise an electrically insulative element 805 positioned beneath the lower electrode 804. The insulative element 805 may be an electrically insulative glue, epoxy, or other resins. The tissue engaging members 806-808 may be provided on the lower jaw 802. The tissue engaging members 806-808 may be made on a stamped insert 809. The stamped insert 809 and the tissue engaging members 806-808 may be made of a plastic insulative material or a conductive material with an insulative coating. The stamped insert 809 may include a bottom 810 on which the elements 806-808 may be made. The stamped insert 809 may be inserted in the insulative element 805 in the lower jaw member 802. Openings 811-813 may be defined by the lower electrode 804 to allow the tissue engaging members 806-808 to protrude therethrough. At least portions of the and the tissue engaging members 806-808 may be exposed outside of the insulative element 805 and above the lower electrode 804. The heights h1-h3 of the and the tissue engaging members 806-808 exposed outside of the insulative element 805 may be the same or different. As shown here, the heights h1-h3 may be different such that a non-uniform gap 814 may be made between the upper and lower jaw members 801, 802. The and the tissue engaging members 806-808 may be configured to form a uniform gap, which is not shown here.

A gap setting member 815 may be provided on one of the upper or lower jaw members 801, 802, such as the lower jaw member 802. The gap setting member 815 may be made of an electrically conductive material. The gap setting member 815 may be a metal pin. The gap setting member 815. The gap setting member 815 may be affixed on and extend from a bottom 816 of the lower jaw member 802 through the insulative element 805 and an opening 817 defined by the lower electrode 804. A space may be provided between the inner periphery of the opening 817 and the outer periphery of the gap setting member 815 such that the gap setting member 815 does not contact any electrically conductive portion of the lower electrode 804. The opening 817 can have any shape as long as the inner periphery of the opening 817 may not touch the outer periphery of the gap setting member 815. The gap setting member 815 does not contact the upper electrode 803. As shown here, an opening 818 may be provided in the upper electrode 803 to expose an inner portion 819 of the upper jaw member 801. The gap setting member 815 may touch the inner portion 819 of the upper jaw 801, but not the upper electrode 803. The inner portion 819 of the upper jaw member 801 may be non-electrically conductive or connected to ground.

In one aspect, the tissue engaging members 806-808 may be made of an electrically insulative material as described generally hereinabove and particularly in connection with FIGS. 3 and 5. For example, the tissue engaging members 806-808 may be made of electrically insulative material such as a polymer and, more specifically, can be an electrically insulative material (e.g., polyimide, polyester, fluorocarbon, or any polymeric material, or any combinations thereof). The tissue engaging members 806-808 may be generally attached to the tissue contacting side of the upper jaw member 801. In one aspect, the tissue engaging members 806-808 may comprise a nonstick coating or may be made of a nonstick material such as TEFLON. Any nonstick material or nonstick surface finish may be suitable to prevent tissue from sticking to the electrically conductive portion of the upper electrode 803.

Alternatively, in one aspect, the tissue engaging members 806-808 may be made of an electrically conductive material and isolated from the energy source. The electrically conductive tissue engaging members 806-808 may be embedded in an electrically insulative material or may be coated with an electrically insulative material to prevent energy flow through the electrically conductive tissue engaging members 806-808. In one aspect, the tissue engaging members 806-808 and the insert 809 may be made of metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art and then coated with an electrically insulative material.

In one aspect, the electrically conductive gap setting member 815 is an electrically conductive metal pin made of a stiff incompressible material having a high tensile strength and suitable for setting a non-uniform gap 814 between the upper and lower electrodes 803, 804. In one aspect, the gap setting member 815 is made of an electrically conductive stiff incompressible material having a high tensile strength as described generally hereinabove and particularly in connection with FIGS. 3 and 5. For example, the gap setting member 815 may be made of metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art.

Figure 9:
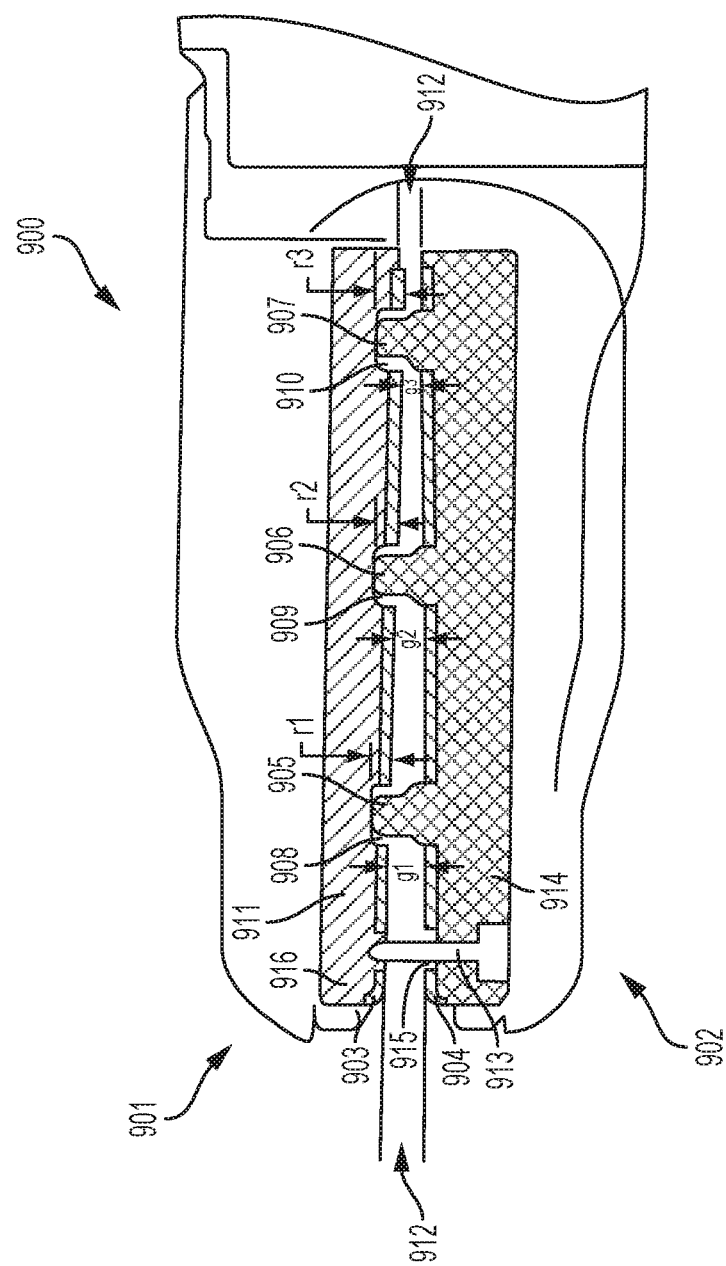
FIG. 9 shows a cross-sectional view of one aspect of an end effector comprising a distal electrically conductive gap setting member electrically isolated from an opposing electrode and tissue engaging members on one jaw member and buried in recesses defined in another jaw member, according to one aspect of the present disclosure.

FIG. 9 shows a cross-sectional view of one aspect of an end effector 900 comprising a distal electrically conductive gap setting member 913 electrically isolated from an opposing electrode 903 and tissue engaging members 905, 906, 907 on one jaw member 902 and buried in recesses 908, 909, 910 defined in another jaw member 901, according to one aspect of the present disclosure. The end effector 900 may comprise an upper jaw member 901 and a lower jaw member 902. An upper electrode 903 is provided on a lower surface of the upper jaw member 901. A lower electrode 904 is provided on an upper surface of the lower jaw member 902. The tissue engaging members 905-907 are provided on the lower jaw 902. Recesses 908-910 are provided on the upper electrode 903 corresponding to the tissue engaging members 905-907. The tissue engaging members 905-907 and the recesses 908-910 may be configured such that top portions of the tissue engaging members 905-907 may be buried in the recesses 908-910 without contacting the upper electrode 903. The tissue engaging members 905-907 may touch an inner element 911 of the upper jaw member 901. The insulative element 911 of the upper jaw member 901 may be made of an electrically insulative material. The tissue engaging members 905-907 may have the same height. The recesses 908-910 may have different depths r1, r3, r3. The tissue engaging members 905-907 and the recesses 908-910 may be configured to form a non-uniform gap 912 with different heights g1-g3 between the upper and lower jaw members 901, 902.

A gap setting member 913 is located on one of the jaw members 901, 902, such as the lower jaw member 902. The gap setting member 913 is made of an electrically conductive material. The gap setting member 913 may be a metal pin. The gap setting member 913 defines the non-uniform gap 912 together. The gap setting member 913 may be affixed on and extend from a bottom 914 of the lower jaw member 902 through an opening 915 defined by the lower electrode 904. There may be a space between the inner periphery of the opening 915 and the outer periphery of the gap setting member 913 such that the gap setting member 913 does not contact any electrically conductive portion of the lower electrode 904. The opening 915 can have any shape as long as the inner periphery of the opening 915 may not touch the outer periphery of the gap setting member 913. The gap setting member 913 may not touch the upper electrode 903. As shown here, an opening 916 may be provided in the upper electrode 903, and the inner insulative element 911 of the upper jaw member 901 may be exposed. The gap setting member 913 may touch the insulative element 911 of the upper jaw member 901, but not the upper electrode 903. The insulative element 911 of the upper jaw 901 may be nonconductive or connected to ground.

In one aspect, the tissue engaging members 905-907 may be made of an electrically insulative material as described generally hereinabove and particularly in connection with FIGS. 3 and 5. For example, the tissue engaging members 905-907 may be made of electrically insulative material such as a polymer and, more specifically, can be an electrically insulative material (e.g., polyimide, polyester, fluorocarbon, or any polymeric material, or any combinations thereof). The tissue engaging members 905-907 may be generally attached to the tissue contacting side of the upper jaw member 901. In one aspect, the tissue engaging members 905-907 may comprise a nonstick coating or may be made of a nonstick material such as TEFLON. Any nonstick material or nonstick surface finish may be suitable to prevent tissue from sticking to the electrically conductive portion of the upper electrode 903.

Alternatively, in one aspect, the tissue engaging members 905-907 may be made of an electrically conductive material and isolated from the energy source. The electrically conductive tissue engaging members 905-907 may be embedded in an electrically insulative material or may be coated with an electrically insulative material to prevent energy flow through the electrically conductive tissue engaging members 905-907. In one aspect, the tissue engaging members 905-907 may be made of metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art and then coated with an electrically insulative material.

In one aspect, the electrically conductive gap setting member 913 is an electrically conductive metal pin made of a stiff incompressible material having a high tensile strength and suitable for setting a non-uniform gap 912 between the upper and lower electrodes 903, 904. In one aspect, the gap setting member 913 is made of an electrically conductive stiff incompressible material having a high tensile strength as described generally hereinabove and particularly in connection with FIGS. 3 and 5. For example, the gap setting member 913 may be made of metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art.

Figure 10:
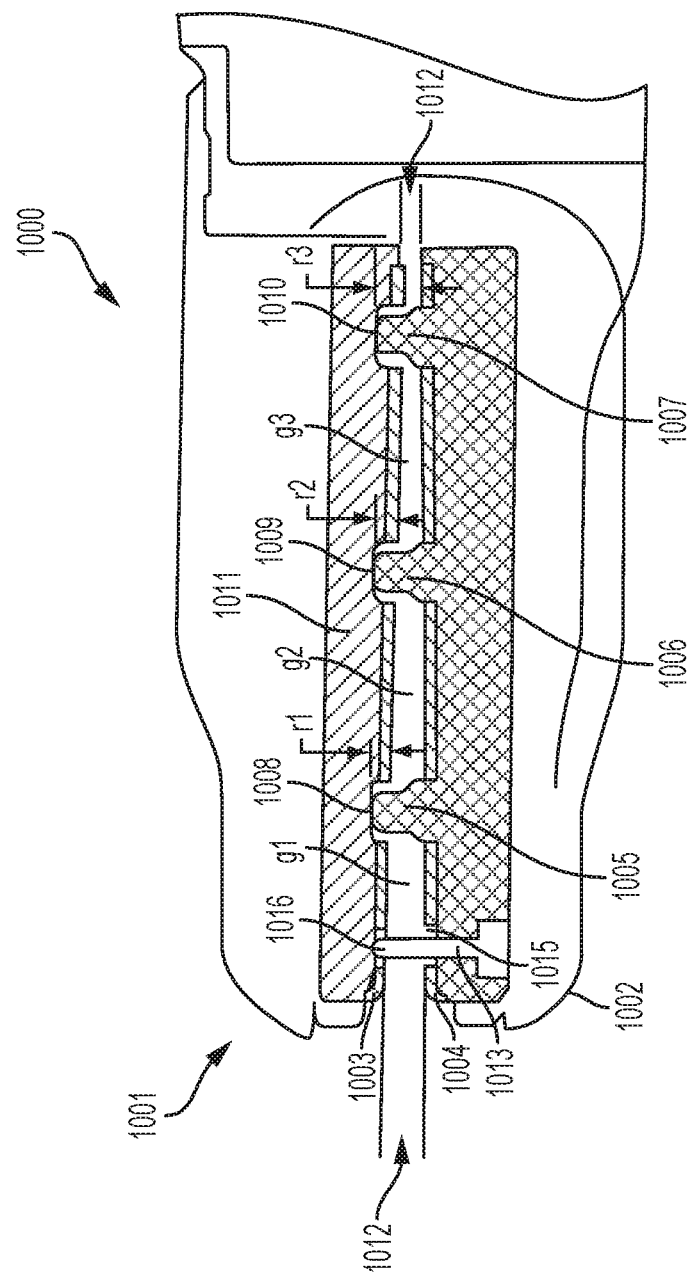
FIG. 10 shows a cross-sectional view of one example embodiment of an end effector comprising a distal electrically conductive gap setting member and tissue engaging members similar to the end effector shown in FIG. 9, except the gap setting member is in contact with the opposing electrode, according to one aspect of the present disclosure.

FIG. 10 shows a cross-sectional view of an end effector 1000 comprising a distal electrically conductive gap setting member 1013 and tissue engaging members 1005, 1006, 1007, according to one aspect of the present disclosure, where the gap setting member 1013 is in contact with the upper electrode 1003 on the upper jaw member 1001. The end effector 1000 may include an upper jaw member 1001 and a lower jaw member 1002. An upper electrode 1003 is provided on a lower surface of the upper jaw member 1001. A lower electrode 1004 is provided on an upper surface of the lower jaw member 1002. The tissue engaging members 1005-1007 may be provided on the lower jaw member 1002. Recesses 1008-1010 may be provided on the upper electrode 1003 corresponding to the tissue engaging members 1005-1007. The tissue engaging members 1005-1007 and the recesses 1008-1010 may be configured such that top portions of the tissue engaging members 1005-1007 are buried in the recesses 1008-1010 without contacting the upper electrode 1003. The tissue engaging members 1005-1007 may contact an inner electrically insulative element 1011 of the upper jaw 1001. The insulative element 1011 of the upper jaw 1001 may be nonconductive. The tissue engaging members 1005-1007 may have the same height. The recesses 1008-1010 may have different depths r1, r2, r3. The tissue engaging 1005-1007 and the recesses 1008-1010 may be configured to form a non-uniform gap 1012 with different heights g1, g2, g3 between the upper and lower jaw members 1001, 1002.

A gap setting member 1013 may be provided on one of the jaw members 1001, 1002, such as the lower jaw 1002. The gap setting member 1013 is made of an electrically conductive material. The gap setting member 1013 may be a metal pin. The gap setting member 1013 regulates the non-uniform gap 1012 between the upper and lower electrodes 1003, 1004. The gap setting member 1013 may be affixed on and extend from a bottom 1014 of the lower jaw member 1002 through an opening 1015 defined by the lower electrode 1004. There may be a space between the inner periphery of the opening 1015 and the outer periphery of the gap setting member 1013 such that the gap setting member 1013 may not touch any electrically conductive portion of the lower electrode 1004. The opening 1015 can have any shape as long as the inner periphery of the opening 1015 may not touch the outer periphery of the gap setting member 1013. As shown here, the gap setting member 1013 is in contact with the upper electrode 1003. Alternatively, the gap setting member 1013 may contact the electrically insulative element 1016 in the upper electrode 1003 through an opening provided in the upper electrode 1003. The gap setting member 1013 may be connected to ground.

In one aspect, the tissue engaging members 1005-1007 may be made of an electrically insulative material as described generally hereinabove and particularly in connection with FIGS. 3 and 5. For example, the tissue engaging members 1005-1007 may be made of electrically insulative material such as a polymer and, more specifically, can be an electrically insulative material (e.g., polyimide, polyester, fluorocarbon, or any polymeric material, or any combinations thereof). The tissue engaging members 1005-1007 may be generally attached to the tissue contacting side of the upper jaw member 1001. In one aspect, the tissue engaging members 1005-1007 may comprise a nonstick coating or may be made of a nonstick material such as TEFLON. Any nonstick material or nonstick surface finish may be suitable to prevent tissue from sticking to the electrically conductive portion of the upper electrode 1003.

Alternatively, in one aspect, the tissue engaging members 1005-1007 may be made of an electrically conductive material and isolated from the energy source. The electrically conductive tissue engaging members 1005-1007 may be embedded in an electrically insulative material or may be coated with an electrically insulative material to prevent energy flow through the electrically conductive tissue engaging members 1005-1007. In one aspect, the tissue engaging members 1005-1007 may be made of metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art and then coated with an electrically insulative material.

In one aspect, the electrically conductive gap setting member 1013 is an electrically conductive metal pin made of a stiff incompressible material having a high tensile strength and suitable for setting a non-uniform gap 1012 between the upper and lower electrodes 1003, 1004. In one aspect, the gap setting member 1013 is made of an electrically conductive stiff incompressible material having a high tensile strength as described generally hereinabove and particularly in connection with FIGS. 3 and 5. For example, the gap setting member 1013 may be made of metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art.

Figure 11:
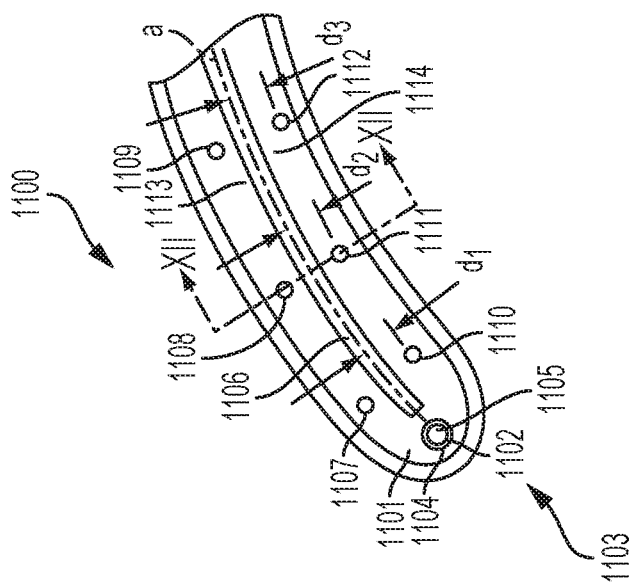
FIG. 11 shows a plan view of one aspect of a jaw member comprising a distal electrically conductive gap setting member and tissue engaging members evenly positioned along a width of the jaw member, according to one aspect of the present disclosure.

FIG. 11 shows a plan view of one example embodiment of a jaw member 1100 comprising a distal electrically conductive gap setting member 1102 and tissue engaging members 1107-1112 evenly positioned along a width of the jaw member 1100, according to one aspect of the present disclosure. An electrode 1101 is provided on one surface of the jaw member 1100. The gap setting member 1102 may be made of an electrically conductive material. In one aspect, the gap setting member 1102 is a metal pin 1102 located at the distal end 1103 of the jaw member 1100. The gap setting member 1102 protrudes through a an opening 1104 defined by the electrode 1101. A space 1105 is provided between the inner periphery of the opening 1104 and the outer periphery of the gap setting member 1102 to prevent the gap setting member 1102 from contacting any electrically conductive portion of the electrode 1101. Although the opening 1104 is shown to have a substantially round shape, the opening 1104 can have any shape provided that the inner periphery of the opening 1104 does not contact the outer periphery of the gap setting member 1102.

A knife channel 1106 is provided in the interior, such as the middle, of the jaw member 1100. A cutting member, not shown here, may be provided in the knife channel 1106 for cutting tissue after the tissue has been sealed using electrosurgical energy.

At least one tissue engaging member 1107-1112 is provided on the electrode 1101. The tissue engaging members 1107-1112 can be provided on the electrode 1101 on each side 1113, 1114 of and along the knife channel 1106. The tissue engaging members 1107-1112 may have the same or different shapes and may be spaced evenly or unevenly. The distances between the tissue engaging 1107-1112 and the knife channel 1106 may be the same or different. As shown here, the distances $d_1$, $d_2$, and $d_3$ between the tissue engaging members 1110-1112 and a longitudinal center axis a along the knife channel 1106 may be the same.

In one aspect, the tissue engaging members 1107-1112 are made of an electrically insulative material as described generally hereinabove and particularly in connection with FIGS. 3 and 5. For example, the tissue engaging members 1107-1112 may be made of electrically insulative material such as a polymer and, more specifically, can be an electrically insulative material (e.g., polyimide, polyester, fluorocarbon, or any polymeric material, or any combinations thereof). The tissue engaging members 1107-1112 may be generally attached to the tissue contacting side of the jaw member 1100. In one aspect, the tissue engaging members 1107-1112 may comprise a nonstick coating or may be made of a nonstick material such as TEFLON. Any nonstick material or nonstick surface finish may be suitable to prevent tissue from sticking to the electrically conductive portion of the upper electrode (not shown).

Alternatively, in one aspect, the tissue engaging members 1107-1112 may be made of an electrically conductive material and isolated from the energy source. The electrically conductive tissue engaging members 1107-1112 may be embedded in an electrically insulative material or may be coated with an electrically insulative material to prevent energy flow through the electrically conductive tissue engaging members 1107-1112. In one aspect, the tissue engaging members 1107-1112 may be made of metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art and then coated with an electrically insulative material.

In one aspect, the electrically conductive gap setting member 1102 is an electrically conductive metal pin made of a stiff incompressible material having a high tensile strength and suitable for setting a gap between the upper electrode (not shown) and the electrode 1101. In one aspect, the gap setting member 1102 is made of an electrically conductive stiff incompressible material having a high tensile strength as described generally hereinabove and particularly in connection with FIGS. 3 and 5. For example, the gap setting member 1102 may be made of metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art.

Figure 12:
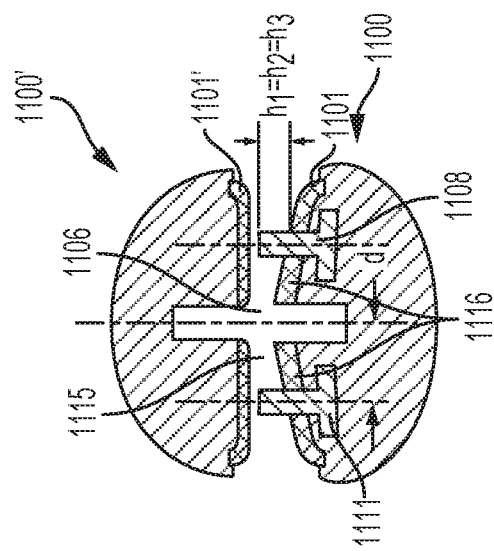
FIG. 12 shows a XII-XII sectional view of one example embodiment of an end effector with the jaw of FIG. 11, according to one aspect of the present disclosure.

FIG. 12 shows the XII-XII sectional view of one example embodiment of an end effector with the jaw 1100 of FIG. 11, according to one aspect of the present disclosure. At least one of the upper or lower electrodes 1101', 1101 define a taper 1116 that forms a non-uniform gap 1115 between the upper and lower jaw members 1100', 1100. The non-uniform gap 1115 between the upper and lower electrodes 1101', 1101 defined by the taper 1116 is narrowest along the central portion of the upper and lower jaw members 1100', 1100, for example, along the knife channel 1106, and gradually increases laterally toward the outside edges of the upper and lower jaw members 1100', 1100. The tissue engaging members 1107-1112 are disposed along the length of the lower electrode 1101, such that the opposing electrode 1101' does not contact the tissue engaging members 1107-1112.

With reference to FIGS. 11 and 12, a non-uniform but consistent spacing between the upper and lower electrodes 1101', 1101 of the upper and lower jaw members 1100', 1100 is set by the electrically conductive gap setting member 1102. The tissue engaging members 1107-1112 may be positioned evenly, as shown in FIG. 11, having the same distance d to the knife channel 1106, and be of uniform height. As shown here, the heights $h_1$, $h_2$, $h_3$ of the elements 1107-1109 may be the same. In one aspect, gap setting member 1102, as shown in FIG. 11, may be made of a metal or metal alloy and preferably may be made of steel, such as medical grade stainless steel, for example, suitable for setting a gap between the upper and lower electrodes 1101', 1101 of the upper and lower jaw members 1100', 1100.

Figure 13:
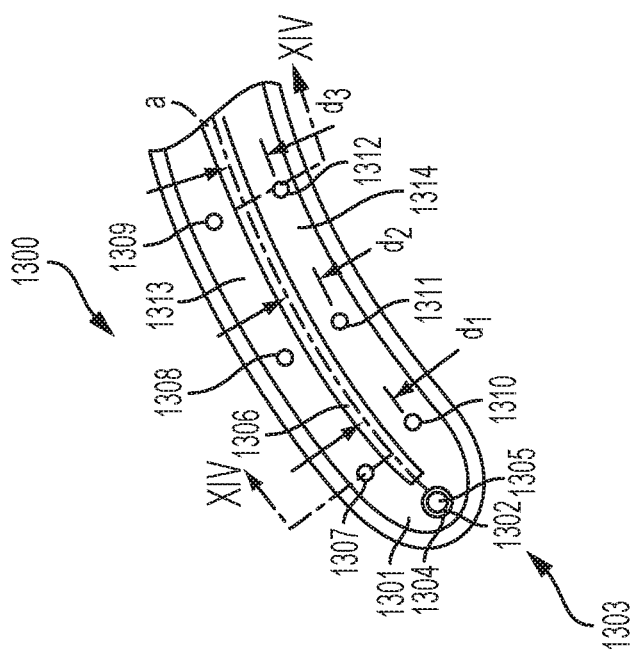
FIG. 13 shows a plan view of one aspect of a jaw member comprising a distal electrically conductive gap setting member and tissue engaging members unevenly positioned along a width of the jaw member, according to one aspect of the present disclosure.

Alternatively, FIG. 13 shows a plan view of one aspect of a jaw member 1300 comprising a distal electrically conductive gap setting member 1302 and tissue engaging members 1307-1312 oriented in a staggered uneven position and of non-uniform height, for example, according to one aspect of the present disclosure. An electrode 1301 is provided on one surface of the jaw member 1300. The gap setting member 1302 is located at the distal end 1303 of the jaw member 1300. The gap setting member 1302 protrudes through an opening 1304 defined by the electrode 1301. A space 1305 is provided between the inner periphery of the opening 1304 and the outer periphery of the gap setting member 1302 such that the member 1302 does not contact any electrically conductive portion of the electrode 1301. Although the opening 1304 is shown to have a substantially round shape, the opening 1304 can have any shape as long as the inner periphery of the opening 1304 may not contact the outer periphery of the gap setting member 1302.

A knife channel 1306 may be provided in the interior, such as the middle, of the jaw member 1300. A cutting member, not shown here, may be provided in the knife channel 1306 for cutting tissue after the tissue has been sealed using electrosurgical energy.

At least one tissue engaging member 1307-1312 is provided on the electrode 1301 on each side 1313, 1314 of and along the knife channel 1306. The tissue engaging members 1307-1312 may have the same or different shapes and may be spaced evenly or unevenly. The distances between the tissue engaging members 1307-1312 and the knife channel 1306 may be the same or different. As shown here, the distances $d_1$, $d_2$, $d_3$ between the tissue engaging members 1310-1312 and a longitudinal center axis a along the knife channel 1306 may be the same.

In one aspect, the tissue engaging members 1307-1312 are made of an electrically insulative material as described generally hereinabove and particularly in connection with FIGS. 3 and 5. For example, the tissue engaging members 1307-1312 may be made of electrically insulative material such as a polymer and, more specifically, can be an electrically insulative material (e.g., polyimide, polyester, fluorocarbon, or any polymeric material, or any combinations thereof). The tissue engaging members 1307-1312 may be generally attached to the tissue contacting side of the jaw member 1300. In one aspect, the tissue engaging members 1307-1312 may comprise a nonstick coating or may be made of a nonstick material such as TEFLON. Any nonstick material or nonstick surface finish may be suitable to prevent tissue from sticking to the electrically conductive portion of the upper electrode (not shown).

Alternatively, in one aspect, the tissue engaging members 1307-1312 may be made of an electrically conductive material and isolated from the energy source. The electrically conductive tissue engaging members 1307-1312 may be embedded in an electrically insulative material or may be coated with an electrically insulative material to prevent energy flow through the electrically conductive tissue engaging members 1307-1312. In one aspect, the tissue engaging members 1307-1312 may be made of metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art and then coated with an electrically insulative material.

In one aspect, the electrically conductive gap setting member 1302 is an electrically conductive metal pin made of a stiff incompressible material having a high tensile strength and suitable for setting a gap between the upper electrode (not shown) and the electrode 1301. In one aspect, the gap setting member 1302 is made of an electrically conductive stiff incompressible material having a high tensile strength as described generally hereinabove and particularly in connection with FIGS. 3 and 5. For example, the gap setting member 1302 may be made of metal or metal alloy and preferably may be made of steel, such as medical grade biocompatible stainless steel, for example, as well as electrically conductive components such as copper, silver, aluminum, tungsten, nickel, or any other electrically conductive materials that may occur to those skilled in the art.

Figure 14:
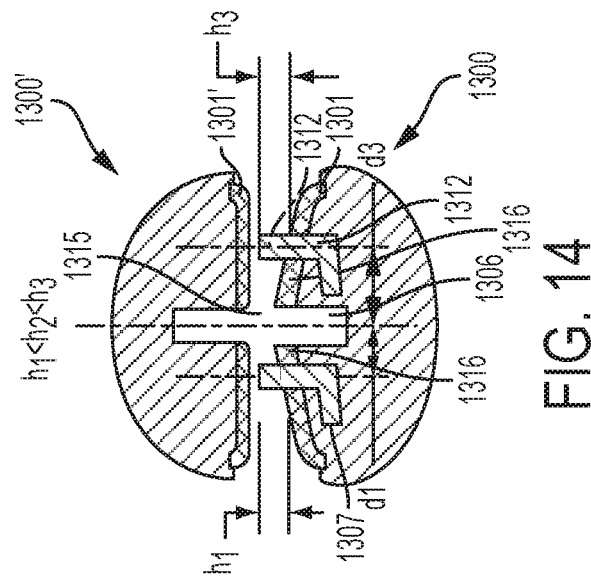
FIG. 14 shows a XIV-XIV sectional view of one example embodiment of an end effector with the jaw member of FIG. 13, according to one aspect of the present disclosure.

FIG. 14 shows the XIV-XIV sectional view of one example embodiment of an end effector with the jaw member of FIG. 13, according to one aspect of the present disclosure. At least one of the upper or lower electrodes 1301', 1301 define a taper 1316 that forms a non-uniform gap 1315 between the upper and lower jaw members 1300',

1300. The non-uniform gap 1315 between the upper and lower electrodes 1301', 1301 defined by the taper 1316 is narrowest along the central portion of the upper and lower jaw members 1300', 1300, for example, along the knife channel 1306, and gradually increases laterally toward the outside edges of the upper and lower jaw members 1300', 1300. The tissue engaging members 1307-1312 are disposed along the length of the electrode 1301, such that the opposing electrode 1301' does not contact the tissue engaging members 1307-1312.

With reference to FIGS. 13 and 14, a non-uniform but consistent spacing between the upper and lower jaw members 1300', 1300 is provided between the jaw members 1300', 1300 both laterally and longitudinally. However, different from the example embodiments of FIGS. 11 and 12, the tissue engaging members 1307-1312 may be positioned unevenly, as shown in FIG. 13, and be of non-uniform heights. The tissue engaging member 1307 and its corresponding tissue engaging member 1310 across the knife channel 1306 along a width of the lower jaw member 1300 may have the same distance $d_1$ from the longitudinal center axis a along the knife channel 1306 and the same height $h_1$. Similarly, the tissue engaging member 1308 and its corresponding tissue engaging member 1311 across the knife channel 1306 along a width of the lower jaw member 1300 may have the same distance $d_2$ from the longitudinal center axis a along the knife channel 1306 and the same height $h_2$ (not shown in the figures), and the tissue engaging member 1309 and its corresponding tissue engaging member 1312 across the knife channel 1306 along a width of the lower jaw member 1300 may have the same distance $d_3$ from the longitudinal center axis a along the knife channel 1306 and the same height $h_3$. As shown here, the heights $h_1$, $h_2$, $h_3$ may be different, for example, $h_1<h_2<h_3$.

Figure 15:
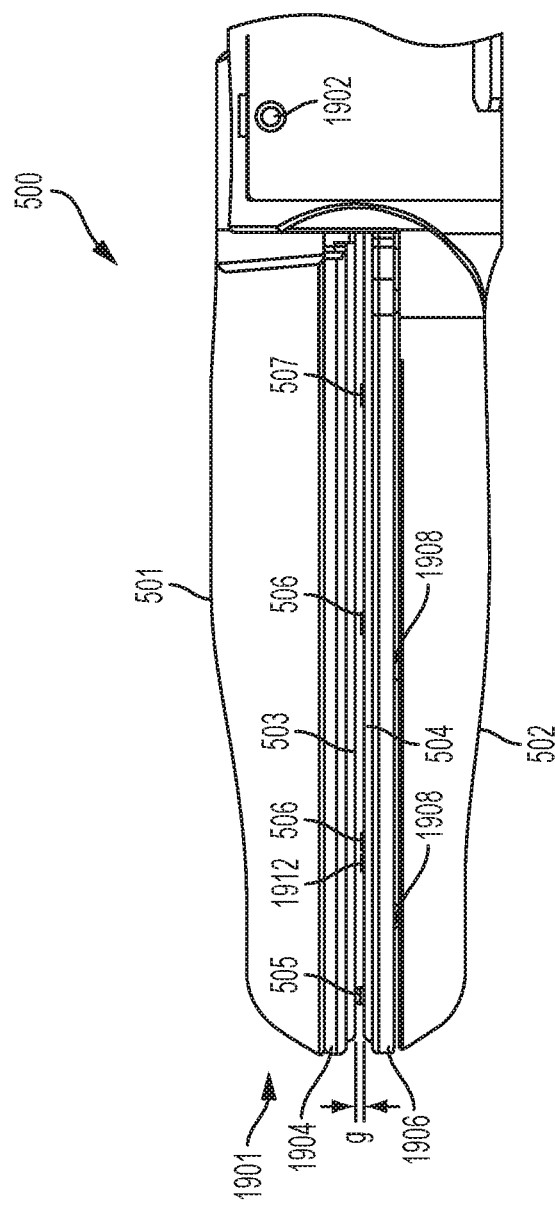
FIG. 15 is a side elevational view of the end effector of FIG. 5, according to one aspect of the present disclosure.

FIG. 15 is a side elevational view of the end effector 500 of FIG. 5, according to one aspect of the present disclosure. The end effector 500 comprises an upper jaw member 501 and a lower jaw member 502, where the upper jaw member 501 is pivotally movable between open and closed positions about a pivot 1902. As shown in FIG. 15, the upper jaw member 501 is in a closed position. The end effector 500 comprises an upper electrode 503 and a lower electrode 504. The upper electrode 503 is electrically isolated from the upper jaw member 501 by an electrically insulative element 1904 and the lower electrode 504 is electrically isolated from the lower jaw member 502 by another electrically insulative element 1906. The lower electrically insulative element 1906 and the lower electrode 504 are supported on the lower jaw member 502 by support members 1908. An electrically conductive gap setting member 505 is located on the distal end 1901 of the lower jaw member 502 and protrudes through an opening 1920 (see FIGS. 16, 19, 20) defined by the lower electrode 504 to electrically isolate the gap setting member 505 from the lower electrode 504. The gap setting member 505 sets a gap "g" between the upper and the lower electrodes 503, 504. Tissue engaging members 506-508, 1912 are disposed on the lower jaw member 502. The tissue engaging members 506-508, 1912 protrude through openings 1921, 512, 513, 514 (see FIGS. 16, 19, 20) defined by the lower electrode 504. The tissue engaging members 506-508, 1912 tightly or loosely fit through the openings.

Figure 16:
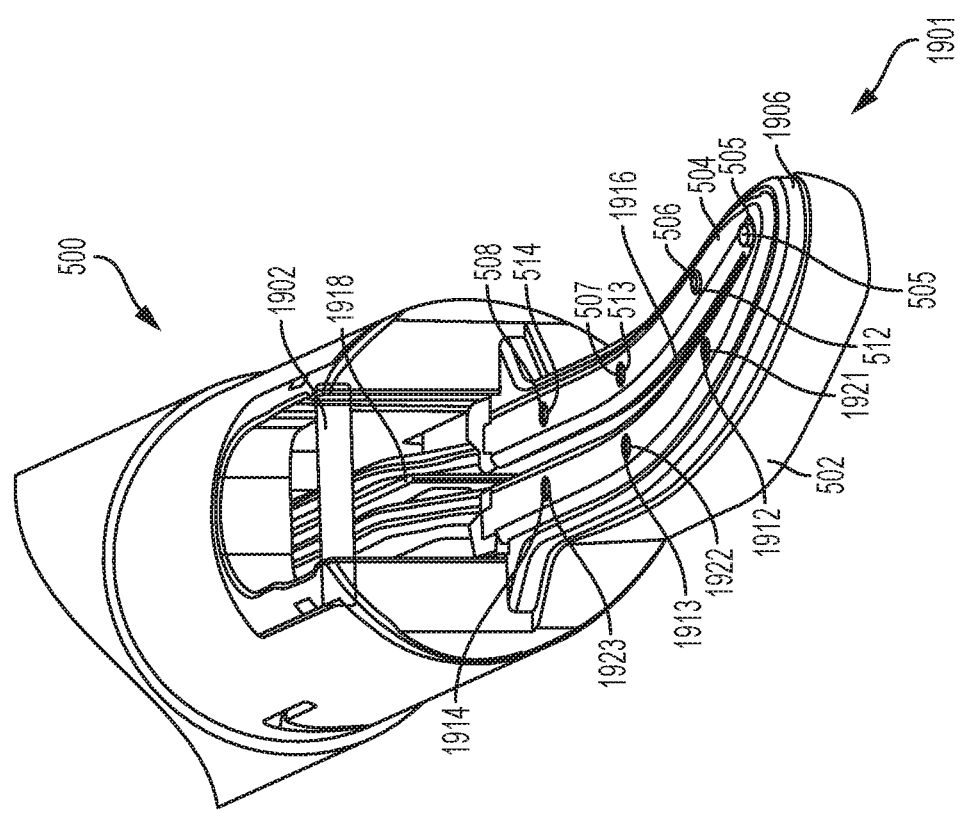
FIG. 16 shows a perspective view of the lower jaw member of FIG. 5, according to one aspect of the present disclosure.
Figure 17:
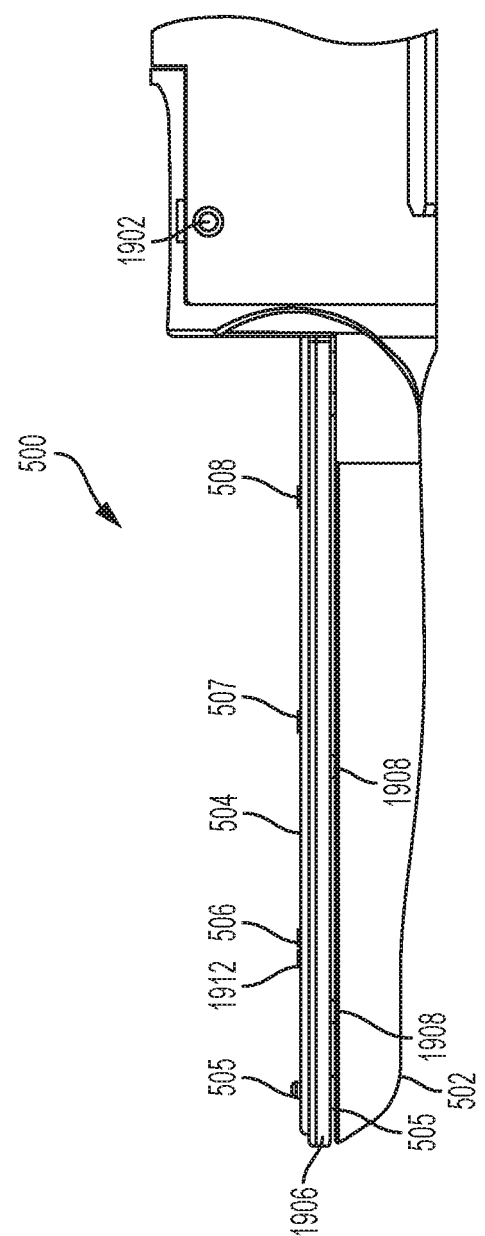
FIG. 17 shows a side elevational view of the lower jaw member of FIG. 16, according to one aspect of the present disclosure.

FIG. 16 shows a perspective view of the lower jaw member 502 of FIG. 15, according to one aspect of the present disclosure and FIG. 17 shows a side elevational view of the lower jaw member 502 of FIG. 15, according to one aspect of the present disclosure. With reference to FIGS. 16 and 17, the lower electrode 504 may be provided on an upper surface of the lower jaw member 502. The gap setting member 505 may be a metal pin provided on the upper face of the lower jaw member 502. The gap setting member 505 may protrude through an opening 511 defined by the electrode 504 without contacting the electrode 504. The tissue engaging members 506-508, 1912-1914 may be provided on the lower jaw member 502. The tissue engaging members 506-508 protrude through openings 512, 513, 514 defined by the lower electrode 504 and the tissue engaging members 1912-1914 protrude through openings 1921, 1922, 1923 also defined by the lower electrode 504.

Also shown in FIGS. 16 and 17 is a knife channel 1916 to slidably reciprocate a knife 1918 therealong. One set of the tissue engaging members 506-508 are located on one side of the knife channel 1916 and another set of the tissue engaging members 1912-1914 are located on the other side of the knife channel 1916. Also, shown in this view is the pivot 1902 about which the upper jaw member 501 (FIG. 15) pivots. As shown in FIG. 17, the gap setting member 505 is supported by the lower jaw member 502.

Figure 18:
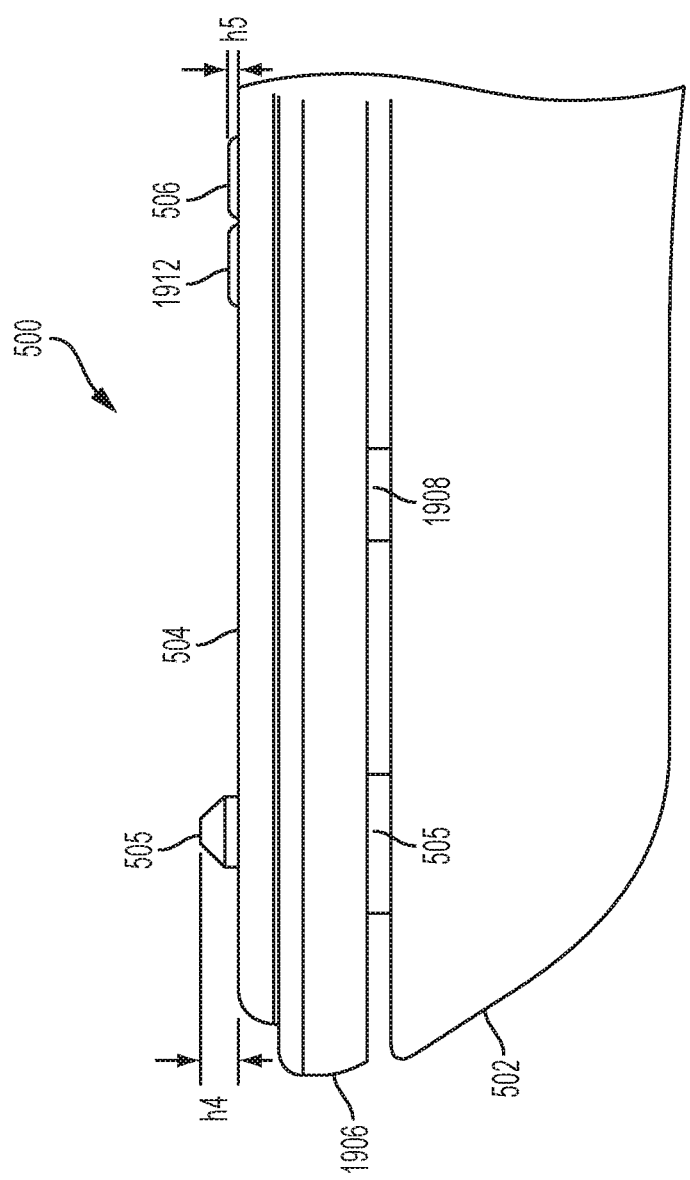
FIG. 18 shows a detail view of the distal end of the lower jaw member of FIG. 17, according to one aspect of the present disclosure.

FIG. 18 shows a detail view of the distal end 1901 of the lower jaw member 502 of FIG. 17, according to one aspect of the present disclosure. As shown, the electrically conductive gap setting member 505 protrudes through the lower electrode 504 and the lower electrically insulative element 1906 and is supported by the lower jaw member 502. The lower electrode 504 is supported by the electrically insulative element 1906, which is supported by support members 1908. This view shows the difference in height "h4" of the gap setting member 505 and the "h5" of the tissue engaging members 1912, 506. As previously discussed, the h5<h4 such that he gap setting member 505 sets the gap "g" between the upper and lower electrodes 503, 504.

Figure 19:
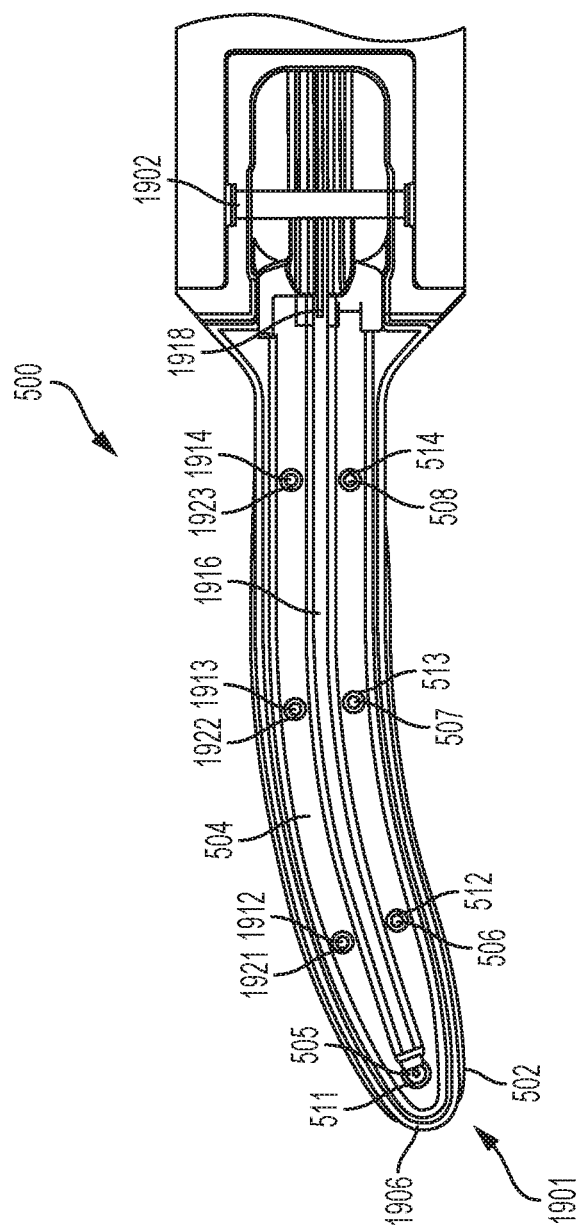
FIG. 19 shows a plan view of the lower jaw member of FIG. 16, according to one aspect of the present disclosure.
Figure 20:
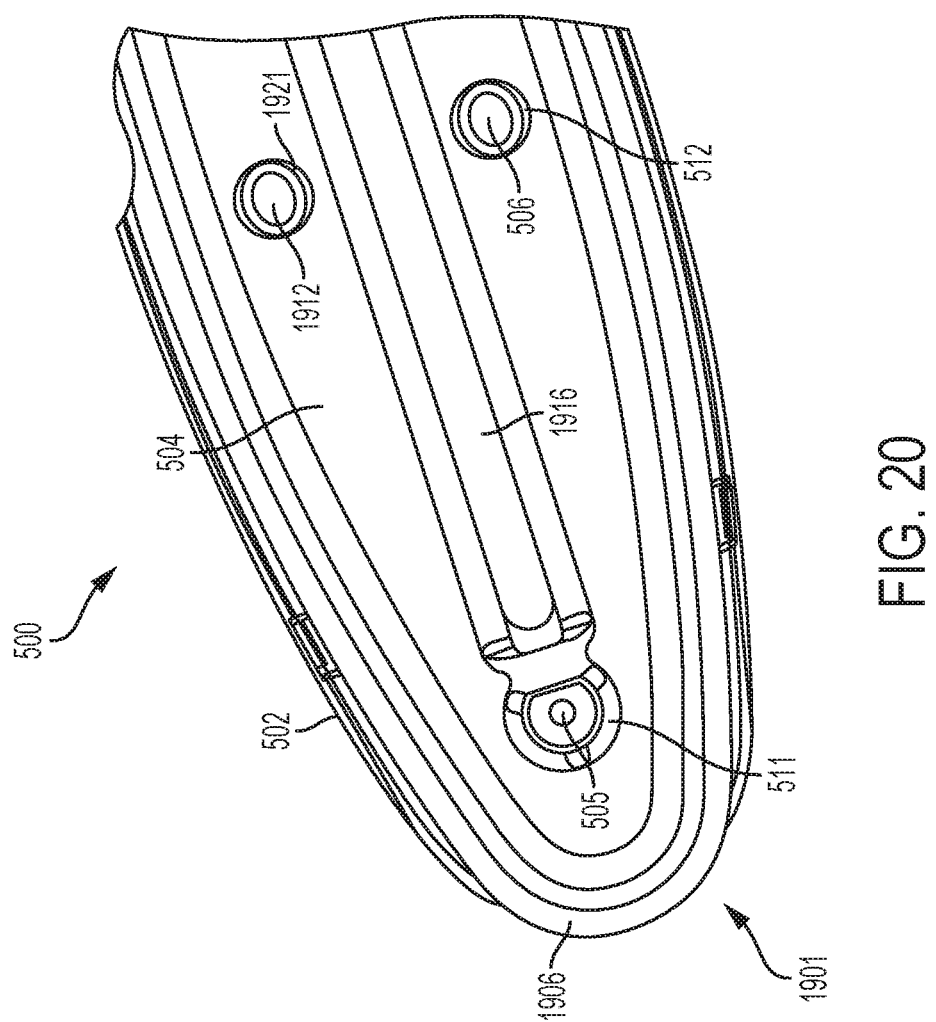
FIG. 20 shows a detail plan view of the distal end of the lower jaw member of FIG. 19, according to one aspect of the present disclosure.

FIG. 19 shows a plan view of the lower jaw member 502 of FIG. 15, according to one aspect of the present disclosure. FIG. 20 shows a detail plan view of the distal end 1901 of the lower jaw member 302 of FIG. 19, according to one aspect of the present disclosure. With reference now to FIGS. 19 and 20, the gap setting member 505 protrudes through the opening 1920 defined by the lower electrode 504 without contacting the lower electrode 504. The tissue engaging members 506-508, 1912-1914 are disposed on either side of the knife channel 1916.

It will be appreciated that the terms "proximal" and "distal" are used throughout the specification with reference to a clinician manipulating one end of an instrument used to treat a patient. The term "proximal" refers to the portion of the instrument closest to the clinician and the term "distal" refers to the portion located furthest from the clinician. It will further be appreciated that for conciseness and clarity, spatial terms such as "vertical," "horizontal," "up," "down," "upper," "lower," "top," or "bottom" may be used herein with respect to the illustrated aspects. However, surgical instruments may be used in many orientations and positions, and these terms are not intended to be limiting or absolute.

Various aspects of surgical instruments and robotic surgical systems are described herein. It will be understood by those skilled in the art that the various aspects described herein may be used with the described surgical instruments and robotic surgical systems. The descriptions are provided for example only, and those skilled in the art will understand that the disclosed examples are not limited to only the devices disclosed herein, but may be used with any compatible surgical instrument or robotic surgical system.

While various aspects herein have been illustrated by description of several aspects, and while the illustrative aspects have been described in considerable detail, it is not the intention of the applicant to restrict or in any way limit the scope of the appended claims to such detail. Additional advantages and modifications may readily appear to those skilled in the art. For example, it is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to an instrument for use only in conjunction with an endoscopic tube (e.g., trocar). On the contrary, it is believed that the present invention may find use in any procedure where access is limited to a small incision, including but not limited to laparoscopic procedures, as well as open procedures.

While the examples herein are described mainly in the context of electrosurgical instruments, it should be understood that the teachings herein may be readily applied to a variety of other types of medical instruments. By way of example only, the teachings herein may be readily applied to tissue graspers, tissue retrieval pouch deploying instruments, surgical staplers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

Aspects of the devices disclosed herein can be designed to be disposed of after a single use, or they can be designed to be used multiple times. Aspects may, in either or both cases, be reconditioned for reuse after at least one use. Reconditioning may include any combination of the steps of disassembly of the device, followed by cleaning or replacement of particular pieces, and subsequent reassembly. In particular, aspects of the device may be disassembled, and any number of the particular pieces or parts of the device may be selectively replaced or removed in any combination. Upon cleaning and/or replacement of particular parts, aspects of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and, if necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide, or steam.

Having shown and described various aspects of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, aspects, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

It is worthy to note that any reference to "one aspect," "an aspect," "one aspect," or "an aspect" means that a particular feature, structure, or characteristic described in connection with the aspect is included in at least one aspect. Thus, appearances of the phrases "in one aspect," "in an aspect," "in one aspect," or "in an aspect" in various places throughout the specification are not necessarily all referring to the same aspect. Furthermore, the particular features, structures or characteristics may be combined in any suitable manner in one or more aspects.

Although various aspects have been described herein, many modifications, variations, substitutions, changes, and equivalents to those aspects may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed aspects. The following claims are intended to cover all such modification and variations.

Some or all of the aspects described herein may generally comprise technologies for flexible circuits for electrosurgical instruments, or otherwise according to technologies described herein.

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will be incorporated only to the extent that no conflict arises between that incorporated material and the existing disclosure material.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different or other components. It is to be understood that such depicted architectures are merely exemplary, and that, in fact, many other architectures may be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more members are in direct physical or electrical contact with each other. In another example, some aspects may be described using the term "coupled" to indicate that two or more members are in direct physical or electrical contact. The term "coupled," however, also may mean that two or more members are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Further, a sale of a system or method may likewise occur in a territory even if components of the system or method are located and/or used outside the territory. Further, implementation of at least part of a system for performing a method in one territory does not preclude use of the system in another territory.

Although various aspects have been described herein, many modifications, variations, substitutions, changes, and equivalents to those aspects may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed aspects. The following claims are intended to cover all such modification and variations.

In summary, numerous benefits have been described that result from employing the concepts described herein. The foregoing description of the one or more aspects has been presented for purposes of illustration and description. It is not intended to be exhaustive or limiting to the precise form disclosed. Modifications or variations are possible in light of the above teachings. The one or more aspects were chosen and described in order to illustrate principles and practical application to thereby enable one of ordinary skill in the art to utilize the various aspects and with various modifications as are suited to the particular use contemplated. It is intended that the claims submitted herewith define the overall scope.

The invention claimed is:

1. An end effector, comprising:
a grasping portion, comprising:
a first jaw member comprising a first electrode;
a second jaw member comprising a second electrode, wherein at least one of the first and second jaw members is movable relative to the other between an open position and a closed position; and
a first electrically conductive member located either on the first jaw member or the second jaw member, the first electrically conductive member sized and configured to engage tissue, wherein the first electrically conductive member is electrically isolated from one of the first or second electrode; and
a gap setting portion comprising a second electrically conductive member located at a distal end portion of either the first jaw member or the second jaw member, wherein the second electrically conductive member is electrically isolated from one of the first or second electrodes, wherein the first electrode comprises a proximal portion and a distal portion, wherein the second electrode comprises a proximal portion and a distal portion, wherein a first height is defined between the proximal portion of the first electrode and the proximal portion of the second electrode when the first jaw member and the second jaw member are in the closed position, wherein a second height is defined between the distal portion of the first electrode and the distal portion of the second electrode when the first jaw member and the second jaw member are in the closed position, and wherein the first height and the second height are different.

2. The end effector of claim 1, wherein the first electrically conductive member is configured to engage the tissue when the tissue is located between the first and second jaw members.

3. The end effector of claim 1, wherein the first electrically conductive member is coated with an electrically insulative material.

4. The end effector of claim 1, wherein the first electrically conductive member is defined by the first electrode and the second electrode defines an opening that coincides with the first electrically conductive member such that the first electrically conductive member does not contact the second electrode.

5. The end effector of claim 1, wherein the second jaw member further comprises an opening in the second electrode corresponding to the first electrically conductive member and exposing an electrically insulative inner portion of the second jaw member.

6. The end effector of claim 5, wherein a top portion of the first electrically conductive member contacts the electrically insulative inner portion of the second jaw member and does not contact the second electrode.

7. The end effector of claim 5, wherein the opening defines a recess to receive the first electrically conductive member.

8. The end effector of claim 1, wherein the first electrically conductive member comprises two or more tissue engaging members.

9. The end effector of claim 8, wherein the second jaw member defines two or more openings in the second electrode each corresponding to each of the two or more tissue engaging members.

10. The end effector of claim 8, wherein the two or more tissue engaging members have different heights.

11. The end effector of claim 9, wherein the two or more openings define different depths.

12. The end effector of claim 8, wherein the two or more tissue engaging members have the same height.

13. The end effector of claim 1, wherein the first electrically conductive member is provided on an electrically conductive stamped member.

14. The end effector of claim 13, wherein the electrically conductive stamped member is inserted in an insulative material located in the first jaw member.

15. The end effector of claim 13, wherein the electrically conductive stamped member comprises a bottom, and wherein an insulative material is affixed on the bottom of the electrically conductive stamped member.

16. The end effector of claim 1, wherein the second jaw member defines an opening to receive the second electrically conductive member.

17. An electrosurgical device, comprising:
a handle assembly;
an end effector, comprising:
a grasping portion, comprising:
a first jaw member comprising a first electrode;
a second jaw member comprising a second electrode, wherein at least one of the first and second jaw members is movable relative to the other between an open position and a closed position; and
a first electrically conductive member located either on the first jaw member or the second jaw member, the first electrically conductive member sized and configured to engage tissue, wherein the first electrically conductive member is electrically isolated from one of the first or second electrode; and
a gap setting portion comprising a second electrically conductive member located at a distal end portion of either the first jaw member or the second jaw member, wherein the second electrically conductive member is electrically isolated from one of the first or second electrodes; and
a connecting member configured to connect the handle assembly and the end effector, wherein the first electrode comprises a proximal portion and a distal portion, wherein the second electrode comprises a proximal portion and a distal portion, wherein a first height is defined between the proximal portion of the first electrode and the proximal portion of the second electrode when the first jaw member and the second jaw member are in the closed position, wherein a second height is defined between the distal portion of the first electrode and the distal portion of the second electrode when the first jaw member and the second jaw member are in the closed position, and wherein the first height and the second height are different.

18. An electrosurgical system, comprising:
an electrosurgical energy generator; and
an electrosurgical device comprising:
  a handle assembly;
  an end effector, comprising:
    a grasping portion, comprising:
      a first jaw member comprising a first electrode;
      a second jaw member comprising a second electrode, wherein at least one of the first and second jaw members is movable relative to the other between an open position and a closed position; and
      a first electrically conductive member located either on the first jaw member or the second jaw member, the first electrically conductive member sized and configured to engage tissue, wherein the first electrically conductive member is electrically isolated from one of the first or second electrode; and
    a gap setting portion comprising a second electrically conductive member located at a distal end portion of either the first jaw member or the second jaw member, wherein the second electrically conductive member is electrically isolated from one of the first or second electrodes; and
  a connecting member configured to connect the handle assembly and the end effector, wherein the first electrode comprises a proximal portion and a distal portion, wherein the second electrode comprises a proximal portion and a distal portion, wherein a first height is defined between the proximal portion of the first electrode and the proximal portion of the second electrode when the first jaw member and the second jaw member are in the closed position, wherein a second height is defined between the distal portion of the first electrode and the distal portion of the second electrode when the first jaw member and the second jaw member are in the closed position, and wherein the first height and the second height are different.

* * * * *